US007696307B2

(12) United States Patent
Yu

(10) Patent No.: US 7,696,307 B2
(45) Date of Patent: Apr. 13, 2010

(54) FUNCTION AND REGULATION OF ADAMTS-1

(75) Inventor: Qin Yu, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 222 days.

(21) Appl. No.: 11/104,075

(22) Filed: Apr. 12, 2005

(65) Prior Publication Data
US 2007/0065831 A1 Mar. 22, 2007

Related U.S. Application Data

(60) Provisional application No. 60/650,027, filed on Feb. 4, 2005, provisional application No. 60/561,429, filed on Apr. 12, 2004.

(51) Int. Cl.
A61K 38/00 (2006.01)
C07K 2/00 (2006.01)
C07K 4/00 (2006.01)
A01N 37/18 (2006.01)
C07K 5/00 (2006.01)
C07K 7/00 (2006.01)
C07K 14/00 (2006.01)
C07K 16/00 (2006.01)
C07K 17/00 (2006.01)

(52) U.S. Cl. ............................. 530/300; 514/2
(58) Field of Classification Search ...................... None
See application file for complete search history.

(56) References Cited

U.S. PATENT DOCUMENTS 6,565,858 B2 * 5/2003 Hirose et al. ............. 424/278.1

OTHER PUBLICATIONS

Liu, Y-J, Xu, Y, and Yu, Q. Full-length ADAMTS-1 and the ADAMTS-1 fragments display pro- and antimetastatic activity, respectively. Oncogene, 2006. vol. 25, pp. 2452-2467.*
Burgess, Shaheen, Ravera, Jaye, Donohue, and Winkles. Possible dissociation of the heparin-binding and mitogenic activites of heparin-binding (acidic fibroblast) growth factor-1 from its receptor binding activities by site-directed mutagenesis of a single lysine residue. Journal of Cell Biology, 1990. vol. 111, pp. 2129-2138.*
Lazar, Watanbe, Dalton, and Sporn. Transforming growth factor a: mutation of aspartic acid 47 and leucine 48 results in different biological activities. Molecular and Cellular Biology, 1988. vol. 8, pp. 1247-1252.*
Schwartz, Burke, and Katsoyannis. A superactive insulin: [B10 aspartic acid] insulin (Human). Proceedings of the National Academy of Sciences, 1987. vol. 84, pp. 6408-6411.*
Lin, Wright, Hruby, and Rodbell. Structure-function relationships in glucagon: properties of highly purified Des-His1-Monoiodo-, and [Des-Asn28, Thr29](homoserine lactone27)-glucagon. Biochemistry, 1975. vol. 14, pp. 1559-1563.*

Abbaszade et al., Cloning and characterization of ADAMTS11, an aggrecanase from the ADAMTS family. The Journal of Biological Chemistry (1999) 274(33):23443-23450.
Adams et al., "Thrombospondins: multifunctional regulators of cell interactions," Annu. Rev. Cell Dev. Biol. (2001) 17:25-51.
Adams et al., "The thrombospondin type 1 repeat (TSR) superfamily: diverse proteins with related roles in neuronal development," Developmental Dynamics (2000) 218(2):280-299.
Agus et al., Targeting ligand-activated ErbB2 signaling inhibits breast and prostate tumor growth. Cancer Cell (2002) 2:127-137.
Ali et al., "Estrogen receptor-alpha in the inhibition of cancer growth and angiogenesis," Cancer Research 60(24):7094-7098, 2000.
Apte et al., "A disintegrin-like and metalloprotease (reprolysin type) with thrombospondin type 1 motifs in the ADAMTS family," The International Journal of Biochemistry & Cell Biology (2004) 36(6):981-985.
Arteaga "ErbB-targeted therapeutic approaches in human cancer," Experimental Cell Research. 2003. 284:122-130.
Bernfield et al., "Functions of cell surface heparan sulfate proteoglycans," Annu. Rev. Biochem., 1999. 68:729-777.
Billings et al., "Amphiregulin overexpression results in rapidly growing keratinocytic tumors: an invivo xenograft model of keratoacanthoma," American Journal of Pathology (2003) 163(6):2451-2458.
Blobel "Remarkable roles of proteolysis on and beyond the cell surface," Current Opinion in Cell Biology 12(5):606-612.
Bloemendal et al., "New strategies in anti-vascular cancer therapy," European Journal of Clinical Investigation (1999) 29:802-809.
Bornstein et al., "Thrombospondins: structure and regulation of expression," The FASEB Journal (1992) 6:3290-3298.
Bostwick et al., "Amphiregulin expression in prostatic intraepithelial neoplasia and adenocarcinoma: a study of 93 cases," The Prostate (2004) 58(2)164-168.
Cal et al., "Cloning, expression analysis, and structural characterization of seven novel human ADAMTSs, a family of metalloproteinases with disintegrin and thrombospondin-1 domains," Gene (2002) 283(1-2):49-62.
Chen et al., "Pharmacokinetics and tumor retention of 125I-labeled RGD peptide are improved by PEGylation," Nuclear Medicine and Biology (2004) 31(1):11-19.
Chen et al., "The cell biology of thrombospondin-1," Matrix Biology (2000) 19(7):597-614.
Colige et al., "Characterization and partial amino acid sequencing of a 107-kDa procollagen I N-proteinase purified by affinity chromatography on immobilized type XIV collagen," The Journal of Biological Chemistry (1995) 270(28):16724-16730.

(Continued)

Primary Examiner—Larry R. Helms
Assistant Examiner—Anne M. Gussow
(74) Attorney, Agent, or Firm—Pepper Hamilton LLP

(57) ABSTRACT

The present invention relates to ADAMTS-1 and uses thereof. The present invention also relates to fragments of ADAMTS-1 and methods of inhibiting cell growth and metastasis. The present invention also provide methods of identifying inhibitors and activators relating to the function of ADAMTS-1.

14 Claims, 15 Drawing Sheets

OTHER PUBLICATIONS

Colige et al., "cDNA cloning and expression of bovine procollagen I N-proteinase: a new member of the superfamily of zinc-metalloproteinases with binding sites for cells and other matrix components," *Proc. Natl. Acad. Sci. USA* (1997) 94:2374-2379.

Colige et al., "Cloning and characterization of ADAMTS-14, a novel ADAMTS displaying high homology with ADAMTS-2 and ADAMTS-3," *The Journal of Biological Chemistry* (2002) 277(8):5756-5766.

Cook et al., "A heparin sulfate-regulated human keratinocyte autocrine factor is similar or identical to amphiregulin," *Molecular and Cellular Biology* (1991) 11(5):2547-2557.

Cook et al., "Transgenic expression of the human amphiregulin gene induces a psoriasis-like phenotype," *The Journal of Clinical Investigation* (1997) 100(9):2286-2294.

Couchman "Syndecans: proteoglycan regulators of cell-surface microdomains?," *Nature* (2003) 4(12):926-937.

Fernandes et al., "Procollagen II amino propeptide processing by ADAMTS-3. Insights on dermatosparaxis," *The Journal of Biological Chemistry* (2001) 276(34):31502-31509.

Fischer et al., "EGFR signal transactivation in cancer cells," *Biological Society* (2003) 31(part6):1203-1208.

Flannery et al., "Autocatalytic cleavage of ADAMTS-4 (Aggrecanase-1) reveals multiple glycosaminoglycan-binding sites," *The Journal of Biological Chemistry* (2002) 277(45):42755-42780.

Gao et al., "ADAMTS4 (aggrecanase-1) activation on the cell surface involves C-terminal cleavage by glycosylphosphatidyl inositol-anchored membrane type 4-matrix metalloproteinase and binding of the activated proteinase to chondroitin sulfate and heparan sulfate on syndecan-1," *The Journal of Biological Chemistry* (2004) 279(11):10042-10051.

Good et al., "A tumor suppressor-dependent inhibitor of angiogenesis is immunologically and functionally indistinguishable from a fragment of thrombospondin," *Proc. Natl. Acad. Sci. USA* (1990) 87(17):6624-6628.

Gschwind et al., "'TACE cleavage of proamphiregulin regulates GPCR-induced proliferation and motility of cancer cells," *The EMBO Journal* (2003) 22(10):2411-2421.

Guy et al. "Expression of the neu protooncogene in the mammary epithelium of transgenic mice induces metastatic disease," *Proc. Natl. Acad. Sci. USA* (1992) 89(22):10578-10582.

Hanahan et al., "The hallmarks of cancer," *Cell* (2000) 100:57-70.

Harris et al., "EGF receptor ligands," *Experimental Cell Research* (2003) 284(1):2-13.

Hashimoto et al., "Heparin-binding epidermal growth factor-like growth factor is an autocrine growth factor for human keratinocytes," *The Journal of Biological Chemistry* (1994) 269(31):20060-20066.

Herren "ADAM-mediated shedding and adhesion: a vascular perspective," *News Physiol Sci* (2002) 17:73-76.

Huang et al., "The enhanced tumorigenic activity of a mutant epidermal growth factor receptor common in human cancers is mediated by threshold levels of constitutive tyrosine phosphorylation and unattenuated signaling," *The Journal of Biological Chemistry* (1997) 272(5)2927-2935.

Iozzo et al., "Heparan sulfate proteoglycans: heavy hitters in the angiogenesis arena," *The Journal of Clinical Investigation* (2001) 108(3):349-355.

Iruela-Arispe et al., "ADAMTS1: A matrix metalloprotease with angioinhibitory properties," *Ann. N. Y. Acad. Sci.* (2003) 995:183-190.

Iruela-Aripse et al., "Inhibition of angiogenesis by thrombospondin-1 is mediated by 2 independent regions within the type 1 repeats," *Circulation* (1999) 100(13):1423-1431.

Iruela-Arispe et al., "Thrombospondin exerts an antiangiogenic effect on cord formation by endothelial cells in vitro," *Proc. Natl. Acad. Sci. USA* (1991) 88(11):5026-5030.

Iwamoto et al., "Heparin-binding EGF-like growth factor and ErbB signaling is essential for heart function," *PNAS* (2003) 100(6):3221-3226.

Jackson et al., "Defective valvulogenesis in HB-EGF and TACE-null mice is associated with aberrant BMP signaling," *The EMBO Journal* (2003) 22(11):2704-2716.

Kang et al., "A multigenic program mediating breast cancer metastasis to bone," *Cancer Cell* (2003) 3(6):537-549.

Kashiwagi et al., "TIMP-3 is a potent inhibitor of aggrecanase 1 (ADAM-TS4) and aggrecanase 2 (ADAM-TS5)," *The Journal of Biological Chemistry* (2001) 276(16):12501-12504.

Kaushal et al., "The new kids on the block: ADAMTSs, potentially multifunctional metalloproteinases of the ADAM family," *The Journal of Clinical Investigation* (2000) 105(10):1335-1337.

Kuno et al., "Molecular cloning of a gene encoding a new type of metalloproteinase-disintegrin family protein with thrombospondin motifs as an inflammation associated gene," *The Journal of Biological Chemistry* (1997) 272(1):556-562.

Kuno et al., "ADAMTS-1 protein anchors at the extracellular matrix through the thrombospondin type I motifs and its spacing region," *The Journal of Biological Chemistry* (1998) 273(22):13912-13917.

Kuno et al., "The carboxyl-terminal half region of ADAMTS-1 suppresses both tumorigenicity and experimental tumor metastatic potential," *Biochemical and Biophysical Research Communications* (2004) 319:1327-1333.

Kuno et al., "ADAMTS-1 is an active metalloproteinase associated with the extracellular matrix," *The Journal of Biological Chemistry* (1999) 274(26):18821-18826.

Lawler "Thrombospondin-1 as an endogenous inhibitor of angiogenesis and tumor growth," *J. Cell. Mol. Med.* (2002) 6(1):1-12.

Leach et al., "Heparin-binding EGF-like growth factor regulates human extravillous cytotrophoblast development during conversion to the invasive phenotype," *Development Biology* (2004) 266(2):223-237.

Lee et al., "TACE/ADAM17 processing of EGFR ligands indicates a role as a physiological convertase," *Ann. N. Y. Acad. Sci.* (2003) 995:22-38.

Luque et al., "ADAMTS1/METH1 inhibits endothelial cell proliferation by direct binding and sequestration of VEGF165," *The Journal of Biological Chemistry* (2003) 278(26):23656-23665.

Ma et al., "Antisense expression for amphiregulin suppresses tumorigenicity of a transformed human breast epithelial cell line," *Oncogene* (1999) 18:6513-6520.

Maeshima et al., "Tumstatin, an endothelial cell-specific inhibitor of protein synthesis," *Science* (3003) 295:140-143.

Masui et al. "Expression of METH-1 and METH-2 in pancreatic cancer," *Clinical Cancer Research* (2001) 7(11):3437-3443.

Massague et al., "Membrane-anchored growth factors," *Annu. Rev. Biochem.* (1993) 62:515-541.

Matthews et al., "Brain-enriched hyaluronan binding (BEHAB)/brevican cleavage in a glioma cell line is mediated by a disintegrin and metalloproteinase with thrombospondin motifs (ADAMTS) family member," *The Journal of Biological Chemistry* (2000) 275(30):22695-22703.

McFall et al., "Characterization of the high affinity cell-binding domain in the cell surface proteoglycan syndecan-4," *The Journal of Biological Chemistry* (1998) 273(43):28270-28276.

Merlos-Suarez et al., "Metalloprotease-dependent Protransforming Growth Factor-χ Ectodomain Shedding in the Absence of Tumor Necrosis Factor-χ-converting Enzyme," *The Journal of Biological Chemistry* (2001) 276:48510-48517.

Miao et al., "Thrombospondin-1 Type 1 Repeat Recombinant Proteins Inhibit Tumor Growth through Transforming Growth Factor-β-dependent and -independent Mechanisms," *Cancer Research* (2001) 61:7830-7839.

Miles et al., "ADAMTS-1: A cellular disintegrin and metalloprotease with thrombospondin motifs is a target for parathyroid hormone in bone," *Endocrinology* (2000) 141(12):4533-4542.

Minn et al., "Distinct organ-specific metastatic potential of individual breast cancer cells and primary tumors," *The Journal of Clinical Investigation* (2005)115(1):44-55.

Bornstein, "Thrombospondins as matricellular modulators of cell function," *Journal of Clinical Investigation* (2001) 107(8):929-934.

Mittaz et al., "ADAMTS-1 Is Essential for the Development and Function of the Urogenital System," *Biology of Reproduction* (2004) 70:1096-1105.

Miyamoto et al., "Heparin-Binding EGF-Like Growth Factor Is a Promising Target for Ovarian Cancer Therapy," *Cancer Research* (2004) 64:5720-5727.

Montgomery et al., "Differential Modulation of Mitogen-activated Protein (MAP) Kinase/Extracellular Signal-related Kinase Kinase and MAP Kinase Activities by a Mutant Epidermal Growth Factor Receptor," *The Journal of Biological Chemistry* (1995) 270(51):30562-30566.

Niemeyer et al., "Preneoplastic mammary tumor markers: Cripto and Amphiregulin are overexpressed in hyperplastic stages of tumor progression in transgenic mice," *Int. J. Cancer* (1999) 81(4):588-591.

Nokihara et al., "Natural Killer Cell-dependent Suppression of Systemic Spread of Human Lung Adenocarcinoma Cells by Monocyte Chemoattractant Protein-1 Gene Transfection in Severe Combined Immunodeficient Mice," *Cancer Research* (2000) 60:7002-7007.

Ongusaha et al., "HB-EGF Is a Potent Inducer of Tumor Growth and Angiogenesis," *Cancer Research* (2004) 64:5283-5290.

O'Reilly et al., "Antiangiogenic activity of the cleaved conformation of the serpin antithrombin," *Science* (1999) 285:1926-1928.

Peschon et al., "An essential role for ectodomain shedding in mammalian development," *Science* (1998) 282(5392):1281-1284.

Pfeifer et al., "Suppression of angiogenesis by lentiviral delivery of PEX, a noncatalytic fragment of matrix metalloproteinase 2," *PNAS* (2000) 97(22):12227-12232.

Plaimauer et al., "Cloning, expression, and functional characterization of the von Willebrand factor-cleaving protease (ADAMTS13)," *Blood* (2002) 100(10):3626-3632.

Porter et al., "Dysregulated expression of adamalysin-thrombospondin genes in human breast carcinoma," *Clinical Cancer Research* (2004) 10(7):2429-2440.

Rodriguez-Manzaneque et al., "Characterization of METH-1/ADAMTS1 processing reveals two distinct active forms," *The Journal of Biological Chemistry* (2000) 275(42):33471-33479.

Russell et al., "Processing and Localization of ADAMTS-1 and Proteolytic Cleavage of Versican during Cumulus Matrix Expansion and Ovulation," *The Journal of Biological Chemistry* (2003) 278(43):42330-42339.

Saaristo et al., "Mechanisms of angiogenesis and their use in the inhibition of tumor growth and metastasis," *Oncogene* 19:6122-6129.

Safavy et al., "Synthesis and biological evaluation of paclitaxel-C225 conjugate as a model for targeted drug delivery," *Bioconjugate Chem.* (2003) 14(2):302-310.

Sahin et al., Distinct roles for ADAM10 and ADAM17 in ectodomain shedding of six EGFR ligands. *Journal of Cell Biology* (2004) 164(5):769-779.

Sandy et al., "Versican V1 Proteolysis in Human Aorta *in Vivo* Occurs at the $Glu^{441}$-$Ala^{442}$ Bond,-asite that is Cleaved by Recombinant ADAMTS-1 and ADAMTS-4," *The Journal of Biological Chemistry* (2001), 276: 13372-13378.

Schafer et al., "Multiple G-protein-coupled receptor signals converge on the epidermal growth factor receptor to promote migration and invasion," *Oncogene* (2004) 23(4):991-999.

Seals et al., The ADAMs family of metalloproteases: multidomain proteins with multiple functions. *Genes and Development* (2003) 17:7-30.

Shindo et al., "ADAMTS-1: a metalloproteinase-disintegrin essential for normal growth, fertility, and organ morphology and function," *The Journal of Clinical Investigation* (2000) 105(10):1345-1352.

Somerville et al., "Characterization of ADAMTS-9 and ADAMTS-20 as a Distinct ADAMTS subfamily related to *Caenorhabditis elegans* GON-1," *The Journal of Biological Chemistry* (2003) 278(11):9503-9512.

Stern et al., "Tyrosine kinase signalling in breast cancer: ErbB family receptor tyrosine kinases," *Cancer Research* (2000) 2:176-183.

Streit et al., "Overexpression of thrombospondin-1 decreases angiogenesis and inhibits the growth of human cutaneous squamous cell carcinomas," *American Journal of Pathology* (1999) 155(2):441-452.

Streit et al., "Thrombospondin-1 suppresses wound healing and granulation tissue formation in the skin of transgenic mice," *The EMBO Journal* (2000) 19(13):3272-3282.

Stern "Tyrosine kinase signalling in breast cancer: ErbB family receptor tyrosine kinases," *Breast Cancer Research* (2000) 2(3):176-183.

Sunnarborg et a., "Tumor Necrosis Factor-α Converting Enzyme (TACE) Regulates Epidermal Growth Factor Receptor Ligand Availability," *The Journal of Biological Chemistry* (2002) 277(15):12838-12845.

Thai et al., "Expression of ADAMTS1 during murine development," *Mechanisms of Development*, 2002. 115:181-185.

Tolsma et al., "Peptides derived from two separate domains of the matrix protein thrombospondin-1 have anti-angiogenic activity," *The Journal of Cell Biology* (1993) 122(2):497-511.

Tomioka et al., "Inhibition of Growth, Invasion, and Metastasis of Human Pancreatic Carcinoma cells by NK4 in an Orthotopic Mouse Model," *Cancer Research* (2001) 61:7518-7524.

Tortorella et al., Purification and cloning of aggrecanase-1: a member of the ADAMTS family of proteins. Science. (1999) 284(5420):1664-1666.

Tucker "The thrombospondin type 1 repeat superfamily," *IJBCB* (2004) 36(6):969-974.

Vankemmelbeke et al., "Expression and activity of ADAMTS-5 in synovium," *Eur. J. Biochem.*, 268(5):1259-1268, 2001.

Vazquez et al., "METH-1, a human ortholog of ADAMTS-1, and METH-2 are members of a new family of proteins with angio-inhibitory activity," *The Journal of Biological Chemistry* (1999) 274(33):23349-23357.

Volpert et al., "A human fibrosarcoma inhibits systemic angiogenesis and the growth of experimental metastasis via thrombospondin-1," *Proc. Natl. Acad. Sci. UDS* (1998) 95(11):6343-6348.

Williams et al., "Loss of caveolin-1 gene expression accelerates the development of dysplastic mammary lesions tumor-prone transgenic mice," Molecular Biology of the Cell (2003) 14(3):1027-1042.

Wolfsberg et al., "ADAM, a novel family of membrane proteins containing A Disintegrin And metalloprotease domain: multipotential functions in cell-cell and cell-matrix interactions," *The Journal of Cell Biol.* 131(2):275-278, 1995.

Wong et al, "Structural alterations of the epidermal growth factor receptor gene in human gliomas," *Proc. Natl. Acad. Sci. USA* (1992) 89:2965-2969.

Xu et al., "Angiopoietin-1, Unlike Angiopoietin-2, Is Incorporated into the Extracellular Matrix via its linker Peptide Region," *The Journal of Biological Chemistry* (2001) 276(37):34990-34998.

Xu et al., "Angiopoietin-3 Is Tethered on the Cell Surface via Heparan Sulfate Proteoglycans," *The Journal of Biological Chemistry* (2004) 279(39):41179-41188.

Yi et al., "A fibronectin fragment inhibits tumor growth, angiogenesis, and metastasis," *PNAS* (2001) 98(2):620-624.

Xu et al., "Angiopoietin-3 Inhibits Pulmonary Metastasis by Inhibiting Tumor Angiogenesis," Cancer Research (2004) 64:6119-6126.

Yamazaki et al., Mice with defects in HB-EGF ectodomain shedding show severe developmental abnormalities *The Journal of Cell Biology* (2003) 163(3):469-475.

Yarden et al., "Untangling the ErbB signalling network," *Nature Reviews* (2001) 2(2):127-137.

Yee et al., "Expression of the type-1 repeats of thrombospondin-1 inhibits tumor growth through activation of transforming growth factor-beta," *American Journal of Pathology* (2004) 165(2):541-552.

Yu et al., "Induction of apoptosis of metastatic mammary carcinoma cells in vivo by disruption of tumor cell surface CD44 function," *J. Exp. Med.* (1997) 186:1985-1996.

Yu et al., "Cell surface-localized matrix metalloproteinase-9 proteolytically activates TGF-beta and promotes tumor invasion and angiogenesis," *Genes & Development* (2000) 14(2):163-176.

Yu et al., "Localization of matrix metalloproteinase 9 to the cell surface provides a mechanism for CD44 mediated tumor invasion," *Genes & Development* (1999) 13(1):35-48.

Zhang et al., "Src Family Kinases Mediate Epidermal Growth Factor Receptor Ligand Cleavage, Proliferation, and Invasion of Head and Neck Cancer Cells," *Cancer Research* (2004) 64:6166-6173.

* cited by examiner

FIGURE 1, Panels A and B

FIGURE 2, Panels A through E

FIGURE 3, Panels A through D

FIGURE 4, Panels A through D

FIGURE 5, Panels A through D

FIGURE 6, Panels A through C

FIGURE 9, Panels A and B

FIGURE 10, Panels A through D

FIGURE 13, Panels A through D
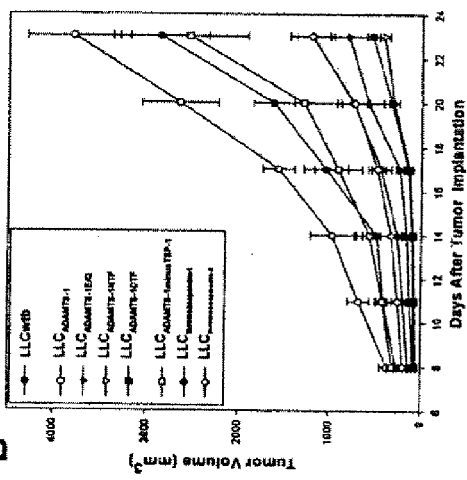
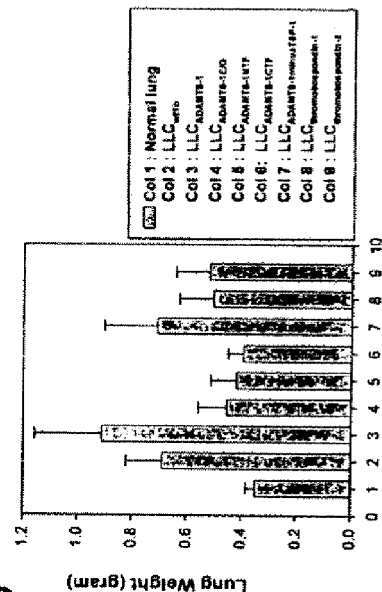
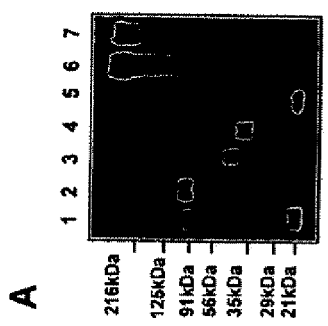
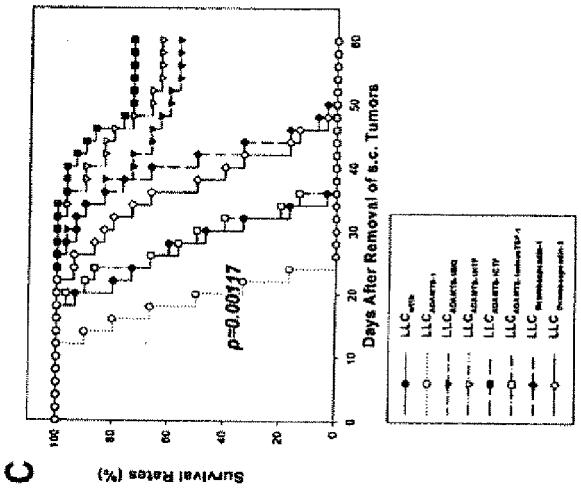

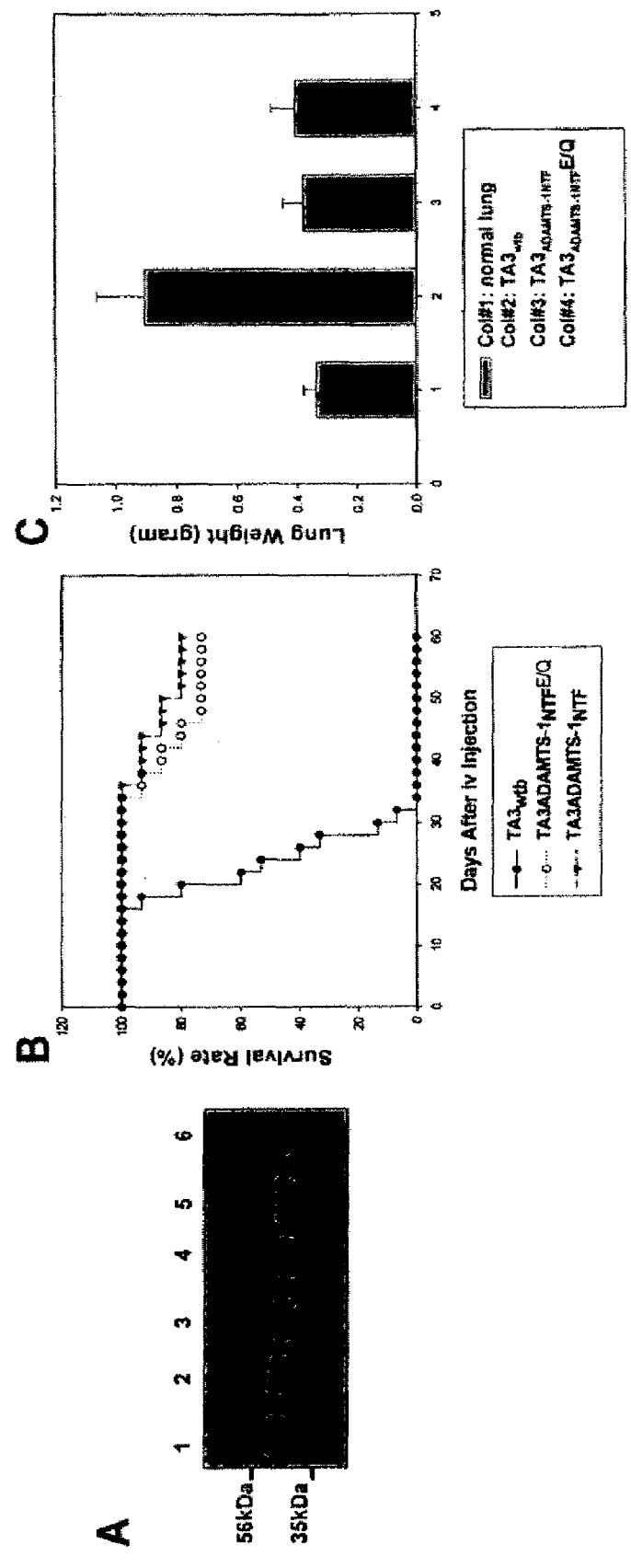
FIGURE 14, PANELS A through C

FIGURE 15

```
thrombospondin-1  1                                                              50
TSP-1 repeat-2    GGWSHW  SP  WSSCSVTCGD  GVITRIRLC  NSPSPQMNGK  PCEGEARETK  AC
                  GGWGPW  SP  WDICSVTCGG  GVQRRSRLC  NNPTPQFGGK  DCVGDVTENQ  VCNKQD
TSP-1 repeat-3    GSWGPW  GP  WGDCSRTCGG  GVQYTMREC  DNPVPKNGGK  YCEGKRVRYR  SCNIED
ADAMTS-1_m TSP-1          WVIEE  WGECSKTCGS  GWQRRVVQCR  DINGHPAS    ECAKEVKPAS  TRPCADLPCPH
ADAMTS-1_c TSP-1-1        WQVGD  WSPCSKTCGK  GYKKRTLKCV  SHDGGVLSNE  SCDPLKKPKH  YIDFCTLTQCS ADAMTS-1_c TSP-1-2
Motif:            •WXXW   XX  WXX→  _m TSP-1WXXWdel
                         •CSXTCGXX→ _m or _c TSP-1CSdel
                  •WXXXXX  WX→  _c TSP-1WXXXXWdel
                       •WGXCSKTCG→ _m or _c TSP-1WGdel
```

US 7,696,307 B2

FUNCTION AND REGULATION OF ADAMTS-1

CROSS-REFERENCE TO RELATED APPLICATIONS

This application claims priority to U.S. Provisional Application Ser. No. 60/561,429, filed Apr. 12, 2004 and U.S. Provisional Application Ser. No. 60/650,027 filed Feb. 4, 2005 each of which is herein incorporated by reference in its entirety.

GOVERNMENT SUPPORT

This invention was made with U.S. Government support (NIH Grants No. RO1HL074117) and the U.S. Government may therefore have certain rights in the invention.

REFERENCE TO SEQUENCE LISTING SUBMITTED ON COMPACT DISC

A substitute Sequence Listing is located on a separate CD-R entitled "Copy 1" in a file entitled "UPN0037100seqlist.txt," created Jun. 21, 2005, containing 124 kilobytes, and is incorporated herein by reference in its entirety. The total number of compact discs, including duplicates (i.e., "Copy 2"), submitted herewith is two, and there is one file on each of the submitted compact discs.

BACKGROUND OF THE INVENTION

The members of ADAMTS (A Disintegrin And Metalloproteinase with ThromboSpondin motifs) family belong to ADAM (A Disintegrin And Metalloproteinase) family of multifunctional proteins that display a significant sequence homology with snake venom metalloproteinases. The amino-terminal half of ADAMTS is similar to that of ADAM, which contains propeptide, metalloproteinase, disintegrin, and cysteine-rich domains; while the C-terminal half of ADAMTS is completely different and contains thrombospondin type I-like (TSP) motifs that are originally found in thrombospondin 1 and 2 and spacer region. At least 18 members of ADAMTS have been identified. ADAMTS-1 is the first member identified and is expressed in many embryonic tissues and in tumors. Disruption of ADAMTS-1 gene results in reduced growth, abnormalities in uteral, adrenal, and dipose tissues, and female infertility.

ADAMTS-1 cleaves aggrecan and versican in vitro, however, physiologic substrates of ADAMTS-1 remain to be identified. In addition, ADAMTS-1 is cleaved at the spacer region by matrix metalloproteinases (MMPs). The role of ADAMTS-1 in tumor growth and metastasis is not well established. ADAMTS-1 was found to display anti-angiogenic and anti-tumor activity, however, increased expression of ADAMTS-1 was correlated to the enhanced metastatic potential of pancreatic cancers, and studies have shown that ADAMTS-1 is one of the genes up-regulated in the breast cancer with elevated metastatic activity.

Thus, there is a need to clarify the biologic role of ADAMTS-1. Furthermore, there is a need to identify compounds and/or compositions that can be used to treat cancer or inhibit cell growth.

SUMMARY OF THE INVENTION

In some embodiments, the present invention provides isolated polypeptide fragments of ADAMTS-1 that inhibits tumor growth and metastasis.

In some embodiments, the present invention provides compositions comprising at least two different polypeptide fragment of ADAMTS-1 that inhibit cell growth and/or metastasis.

In some embodiments, the present invention provides isolated polynucleotides encoding a polypeptide fragment of ADAMTS-1 wherein the fragment inhibits metastasis In some embodiments, the present invention provides methods for identifying an inhibitor or an activator of ADAMTS-1 cleavage.

In some embodiments, the present invention provides methods for identifying a heparin inhibitor.

In some embodiments, the present invention provides methods of identifying an inhibitor of the metalloproteinase activity of ADAMTS-1.

In some embodiments, the present invention provides methods of inhibiting metastasis comprising contacting the cell with a polypeptide fragment of ADAMTS-1 that inhibits metastasis and/or a nucleic acid that encodes a polypeptide fragment of ADAMTS-1 that inhibits cell proliferation or metastasis.

In some embodiments, the present invention provides methods of treating cancer in an individual comprising administering to the individual a therapeutically effective amount of a polypeptide fragment of ADAMTS-1 and/or a nucleic acid that encodes a polypeptide fragment of ADAMTS-1 that inhibits cell proliferation or metastasis.

In some embodiments, the present invention provides methods of treating cancer comprising administering an inhibitor of the metalloproteinase activity of ADAMTS-1.

In some embodiments, the present invention provides methods of treating cancer comprising administering a therapeutically effective amount of a composition comprising a polypeptide fragment of ADAMTS-1 comprising the spacer/Cys-rich domain or the spacer domain of ADAMTS-1 or a nucleic acid molecule encoding a polypeptide fragment of ADAMTS-1 comprising the spacer/Cys-rich domain or the spacer domain of ADAMTS-1.

BRIEF DESCRIPTION OF THE FIGURES

FIG. 13, Panels A through D. Full-length ADAMTS-1 and the ADAMTS-1 fragments displayed opposite effects on growth and metastasis of LLC cells. A. The expression level of the v5-epitope tagged ADAMTS-1 (lane 1), ADAMTS-1E/Q (lane 2), ADAMTS-1$_{NTF}$ (lane 3), ADAMTS-1$_{minusTSP-1}$ (lane 4), ADAMTS-1$_{CTF}$ (lane 5), thrombospondin-1 (lane 6) and thrombospondin-2 (lane 7) by the pooled LLC transfectants. B. The growth rates of the s.c. tumors derived from the different LLC transfectants are expressed as the means of tumors volumes±SD. A total of 15 mice were used for each type of transfectants. C. Survival rates of the experimental mice after removal of the s.c. tumors derived from the different LLC transfectants. A total of thirty mice were used for each type of transfectants. D. Pulmonary metastatic burden is expressed by the average weight of the lungs derived from experimental mice three weeks after removal of the s.c. tumors.

FIG. 14, Panels A through C. The metalloproteinase activity of ADAMTS-1$_{NTF}$ is not required for its anti-tumor activity. A. The expression level of the v5-epitope tagged ADAMTS-1$_{NTF}$ (lane 1-3) and ADAMTS-1$_{NTFE/Q}$ (lane 4-6) by the TA3 transfectants. B. Survival rates of the experimental mice after iv. injection of 1×10$^6$/mouse TA3 transfectants. A total of 15 mice were used for each type of transfectants. C. Pulmonary metastatic burden is expressed by the average weight of the lungs derived from the experimental mice three weeks after the iv injection.

FIG. 15. The multiple amino acid sequence alignment of the second and third repeats of thrombospondin-1 and $_{m\ and\ c}$ TSP-1 domains in ADAMTS-1, and the deletional and peptide generation strategy in the TSP-1 domains of ADAMTS-1. The deletions and generation of three different peptides s in m and cTSP-1 domains of ADAMTS-1 are shown.

DETAILED DESCRIPTION

Figure 1:
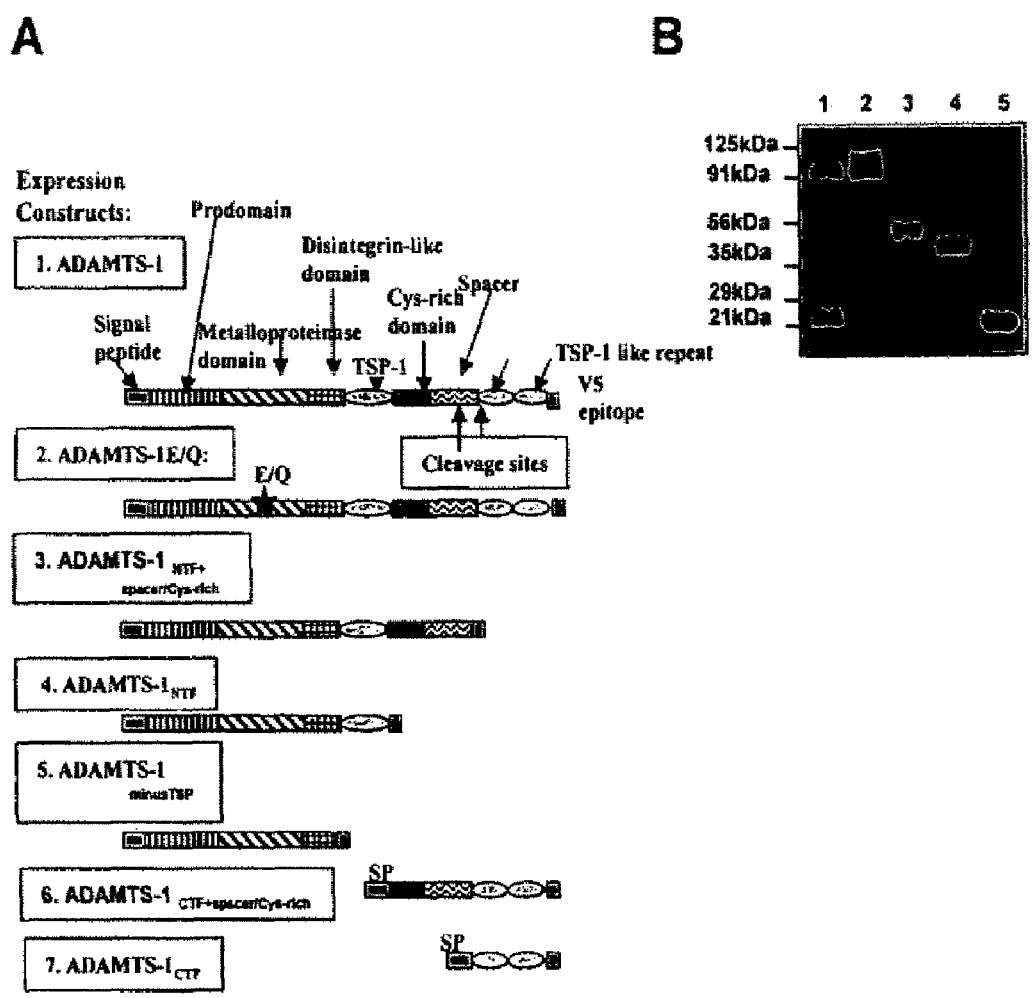
FIG. 1. ADAMTS-1 undergoes auto-proteolytic cleavage and the self cleavage of ADAMTS-1 is regulated. A. Diagram of the expression constructs. B. Cleavage of ADAMTS-1 is blocked by heparin and HS. TA3$_{ADAMTS-1}$ cells were cultured in the absence (lane 1) or presence of 100 µg/ml of heparin (lane 2), HS (lane 3), hyaluronan (lane 4), or CS (lane 5) for 48 hours and the cell culture supernatants were analyzed by Western blot with anti-v5 antibody.

In the present invention it has been discovered that ADAMTS-1 is expressed by many tumor cells and overexpression of ADAMTS-1 promotes growth and metastasis of TA3 mammary carcinoma cells by promoting survival, proliferation, invasiveness of the tumor cells and tumor angiogenesis in vivo. Additionally, disclosed herein is that ADAMTS-1 undergoes auto-proteolytic cleavage to generate N- and C-terminal cleavage fragments that contain at least one TSP type I motif. Auto-proteolytic cleavage of ADAMTS-1 is blocked by heparin and heparin sulfate (HS). Although not bound by any theory, this indicates that the self-cleavage is regulated by HS and heparin sulfate proteoglycans (HSPGs). Thus, as described herein, ADAMTS-1 expressed by TA3 cells is maintained in the full-length form in vivo to exert pro-tumor growth and metastasis activity. In contrast to the full-length ADAMTS-1, overexpression of the N- or C-terminal fragment of ADAMTS-1 (ADAMTS-1$_{NTCF}$ and/or ADAMTS-1$_{CTCF}$) inhibits subcutaneous (s.c.) growth of TA3 cells and blocks pulmonary metastasis of the cells by inhibiting proliferation and inducing apoptosis of the tumor cells and by inhibiting tumor angiogenesis. Additionally, the anti-tumor effect of the ADAMTS-1 fragments requires a TSP type-I motif. The direct evidence was provided for the first time that ADAMTS-1 promotes tumor growth and metastasis, and can serve as a target for cancer therapy.

For the first time, it has been demonstrated that unlike full-length ADAMTS-1 which promotes shedding of the EGF family ligands including amphiregulin (AR) and heparin-binding EGF (HB-EGF) and activation of EGF receptor (EGFR) and ErbB-2, the cleavage fragments of ADAMTS-1 inhibits activation of EGFR and ErbB-2 in vivo, and interferes with Erk1/2 kinases activation induced by soluble AR. HB-EGF, and/or VEGF in mammary epithelial cells and endothelial cells. These different effects likely underlie the opposite roles of ADAMTS-1 and its cleavage fragments in tumor growth and metastasis, suggesting the ADAMTS-1 fragments and the inhibitors of ADAMTS-1 can be most successfully used to treat the cancers overexpressing these heparin binding growth and angiogenic factors and with activated erbB-signaling pathways.

The term "ADAMTS-1$_{NTCF}$" can also be referred to as "ADAMTS-1$_{NTF}$". The term "ADAMTS-1$_{CTCF}$" can also be referred to as "ADAMTS-1$_{CTF}$". In some embodiments, ADAMTS-1$_{NTCF}$ comprises SEQ ID NO: 9 and/or 11. In some embodiments, ADAMTS-1$_{CTCF}$ comprises SEQ ID NO: 5 and/or 7.

The discovery that ADAMTS-1 can be cleaved into at least two fragments has led to the following invention. In some embodiments, the present invention provides an isolated polypeptide comprising a fragment of ADAMTS-1 that inhibits cell growth or cell survival and/or metastasis.

As used herein, the term "isolated polypeptide fragment" refers to a polypeptide fragment that is free of the full length protein. In some embodiments, the isolated polypeptide is also free of nucleic acid molecules. In some embodiments, the isolated polypeptide is free of cellular membranes. In some embodiments, the isolated polypeptide has been purified away from cellular components. In some embodiments, the polypeptide comprises a fragment of SEQ ID NO: 1 and/or SEQ ID NO: 3. In some embodiments, the fragment of ADAMTS-1 comprises SEQ ID NO: 5, 7, 9, and/or 11. The fragment of ADAMTS-1 can be any length such that it is not the full-length ADAMTS-1 protein. In some embodiments, the fragment comprises about 100 to about 150, about 100 to about 200, about 100 to about 300, about 100 to about 400, about 100 to about 500, about 100 to about 600, about 100 to about 700, about 100 to about 800, about 100 to about 900, or about 100 to about 950 amino acid residues. In some embodiments, the fragments of ADAMTS-1 comprise modifications of the polypeptide sequence. The modification can be any modification including, but not limited to, mutations, insertions, substitutions, deletions, and the like. In some embodiments, the fragment comprises a mutation of Glu to Gln. In some embodiments, the mutation of Glu to Gln occurs at a position corresponding to position 386 (in mouse ADAMTS-1) in the full length protein. One of skill in the art can determine what position in a fragment corresponds to position 386 in the full length protein (e.g. position 385 in human ADAMTS-1). One of skill in the art can do this by, for example, performing an alignment using any alignment software or BLAST software using default settings. Examples of software that can be used include, but are not limited to, BLAST, GCG, and MacVector™. In some embodiments, the polypeptide fragment containing a mutation comprises SEQ ID NO: 33 and/or 35 or a nucleic acid molecule encoding the same. In some embodiments, the nucleic acid molecule encoding the fragment comprises SEQ ID NOs: 34 and/or 36.

In some embodiments the fragments of ADAMTS-1 are linked to a non-ADAMTS-1 molecule. In some embodiments, the non-ADAMTS-1 molecule is a toxin, peptide, polypeptide, small molecule, drug, and the like. In some embodiments, the non-ADAMTS-1 molecule is a 6-His-tag, GST polypeptide, HA tag, the Fc fragment of human IgG and the like. In some embodiments, the proteinase cleavage sites will be put before the tag sequences, so that after purification these tags can be removed by proteolytic cleavage. For example, the HRV 3C (human rhinovirus type 14 3C) protease cleavage site (LEVLFQ↓GP) can be located before the COOH-terminal v5 and His epitope tags. The HRV 3C protease specifically claves the sequence LEVLFQ↓GP at 40C and were used to efficiently removal the COOH-terminal tags (Novagen).

In some embodiments, the fragment of ADAMTS-1 is fused to another polypeptide that is derived from a protein that is not ADAMTS-1. In some embodiments two fragments from ADAMTS-1 are fused or linked together. In some embodiments, the two fragments are identical. In some embodiments, the fragments are different from one another. The fragments that can be linked or fused together are ADAMTS-1$_{CTCF}$ (SEQ ID NO: 5 and/or SEQ ID NO:7), ADAMTS-1$_{NTCF}$ (SEQ ID NO: 9 and/or 11), and ADAMTS-1$_{spacer}$ or ADAMTS-1$_{spacer/Cys-rich}$ to achieve maximal antitumor efficiency, however any two fragments from ADAMTS-1 can be fused together.

In some embodiments, the present invention provides nucleic acid molecules encoding a fragments of ADAMTS-1. In some embodiments, the fragments of ADAMTS-1 that inhibits cell proliferation or metastasis comprise a TSP type-I motif.

A fragment that inhibits cell proliferation or metastasis can also be referred to as a fragment that inhibits cancer or a fragment can be used to treat cancer.

As used herein, the term "inhibit cell proliferation" refers to any measurement of cell proliferation. A fragment, compound, or composition that causes a cell to undergo necrosis or apoptosis is considered to inhibit cell proliferation. Cell proliferation can also be referred to as cell growth or cell division.

Methods of measuring cell proliferation, division, and metastasis are routine and any method can be used.

For example, one can measure cell invasion using Matrigel in vitro. Metastasis can also be measured and/or observed in vivo by injecting a mouse with a tumor cell and determining if the cell spreads to a different location away from the sight of injection. Metastasis can also be measured by measuring or observing tumor burden or tumor growth in areas that are distinct from the primary tumor location. Cell proliferation can be measured, for example, by counting cells. Cell division can be measured, for example, by monitoring what phase of the cell cycle a cell or a population of cells is in by using flow cytometry or FACS. Determining if a cell or cell population is dividing is routine.

In some embodiments, the present invention provides a fragment of ADAMTS-1 that lacks a TSP motif. In some embodiments, the present invention provides a deletion of ADAMTS-1 that lacks a TSP motif. In some embodiments, a polypeptide of ADAMTS-1 that lacks a TSP motif comprises SEQ ID NO:13 and/or SEQ ID NO:15. The term "ADAMTS-1$_{minus\ TSP}$" can also be referred to as "ADAMTS-1$_{minus\ TSP-1}$". In some embodiments, the present invention provides a nucleic acid molecule that encodes for a ADAMTS-1polypeptide that lacks a TSP motif. In some embodiments the nucleic acid molecule is isolated. In some embodiments the nucleic acid molecule comprises SEQ ID NO: 14 and/or SEQ ID NO: 16.

In some embodiments, the present invention provides an isolated nucleic acid molecule (polynucleotide) encoding a polypeptide fragment of ADAMTS-1.

As used herein the term "isolated nucleic acid molecule encoding a polypeptide fragment of ADAMTS-1" refers to a nucleic acid molecule is free of a nucleic acid molecule encoding full length ADAMTS-1.

In some embodiments, a fragment encoded by the nucleic acid molecule can inhibit cell proliferation and/or metastasis. In some embodiments, the nucleic acid molecule comprises a fragment of a nucleic acid molecule encoding a polypeptide comprising SEQ ID NO:1 and/or SEQ ID NO: 2. In some embodiments the nucleic acid molecule comprises a fragment of SEQ ID NO: 3 and/or SEQ ID NO: 4 In some embodiments, the nucleic acid molecule encodes a polypeptide comprising SEQ ID NOs: 5, 7, 9, and/or 11. In some embodiments, the nucleic acid molecule comprises SEQ ID NOs: 6, 8, 10, and/or 12. In some embodiments, the nucleic acid molecule encoding a fragment of ADAMTS-1 is operably linked to a promoter. In some embodiments, the promoter can facilitate the expression in a prokaryotic cell and/or eukaryotic cell. The promoter can be any promoter that can drive the expression of the nucleic acid molecule. Examples of promoters include, but are not limited to, CMV, SV40, pEF, actin promoter, and the like. In some embodiments, the nucleic acid molecule is DNA or RNA. In some embodiments, the nucleic acid molecule is a virus, vector, or plasmid. In some embodiments, the expression of the nucleic acid molecule is regulated such that it can be turned on or off based on the presence or absence of a regulatory substance. Examples of such a system include, but is not limited to a tetracycline-ON/OFF system.

In some embodiments, the nucleic acid molecule is a recombinant viral vector. "A recombinant viral vector" refers to a construct, based upon the genome of a virus, that can be used as a vehicle for the delivery of nucleic acids encoding proteins, polypeptides, or peptides of interest. Recombinant viral vectors are well known in the art and are widely reported. Recombinant viral vectors include, but are not limited to, retroviral vectors, adenovirus vectors, adeno-associated virus vectors, and lenti-virus vectors, which are prepared using routine methods and starting materials.

Using standard techniques and readily available starting materials, a nucleic acid molecule may be prepared. The nucleic acid molecule may be incorporated into an expression vector which is then incorporated into a host cell. Host cells for use in well known recombinant expression systems for production of proteins are well known and readily available. Examples of host cells include bacteria cells such as E. coli, yeast cells such as S. cerevisiae, insect cells such as S. frugiperda, non-human mammalian tissue culture cells Chinese hamster ovary (CHO) cells or Cos-7 cells, and human tissue culture cells such as 293 cells or HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of immunomodulating proteins in E. coli. The commercially available plasmid pYES2 (Invitrogen, San Diego, Calif.) may, for example, be used for production in S. cerevisiae strains of yeast. The commercially available MAXBAC™ complete baculovirus expression system (Invitrogen, San Diego, Calif.) may, for example, be used for production in insect cells. The commercially available plasmid pcDNAI, pcDNA3, or PEF6/v5-His (Invitrogen, San Diego, Calif.) may, for example, be used for production in mammalian cells such as Cos-7 and CHO cells. One having ordinary skill in the art can use these commercial expression vectors and systems or others to produce proteins by routine techniques and readily available starting materials. (See e.g., Sambrook et al., eds., 2001, supra) Thus, the desired proteins or fragments can be prepared in both prokaryotic and eukaryotic systems, resulting in a spectrum of processed forms of the protein or fragments.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts (See e.g., Sambrook et al., eds., 2001, supra).

In some embodiments, the nucleic acid molecules can also be prepared as a genetic construct. "Genetic constructs" include regulatory elements necessary for gene expression of a nucleic acid molecule. The elements include: a promoter, an initiation codon, a stop codon, and a polyadenylation signal. In addition, enhancers can be used for gene expression of the sequence that encodes the protein or fragment. It is necessary that these elements be operably linked to the sequence that encodes the desired polypeptide and that the regulatory elements are operably in the individual or cell to whom they are administered. Initiation codons and stop codon are generally considered to be part of a nucleotide sequence that encodes the desired protein. However, it is necessary that these elements are functional in the individual or cell to which the gene construct is administered. The initiation and termination codons must be in frame with the coding sequence. Promoters and polyadenylation signals used must be functional within the cells. Examples of promoters useful to practice the present invention include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein. Examples of polyadenylation signals useful to practice the present invention include but are not limited to SV40 polyadenylation signals and LTR polyadenylation signals. In some embodiments, the SV40 polyadenylation signal which is inpCEP4 plasmid (Invitrogen, San Diego Calif.), referred to as the SV40 polyadenylation signal, is used. In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV. Genetic constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration. In some embodiments, the nucleic acid molecule is free of infectious particles.

In some embodiments, the present invention provides compositions comprising at least one polypeptide fragment of ADAMTS-1 that inhibits cell proliferation or cell growth or metastasis. In some embodiments, the composition comprises a fragment comprising SEQ ID NO:1 and/or SEQ ID NO:2. In some embodiments, the composition comprises a fragment comprising SEQ ID NO:5, SEQ ID NO:7, SEQ ID NO: 9, and/or SEQ ID NO: 11. In some embodiments, the composition comprises two or at least two polypeptide fragments of ADAMTS-1. In some embodiments, the fragment comprises the TSP-type I motif. In some embodiments, the composition is a pharmaceutical composition.

As used herein, the term "fragment of ADAMTS-1 that inhibits cell proliferation or metastasis" refers to a fragment of ADAMTS-1 that can inhibit cell growth, cell division, or cell proliferation. In some embodiments, the fragment inhibits cell growth, cell division, cell proliferation, or metastasis by 10%, 20%, 30%, 40%, 50%, 60%, 70%, 80%, 90%, 95%, or 100%. In some embodiments, the fragment can inhibit cell growth, cell division, cell proliferation, or metastasis by at least 10%, at least 20%, at least 30%, at least 40%, at least 50%, at least 60%, at least 70%, at least 80%, at least 90%, at least 95%, or at least 99%. One of skill in the art can determine the level of inhibition by, for example, comparing the property or properties of the cell or population of cells in the absence of the fragment.

A fragment of ADAMTS-1 that inhibits cell proliferation, cell growth, cell division, or metastasis can be identified using any known growth, proliferation, or division assay. For example, one of skill in the art can contact a fragment of ADAMTS-1 with a cell either in vitro or in vivo and determine whether the cell's growth, proliferation, divisions, or metastasis have been inhibited. One of skill in the art could also use a nucleic acid molecule encoding a fragment of ADAMTS-1 and introduce the nucleic acid molecule into a cell or organism such that the fragment is expressed. The cell's or population of cell's property or properties could then be measured and it could be determined whether the fragment encoded by the nucleic acid molecule can inhibit cell growth (proliferation), cell division, or metastasis.

The fragments of ADAMTS-1 that can be used to inhibit cell proliferation or growth can be produced by a cleavage event of ADAMTS-1. In some embodiments, the cleavage produces fragments of ADAMTS-1 comprising SEQ ID NOs: 5, 7, 9 and/or 11 or encoded by nucleic acid molecules comprising SEQ ID NO: 6, 8, 10, and/or 12.

In some embodiments, the present invention provides methods of inhibiting the cleavage of ADAMTS-1 in a cell comprising contacting the cell with a cleavage inhibiting factor. A "cleavage inhibiting factor" is a compound or composition that can inhibit the cleavage of ADAMTS-1. In some embodiments, the cleavage of ADAMTS-1 is auto-cleavage or cleavage that is facilitated by a protease that is not ADAMTS-1. In some embodiments, the cleavage inhibiting factor is heparin or heparan sulfate proteoglycans (HSPGs). Heparin or derivatives of heparin were found to inhibit the cleavage of ADAMTS-1 as described herein. In some embodiments, the present invention provides methods of promoting cleavage of ADAMTS-1 comprising contacting ADAMTS-1 with a ADAMTS-1 cleavage activating factor. In some embodiments, the cleavage activating factor is a compound that inhibits and/or sequesters heparin. In some embodiments, the factor that inhibits heparin is heparinase, platelet factor 4 (PF4-a), protamine, or polybrene. A "cleavage activating factor" is a compound or composition that enhances, induces, or increases the level of cleavage of ADAMTS-1. In some embodiments, the cleavage of ADAMTS-1 can be auto-cleavage. In some embodiments, the cleavage of ADAMTS-1 can be facilitated by a protease that is not ADAMTS-1.

In some embodiments, the present invention provides methods of inhibiting cell proliferation or metastasis comprising contacting the cell with a fragment of ADAMTS-1 that inhibits cell proliferation or metastasis. In some embodiments, the fragment of ADAMTS-1 comprises a fragment of SEQ ID NO: 1 and/or SEQ ID NO:3. In some embodiments, the fragment comprises SEQ ID NOs: 5, 7, 9 and/or 11. One of skill in the art can determine if the fragment inhibits cell proliferation or metastasis of a cell or population of cells by measuring the growth or metastasis in the presence and/or absence of the fragment of ADAMTS-1.

As used herein, the term "cell" refers to any cell. In some embodiments, the cell is a human cell or a mouse cell. In some embodiments, the cell is a tumor cell, inflammatory cells, or keratinocytes. In some embodiments, the cell is a primary tumor cell. As used herein, the term "primary tumor cell" refers to a cell that has been excised from a tumor from an individual or animal and has not been propagated through more than 10 cell divisions.

The discovery that fragments of ADAMTS-1 can inhibit cell growth and/or metastasis demonstrates that in some embodiments, the present invention provides methods of treating cancer in an individual comprising administering to the individual a therapeutically effective amount of a fragment of ADAMTS-1 that is able to inhibit cell proliferation or metastasis. The fragments can also be said to inhibit tumor growth and the like. In some embodiments, the fragment comprises a fragment of SEQ ID NO: 1 and/or SEQ ID NO: 3. In some embodiments, the fragment comprises SEQ ID NOs: 5, 7, 9 and/or 11. In some embodiments, the fragment of ADAMTS-1 is co-administered with at least one other cancer treatment. The fragment of ADAMTS-1 can be either administered prior to, subsequently to, or at the same time as the other cancer treatment. The fragment(s) of ADAMTS-1 can be co-administered with any other cancer treatment, including, but not limited to, surgery, chemotherapy, antibodies, small molecules, radiation, and the like. In some embodiments, the fragment of ADAMTS-1 that is used to treat the cancer in an individual is a fragment of ADAMTS-1 that is able to inhibit cell proliferation, metastasis, or angiogenesis. In some embodiments, the fragment inhibits cell proliferation and/or metastasis in vitro.

Since it has been discovered that the full length ADAMTS-1 is pro-cancer while the cleavage fragments of ADAMTS-1 have anti-cancer properties, the present invention provides methods of treating cancer in an individual comprising administering to the individual a composition that induces the cleavage of ADAMTS-1. In some embodiments, the composition that induces the cleavage of ADAMTS-1 is a heparin inhibitor. Examples of heparin inhibitors include, but are not limited to, heparinase, platelet factor 4 (PF4-a), protamine, polybrene, the heparin-binding domain/peptide derived from HSPGs, and the like. In some embodiments, the cleavage of ADAMTS-1 results in the production of at least one fragment of ADAMTS-1 that can inhibit cell proliferation or metastasis. In some embodiments, the cleavage of ADAMTS-1 results in the production of two or at least two fragments of ADAMTS-1 that can inhibit cell proliferation or metastasis. In some embodiments, the fragments that are produced by the cleavage of ADAMTS-1 comprise SEQ ID NOs: 5, 7, 9 and/or 11.

In some embodiments, the present invention provides methods of inhibiting metastasis in an individual comprising administering the individual a fragment or mutant of ADAMTS-1 that inhibits metastasis and/or angiogenesis. In some embodiments, the mutant of ADAMTS-1 is a metalloproteinase defective mutant. In some embodiments, the fragment of ADAMTS-1 that inhibits metastasis comprises SEQ ID NO: 5, 7, 9, and/or 11. In some embodiments, the fragment or mutant of ADAMTS-1 that inhibits metastasis, cell growth or proliferation and/or angiogenesis comprises SEQ ID NO: 5, 7, 9, 11, 17, 19, 21, 23, 25, 27, 29, 31, 33, and/or 35.

In some embodiments, a method of treating cancer can refer to a method of inhibiting cell growth, division, inducing cell death (e.g. apoptosis and/or necrosis), promoting metastasis and angiogenesis, or combinations thereof.

The fragments or mutants of the present invention can also be administered in the form of a nucleic acid molecule that encodes for the fragments or for the mutants. In some embodiments, the nucleic acid molecule comprises SEQ ID NO: 6, 8, 10, 12, 14, 16, 18, 20, 22, 24, 26, 28, 30, 32, 34, and/or 36.

The present invention also provides antibodies or fragments of antibodies that can specifically bind to and block the pro-cancer activity of ADAMTS-1. In some embodiments, the antibody specifically binds to ADAMTS-1 comprising SEQ ID NO: 1, 2, 3, or 4

As used herein, the term "specifically binds to" in reference to an antibody refers to an antibody that will bind to one peptide or protein with higher affinity than another peptide. In some embodiments, the antibody that specifically binds to a peptide or polypeptide will not bind to more than one peptide. In some embodiments, the specific antibody binds with a Kd that is 10×, 100×, 1000× greater to one peptide over another. Methods of making and identifying specific antibodies are routine.

The present invention also provides for antibodies that binds to full-length ADAMTS-1 to inhibit cell proliferation, division, growth, or metastasis. In some embodiments, the polypeptide comprises SEQ ID NO: 1, 2, 3, or 4.

The present invention also provides methods of inducing the cleavage of ADAMTS-1 in a cell comprising contacting the cell with a heparin inhibitor. Examples of heparin inhibitors include, but are not limited to heparinase, platelet factor 4 (PF4-a), protamine, polybrene, and the like.

The present invention also provides for methods for identifying an inhibitor or an activator of ADAMTS-1 cleavage comprising performing a test assay comprising contacting ADAMTS-1 with a test compound; and measuring the cleavage of ADAMTS-1, wherein a decrease in cleavage indicates that the test compound is a cleavage inhibitor or wherein an increase in cleavage indicates that the test compound is a cleavage activator. In some embodiments, the effect of the test compound is compared what occurs in the absence of any test compound. In some embodiments, the compound is contacted with ADAMTS-1 under conditions in which ADAMTS-1 is cleaved. In some embodiments, ADAMTS-1 undergoes auto-cleavage (e.g. where the enzyme cleaves itself). In some embodiments, the method comprising contacting a test compound with ADAMTS-1 under conditions where ADAMTS-1 can be cleaved. These conditions can be any conditions and can be modified such that ADAMTS-1 is able to be cleaved either by itself (auto-cleavage) or by another molecule. Conditions that can be modified include, but are not limited to, pH, ion concentration, metal concentration, and the like.

In some embodiments the methods comprise contacting more than one test compound, in parallel. In some embodiments, the methods comprises contacting 2, 3, 4, 5, 6, 7, 8, 9, 10, 15, 20, 25, 30, 40, 50, 100, 1000, at least 2, at least 5, at least 10, at least 50, at least 100, or at least 1000 test compounds in parallel. In some embodiments, the present invention is used in High Throughput Screening of compounds and complete combinatorial libraries can be assayed, e.g., up to thousands of compounds. Methods of how to perform high throughput screenings are well known in the art. The methods can also be automated such that a robot can perform the experiments. The present invention can be adapted for the screening of large numbers of compounds, such as combinatorial libraries of compounds. Indeed, compositions and methods allowing efficient and simple screening of several compounds in short periods of time are provided. The instant methods can be partially or completely automated, thereby allowing efficient and simultaneous screening of large sets of compounds.

In some embodiments, the method of the present invention comprises the step of contacting a cell expressing v5-epitope tagged ADAMTS-1 (such as TA3$_{ADAMTS-1}$) in the presence of a test compound. The cells can be observed to determine if the test compound inhibits or promotes the cleavage of ADAMTS-1. A control may be provided in which the cell is not contacted with a test compound. A further control may be provided in which test compound is contacted with cells that either do not express ADAMTS-1 or in which ADAMTS-1 cannot be cleaved (the cleavage-resistant ADAMTS-1 mutant). If the cells contacted with the test compound increase the cleavage of ADAMTS-1 then pro-cleavage activity is indicated for the test compound. If the cells contacted with the test compound decrease the cleavage of ADAMTS-1 then anti-cleavage activity is indicated for the test compound.

Positive and negative controls may be performed in which known amounts of test compound and no compound, respectively, are added to the assay. One skilled in the art would have the necessary knowledge to perform the appropriate controls.

The test compound can be any product in isolated form or in mixture with any other material (e.g., any other product(s)). The compound may be defined in terms of structure and/or composition, or it may be undefined. For instance, the compound may be an isolated and structurally-defined product, an isolated product of unknown structure, a mixture of several known and characterized products or an undefined composition comprising one or several products. Examples of such undefined compositions include for instance tissue samples, biological fluids, cell supernatants, vegetal preparations, etc. The test compound may be any organic or inorganic product, including a polypeptide (or a protein or peptide), a nucleic acid, a lipid, a polysaccharide, a chemical product, or any mixture or derivatives thereof. The compounds may be of natural origin or synthetic origin, including libraries of compounds.

In some embodiments, the activity of the test compound(s) is unknown, and the method of this invention is used to identify compounds exhibiting the selected property (e.g., ADAMTS-1 cleavage). However, in some embodiments instances where the activity (or type of activity) of the test compound(s) is known or expected, the method can be used to further characterize the activity (in terms of specificity, efficacy, etc.) and/or to optimize the activity, by assaying derivatives of the test compounds.

The amount (or concentration) of test compound can be adjusted by the user, depending on the type of compound (its toxicity, cell penetration capacity, etc.), the number of cells, the length of incubation period, the amount of ADAMTS-1, etc. In some embodiments, the compound can be contacted in the presence of an agent that facilitates penetration or contact with a cell comprising ADAMTS-1. The test compound is provided, in some embodiments, in solution. Serial dilutions of test compounds may be used in a series of assays. In some embodiments, test compound(s) may be added at concentrations from 0.01 μM to 1M. In some embodiments, a range of final concentrations of a test compound is from 10 μM to 100 μM. One such test compound that is effective to activate cleavage of ADAMTS-1 in a cell is a heparin inhibitor.

In some embodiments, the method comprises measuring ADAMTS-1 cleavage in the presence of the test compound. If the test compound is found to cleave ADAMTS-1 it is indicative that the test compound is pro-cleavage ADAMTS-1 agent. Since the cleavage fragments of ADAMTS-1 agent, a pro-cleavage fragment can also be considered an anti-cancer agent.

ADAMTS-1 cleavage can be measured by any means that demonstrates that the cleavage of ADAMTS-1 has been modulated (increased or decreased) in the presence of the test compound. Examples of how to measure ADAMTS-1 cleavage include measuring an increase or decrease in the cleavage fragments of ADAMTS-1. The cleavage fragments can be measured by any means including, but not limited to, Western Blot, ELISA, Sandwich Assay, and the like. Methods of measuring the levels protein cleavage fragments are routine to one of ordinary skill in the art.

In some embodiments, the test compound activates the cleavage of ADAMTS-1 by at least 10%, at least 20%, at least 30%, at least 40%, at least 50%, at least 60%, at least 70%, at least 80%, at least 90%, at least 100%, at least 200%. In some embodiments, the test compound inhibits the cleavage of ADAMTS-1 by at least 10%, at least 20%, at least 30%, at least 40%, at least 50%, at least 60%, at least 70%, at least 80%, at least 90%, or at least 99%. In some embodiments, the cleavage of ADAMTS-1 is compared to cleavage of ADAMTS-1 observed in the absence of the test compound.

In some embodiments, the methods further comprise performing a control assay. In some embodiments, the control assay comprising contacting a cell with a negative or positive control and measuring, including, but not limited to, ADAMTS-1 cleavage. In some embodiments, the control compound is compared to the test compound. In some embodiments, the control compound is a negative control (e.g. a compound that does not inhibit or activate ADAMTS-1 cleavage). A negative control can also be the absence of a test compound or the vehicle (e.g. solvent) that the test compound is contacted with the cell. In some embodiments, the control compound is a positive control (e.g. a compound that inhibits or activates ADAMTS-1 cleavage).

In some embodiments, the test compound is a small molecule, a peptide (including the peptides from the heparin-binding proteins and HSPGs), an antibody, a cellular fraction, a protease, or a mixture thereof. As discussed above, the test compound can be contacted with a cell comprising ADAMTS-1, but the test compound can be contacted with ADAMTS-1. For example, ADAMTS-1 can be expressed as a protein and either be purified or not be purified, but is isolated from a cell. For the purposes of the screening assays to identify test compounds that can inhibit or activate the cleavage of ADAMTS-1, an isolated protein is a protein that is separated from a cell. The protein can be purified from other components in the cell, but it does not have to be. In some embodiments, an isolated ADAMTS-1 protein results from a cell being lysed which releases all the contents of the cell. The cleavage of ADAMTS-1 can then be measured or monitored in a non-cellular environment. The test compound is then contacted with ADAMTS-1 to determine if the test compound can inhibit or activate the cleavage of ADAMTS-1.

In some embodiments, the methods further comprise performing a negative Control assay which comprises contacting a cell that does not comprise ADAMTS-1 or a cell that comprises a cleavage resistant mutant of ADAMTS-1. In some embodiments, the negative control assay comprises contacting an isolated cleavage resistant mutant of ADAMTS-1.

The present invention also provides methods for identifying an anti-cancer agent comprising performing a test assay comprising contacting a cell comprising ADAMTS-1 with a test compound; and measuring the cleavage of ADAMTS-1, wherein an increase in cleavage indicates that the test compound is an anti-cancer compound. In some embodiments, the cleavage in the presence of the test compound is compared to an assay where the cell is comprising ADAMTS-1 is not contacted with the test compound.

As used herein, "a cell comprising ADAMTS-1" refers to a cell expressing the protein ADAMTS-1. The cell can be either be expressing the protein endogenously (e.g. from within its native genome) or exogenously. An exogenously expressed protein is a protein in a cell that would not normally be present except for some modification. The exogenously expressed protein can be, for example, transfected into a cell either stably or transiently.

The present invention also provides methods of inhibiting angiogenesis in an individual comprising administering to the individual a fragment of ADAMTS-1. In some embodiments, the fragment of ADAMTS-1 comprises ADAMTS-1$_{CTCF}$ or ADAMTS-1$_{NTCF}$ (SEQ ID NOs: 5, 7, 9 and/or 11). In some embodiments a nucleic acid molecule encoding the fragments is administered. In some embodiments, the nucleic acid molecule comprises SEQ ID NOs: 6, 8, 10, and/or 12.

The present invention provides methods of inhibiting the growth or metastasis of a tumor. In some embodiments, the tumor is vascularized or non-vascularized.

The present invention also provides methods of treating cancer comprising inhibiting the metalloproteinase activity of ADAMTS-1. In some embodiments, the metalloproteinase activity of ADAMTS-1 is inhibited by administering a metalloproteinase defective full-length ADAMTS-1 or the ADAMTS-1 fragments containing its substrate-binding domain such as ADAMTS-1$_{spacer/Cys-rich}$ or ADAMTS-1$_{spacer}$, which can act as the dominant negative mutants of ADAMTS-1 and inhibit the activity of the wild-type protein. In some embodiments, the metalloproteinase defective ADAMTS-1 comprises SEQ ID NO: 29, 31, 33, and/or 35. In some embodiments, the metalloproteinase activity is inhibited by an antibody or a small molecule that binds to ADAMTS-1. In some embodiments, the metalloproteinase activity is inhibited by an antibody or a small molecule that binds to the metalloproteinase active site of ADAMTS-1.

The present invention also provides methods of identifying inhibitors of ADAMTS-1 metalloproteinase activity comprising contacting a fragment of or full-length ADAMTS-1 that has metalloproteinase activity with a test compound and determining if the metalloproteinase activity is inhibited. (In some embodiments, the fragment of ADAMTS-1 comprises SEQ ID NO: 5, 7, 9, and/or 11.) In some embodiments, the activity in the presence of the test compound is compared to the activity in the absence of the test compound. In some embodiments, the method comprises comparing the activity with a positive control assay and/or a negative control assay. In some embodiments, the method comprises comparing the activity of the fragment to a fragment that is defective in metalloproteinase activity. A fragment can be defective in metalloproteinase because of a mutation, substitution, deletion, or insertion. In some embodiments, the fragment is defective in metalloproteinase activity due to a Glu to Gln mutation. In some embodiments, the fragment that lacks metalloproteinase activity comprises SEQ ID NO: 33 and/or 35. In some embodiments, the fragment that lacks metalloproteinase activity is encoded by a nucleic acid molecule comprising SEQ ID NO: 34 and/or 36.

Methods of measuring metalloproteinase activity (e.g. ADAMTS-1 activity) are routine. For example, the cleavage of substrates of ADAMTS-1 can be measured and compared in the absence and presence of a test compound. However, any method or means can be used to measure metalloproteinase activity of ADAMTS-1. Substrates of ADAMTS-1 are known in the art and can be measured. In some embodiments, the substrate of the metalloproteinase is aggrecan or versican.

In some embodiments, the present invention provides methods of treating cancer comprising administering to an individual a compound that is a ADAMTS-1 metalloproteinase activity inhibitor. In some embodiments, the inhibitor is a dominant negative mutant of ADAMTS-1. In some embodiments, the inhibitor is a polypeptide or comprising SEQ ID NO: 33 and/or 35. In some embodiments, the inhibitor is encoded by a nucleic acid molecule comprising SEQ ID NO: 34 and/or 36.

Other fragments or mutants of ADAMTS-1 can also be used to treat cancer because they also act as a dominant negative regulator of ADAMTS-1 and, thus, be able to inhibit the function of ADAMTS-1. Accordingly, the present invention provides methods of treating cancer comprising administering a therapeutically effective amount of a composition comprising a fragment of ADAMTS-1 comprising the spacer/Cys-rich and/or Spacer domain of ADAMTS-1.

The present invention also provides polypeptide fragments of ADAMTS-1 comprising the spacer/Cys-rich and/or spacer domain of ADAMTS-1. In some embodiments, the fragment comprises SEQ ID NO: 17, 19, 21, and/or 23. In some embodiments, the fragments are encoded by nucleic acid molecules comprising 18, 20, 22, and/or 24.

The present invention also provides for fragments of ADAMTS-1 that bind to the extracellular matrix (ECM). According, in some embodiments, the present invention provides an ECM binding fragment of ADAMTS-1. An "ECM binding fragment of ADAMTS-1" is a fragment of ADAMTS-1 that binds to the ECM. In some embodiments, the ECM binding fragment of ADAMTS-1 comprises SEQ ID NO: 17, 19, 21, and/or 23. In some embodiments, a nucleic acid molecule encodes for an ECM binding fragment of ADAMTS-1. In some embodiments, the ECM binding fragment comprises SEQ ID NO: 18, 20, 22, and/or 24.

In some embodiments, the present invention provides nucleic acid molecules encoding any fragment of ADAMTS-1 described herein. In some embodiments, the nucleic acid molecule comprises SEQ ID NOs: 2, 4, 6, 8, 10, 12, 14, 16, 18, 20, 22, 24, 16, 28, 30, 32, 34, 36, or combinations thereof.

In some embodiments, the present inventions provides polypeptides comprising at least a fragment of ADAMTS-1 as described herein. In some embodiments, the polypeptides comprise SEQ ID NO: 5, 7, 9, 11, 13, 15, 17, 19, 21, 23, 25, 27, 33, 35, or combinations thereof. In some embodiments, the present invention provides polypeptides that comprise mutations that inactivate the metalloproteinase activity of ADAMTS-1. In some embodiments, the mutation is a Glu to Gln mutation that corresponds to position 386 (mouse) (or 385 in human) of the wild-type ADAMTS-1. In some embodiments, the mutant ADAMTS-1 comprises SEQ ID NO: 29 and/or 31. In some embodiments a nucleic acid molecule encoding such mutants is provided. In some embodiments, the nucleic acid molecule comprises SEQ ID NO: 30 and/or 32.

The present invention also provides methods for identifying a compound that induces the cleavage of ADAMTS-1 comprising performing a test assay comprising identifying a compound that inhibits heparin, wherein if a compound inhibits heparin, the compound would be said to induce the cleavage of ADAMTS-1. Since heparin inhibitors induce the cleavage of ADAMTS-1 heparin inhibitors would be able to activate the cleavage of ADAMTS-1. Thus, a compound that is identified as heparin inhibitor would be said to be able to induce the cleavage of ADAMTS-1. In some embodiments, the effect of heparin is a protective effect.

The present invention also provides methods of identifying a heparin inhibitor comprising contacting heparin and ADAMTS-1 with a test compound under conditions that ADAMTS-1 is cleaved in the absence of heparin and determining if the test compound inhibits heparin. As described herein, heparin inhibits the cleavage of ADAMTS-1. Therefore, a test compound that inhibits heparin will allow ADAMTS-1 to be cleaved by another protein or by itself. A test compound is said to be a heparin inhibitor if ADAMTS-1 is cleaved in the presence of heparin. In some embodiments, the heparin and ADAMTS-1 are free of cellular proteins. In some embodiments, the heparin and ADAMTS-1 is free of extracellular matrix.

A fragment of ADAMTS-1, a nucleic acid molecule encoding a fragment of ADAMTS-1, a compound that inhibits or activates the cleavage of ADAMTS-1 can be administered by any means to the individual whether in the form of a composition or a pharmaceutical composition. Methods of administration are known to one of skill in the art. For example, the agent can be prepared as a pharmaceutical composition. In some embodiments, the pharmaceutical composition comprises a pharmaceutically acceptable carrier or diluent. In some embodiments, the pharmaceutical compositions are sterile and/or pyrogen free. The pharmaceutical composition comprising the molecule and a pharmaceutically acceptable carrier or diluent may be formulated by one having ordinary skill in the art with compositions selected depending upon the chosen mode of administration. Suitable pharmaceutical carriers are described in the most recent edition of Remington's Pharmaceutical Sciences, A. Osol, a standard reference text in this field.

For parenteral administration, the composition can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions may be administered by any means that enables the agent to reach the agent's site of action in the body of a mammal. Because the compositions may be subject to being digested when administered orally, parenteral administration, i.e., intravenous, subcutaneous, intramuscular, would ordinarily be used to optimize absorption. In addition, the pharmaceutical compositions of the present invention may be injected at a site at or near hyperproliferative growth. For example, administration may be by direct injection into a solid tumor mass or in the tissue directly adjacent thereto. The composition may also be formulated with a pharmaceutically acceptable topical carrier and the formulation may be administered topically as a creme, lotion or ointment for example.

The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of a composition to treat cancer is used in an amount effect to have an anti-cancer effect. In some embodiments, the daily dosage is used in an amount to cleave ADAMTS-1 into a fragment that can inhibit cell proliferation or cell growth (e.g tumor growth). In some embodiments, the dosage can be about 1 μg to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

EXAMPLES

The invention is now described with reference to the following examples. These examples are provided for the purpose of illustration only and the invention should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

Example 1

Materials and Methods

Cell Lines and Reagents

Human umbilical vein endothelial cells (HUVECs) were obtained from Cambrex (Walkersville, Md.). TA3 transfectants were maintained as described previously (11, 12). Anti-v5 epitope (Invitrogen), -vWF (Dako), -phosphorylated tyrosine (BD Transduction Lab), -EGFR, -ErbB-2, -Erk1/2, and -phospho-Erk1/2 (Santa Cruz) antibodies, and Brdu-cell proliferation kit (Roche) and Apoptag kit (Chemicon) were used in the experiments.

Reverse Transcriptase-polymerase Chain Reaction (RT-PCR), Mutagenesis, and Expression Constructs Expression of ADAMTS-1 was assessed by RT-PCR as described (13). Full-length mouse ADAMTS-1 was obtained by RT-PCR with a primer pair consisting of 24 nucleotides corresponding to the 3' or 5' extremity of the coding sequence of ADAMTS-1 (accession number NM_009621). The stop codon was omitted from the reverse primers to fuse ADAMTS-1 to the C-terminal v5 epitope tag existed in the expression vector (pEF6/v5-HisTOPO, Invitrogen). Various mutation and deletion of ADAMTS-1 were generated as detailed in FIG. 1A using the QuikChange™ site and ExSite PCR-based site-directed mutagenesis kits (Stratagene).

Transfection

Lipofectamine (Invitrogen) was used to transfect $TA3_{wtl}$ cells with empty expression vector alone or the expression constructs containing cDNA inserts encoding ADAMTS-1 and various mutant or fragments of ADAMTS-1 (FIG. 1A). TA3 transfectants were selected and the expression level of v5-tagged full-length and fragments of ADAMTS-1 was determined by Western blotting with anti-v5 antibody (Invitrogen).

ADAMTS-1 Production and Purification, Proteolytic Cleavage Assay, and Western Blot Analysis Cell culture supernatants derived from Cos-7 and TA3 transfectants expressing v5-epitope tagged wild type ADAMTS-1 or ADAMTS-1 mutants (FIG. 1A) were collected and purified through $Ni^+$-Probond (Invitrogen) and anti-v5 antibody conjugated affinity columns (Sigma). Autoproteolytic cleavage capacity of ADAMTS-1 was assessed by in vitro proteolytic cleavage assay using purified ADAMTS-1. In this assay, 100 ng of ADAMTS-1 was incubated in 50 mM Tris-acetate buffer (pH 7.3) containing 5 mM $CaCl_2$ and 0.1M NaCl at 37° C. for 30 min, 1, 2, 4, 8 and 12 hours, and reaction was stopped by addition of 8×SDS sample buffer. The reaction products were analyzed by Western blot with anti-v5 mAb.

To assess ADAMTS-1 cleavage in cellular context and to determine how the cleavage is regulated, Cos-7 or TA3 transfectants expressing ADAMTS-1 or ADAMTS-1E/Q was cultured for 48 hours in the absence or presence of different reagents as detailed in the figure legend, and the cell culture supernatants were collected and analyzed by Western blot with anti-v5 antibody.

Tumor Cell Tracking and Pulmonary Metastasis

To track TA3 transfectants during early pulmonary metastasis, the TA3 transfectants were labeled with green 5-chloromethyl-fluorescein diacetate (CMFDA, Molecular Probes, Inc.) as described (13), and the CMFDA-labeled TA3 transfectants ($1 \times 10^6$ cells/mouse) were injected into the tail vein of A/Jax syngenic mice (the Jackson Lab). The mice were sacrificed 24 hours after the injection, and lungs were removed, fixed, and sectioned. The localization of tumor cells in mouse lung parenchyma were revealed under fluorescence microscope, and the extent of tumor cell extravasation was determine by counting number of the tumor cells in five randomly selected 10× microscopic fields.

Experimental pulmonary metastasis was carried out as detailed previously (13), and five independent clonal TA3 transfectants expressing ADAMTS-1, $ADAMTS-1_{CTCF}$, $ADAMTS-1_{NTCF}$ or $ADAMTS-1_{minusTSP}$, or transfected with the empty expression vector were used. For each type of the experiment, six mice were injected with each clonal transfectant and two independent experiments were performed. The experimental mice were observed daily after the i.v. injection and duration of mouse survival was recorded. The survival rate of these mice was calculated as the following: survival rate (%)=(number of mice are still alive/total number of the experimental mice)×100%. The mice that are free of symptom 60 days after the i.v. injection were sacrificed and their lungs were examined. In the second set of experiments, 11 and 18 days after i.v. injection, pulmonary metastatic burden was assessed by measuring weight of the mouse lungs.

Histology and Immunohistochemistry

To determine the tumor cell proliferation rate in vivo, 5-Bromo-2'-deoxy-uridine (Brdu) was injected into mice four hours prior to sacrifice of the experimental mice. The mouse lungs were fixed, sectioned, and stained with H&E as described (11). In addition, the sections were reacted with anti-von Willebrand factor (vWF) antibody to assess tumor angiogenesis, with anti-Brdu antibody to detect proliferating cells or with Apoptag kit to detect apoptotic cells in situ. Total number of the tumor cells and number of the tumor cells that are positive for anti-Brdu antibody or TUNNEL-staining were counted in five randomly selected 400× microscopic fields within the pulmonary macro- and micro-metastases. More than 2,000 cells were counted in total for each type of transfectants. The proliferation and apoptosis rate was calculated as the following: proliferation or apoptosis rate=(number of the anti-Brdu or TUNEL-positive cells per microscopic field/total number of the tumor cells per microscopic field)× 100%. To determine blood vessel number, the vWF-positive blood vessels were countered in six randomly selected 200x microscopic fields within macro- or micro-metastases. The number of blood vessels/microscopic field was expressed as means ±S.D.

EGFR and ErbB-2 Phosphorylation

RIPA buffer (50 mM Tris-HCl, PH 7.4, 50 mM NaCl, 1% Triton-X100, 2 mM EDTA, 2 mM sodium orthovanadate, 2 mM sodium fluoride, 2 mM phenylmethylsulfonyl fluoride, 1 mM Leupeptin, 1 mM Pepstain A, and 10 μg/ml aprotinin) was used to extract the lung tissues derived from the mice that were injected with or without different TA3 transfectants ($1 \times 10^6$/mouse) intravenously 24 hours prior. The proteins were used in the immunoprecipitation reactions to pull-down EGFR and ErbB-2 using the agarose beads conjugated with anti-EGFR or anti-ErbB-2 antibody (Santa Cruz). The precipitated proteins were analyzed by Western blotting with anti-phosphotyrosine antibody (BD Bioscience) to detect phosphor-EGFR and phosphor-ErbB-2, or with anti-EGFR or anti-ErbB-2 antibody (Santa Cruz) to detect total amount of EGFR or ErbB-2, respectively.

Shedding of the EGF Family GFs and Activation of Erk1/2 Kinases

Shedding of the transmembrane precursors of AR, HB-EGF, and epigen by ADAMTS-1, its mutant and fragments were assessed by co-transfection of Cos-7 cells with the expression constructs containing cDNA inserts that encode these EGF family precursors and various ADAMTS-1 constructs as detailed in the figure legend. The concentrated cell culture supernatants of the co-transfected COS-7 cells were analyzed by Western blotting to detect the soluble GFs using the corresponding antibodies (R&D Systems).

Ability of the ADAMTS-1 fragments to inhibit activation of Erk1/2 kinase induced by soluble AR (5 ng/ml) and HB-EGF (4 ng/ml) were assessed by applying the serum starved MCF-10A cells with purified soluble AR or HB-EGF in the absence or presence of their corresponding neutralization antibodies or purified full-length ADAMTS-1 or the ADAMTS-1 fragments (400 ng). MCF-10A cells were then lysed and equal amount of the proteins were analyzed by Western blotting with anti-phospho-Erk1/2 to detect phosphor-Erk1/2 or with anti-Erk antibody to detect total amount of Erk1/2 protein.

HUVECs were cultured until subconfluence and switched to serum-free medium (SFM) for overnight. $VEGF_{165}$ (10 ng), bFGF (10 ng), AR (5 ng), and HB-EGF (4 ng) were applied to the serum-starved HUVECs in the absence or presence of 400 ng of ADAMTS-1, ADAMTS-1$_{minusTSP}$, ADAMTS-1$_{NTCF}$, or ADAMTS-1$_{CTCF}$ for 20 minutes. The HUVECs were lysed and equal amount of the proteins were subjected to Western blotting with anti-phospho-Erk1/2 or anti-Erk (Santa Cruz) to detect phosphor-Erk1/2 or total amount of Erk, respectively.

Example 2

ADAMTS-1 Undergoes Auto-proteolytic Cleavage and the Self-cleavage of ADAMTS-1 is Regulated Previous results have shown that ADAMTS-1 is cleaved within the spacer region and several matrix metalloproteinases (MMPs) are responsible for the cleavage (9). Since several other members of ADAMTS family undergo auto-proteolytic cleavage and ADAMTS-1 is an active metalloproteinase, the possibility that the cleavage of ADAMTS-1 can be mediated by its own metalloproteinase activity was investigated. To achieve that, a protease-dead mutant of ADAMTS-1 was generated by switching $E_{386}$ to Q (ADAMTS-1E/Q) in the Zinc-binding pocket of the metalloproteinase domain. The expression constructs containing v5-epitope tagged wild type ADAMTS-1 or ADAMTS-1E/Q were used to transfect Cos-7 cells. The cell culture supernatants of the transiently transfected Cos-7 cells were analyzed and the results showed that only wild type ADAMTS-1 but not ADAMTS-1E/Q is cleaved to generate the C-terminal cleavage fragments (FIG. 1B, arrows), suggesting that the metalloproteinase activity of ADAMTS-1 is required for the cleavage.

In order to produce full-length ADMATS-1, the regulation of ADAMTS-1 cleavage was investigated. Different reagents were applied to a stable TA3 transfectant expressing ADAMTS-1, and the cell culture supernatants were analyzed 48 hours later. The result showed that heparin and heparan sulfate (HS) completely block the proteolytic cleavage of ADAMTS-1, while the control glycosaminoglycans (GAGs), chondroitin sulfate(CS) and hyaluronan (HA), and displayed no effect on the cleavage (data not shown). This result suggests that auto-proteolytic cleavage of ADAMTS-1 is regulated by synthesis and degradation rate of HS/heparan sulfate proteoglycans (HSPGs) in the microenvironment where ADAMTS-1 is produced and HS/HSPGs likely play important role in regulating ADAMTS-1 function.

Full-length ADAMTS-1 protein was produced by Cos-7 cells transfected with the expression construct containing ADAMTS-1 cDNA in the presence of heparin. Cell culture media of the transfected Cos-7 cells were collected and purified through the affinity columns. Purified ADAMTS-1 was used in a proteolytic cleavage assay and the result showed that ADAMTS-1 was auto-proteolytically cleaved to release v5-epitope tagged C-terminal cleavage fragments that have molecular weight similar to that generated in the cell culture condition.

ADAMTS-1 Promotes Metastasis, While ADAMTS-1$_{NTCF}$ and ADAMTS-1$_{CTCF}$ Block the Process ADAMTS-1 was found to inhibit bFGF-induced vascularization in the cornea pocket assay and VEGF-induced angiogenesis in the chorioallantoic membrane assay and tumor growth in vivo. However, a study analyzing clinical pancreatic cancer samples demonstrated that increased expression of ADAMTS-1 is correlated to enhanced metastatic potential and worse prognosis, implying that ADAMTS-1 facilitates tumor metastasis. In addition, studies have shown that ADAMTS-1 is one of the genes up-regulated in the breast cancer with elevated metastatic activity. To determine the exact roles of ADAMTS-1 and its cleavage fragments in tumor metastasis and the underlying mechanism, set to investigate how overexpression of full-length and the fragments of ADAMTS-1 affects metastasis of TA3 mammary carcinoma (TA3) cells. As shown in FIGS. 1B and C, the C-terminal cleavage fragments of ADAMTS-1 are heterogenic in their molecular weight, suggesting that ADAMTS-1 are cleaved at more than one sites within the spacer/Cys-rich region (FIG. 1A, arrows). The molecular weight of the shortest C-terminal cleavage fragments is similar to that of the expressed C-terminal fragment of ADAMTS-1 containing the last two TSP-1 type I motifs (ADAMTS-1$_{CTCF}$: amino acids 842-951, FIGS. 1A, D), suggesting that in addition to the previous identified cleavage site in the spacer region (FIG. 1A, the bigger arrow), there is at least one additional cleavage site at the junction between spacer region and the second TSP-1 type I motif (FIG. 1A, the smaller arrow).

It was difficult to express the N-terminal fragments of ADAMTS-1 containing different parts of the spacer and/or Cys-rich domains (data not shown). In addition, studies have shown that auto-proteolytic cleavage of ADAMTS-4 occurs at the multiple sites within its spacer/Cys-rich region, and the shortest N-terminal cleavage fragment of ADAMTS-4 is generated by cleavage around the junction between the Cys-rich domain and the TSP-1 type I motif. Thus, two expression constructs containing N-terminal fragments of ADAMTS-1 were made, which expressed well in TA3 cells. These constructs contain the N-terminal domains of ADAMTS-1 until the end of the first TSP-1 type I motif (ADAMTS-1$_{NTCF}$, amino acids 1-596, FIGS. 1A, D) or until the end of the disintegrin domain (ADAMTS-1$_{minusTSP}$, amino acids 1-545, FIGS. 1A, D). ADAMTS-1$_{NTCF}$ likely represents the shortest N-terminal cleavage fragment of ADAMTS-1.

In order to assess the effects of ADAMTS-1 and its fragments on tumor metastasis reliably, the heterogeneity of TA3 cells was eliminated by transfecting the cells with empty expression vector containing neomycin-resistant gene. A clonal TA3 cell (TA3$_{wtl}$) that undergoes aggressive pulmonary metastasis after intravenous (i.v.) injection was selected (data not shown). Our RT-PCR result showed that like its wild type counterpart, TA3$_{wtl}$ cells express ADAMTS-1 endogenously (data not shown). TA3$_{wtl}$ was used to transfect several expression constructs that contain blasticidin-resistant gene and different ADAMTS-1 cDNA inserts (FIG. 1A). Five independent clonal TA3 transfectants that were transfected with the empty expression vector alone (TA3$_{wtb}$) or expressing the following gene products were identified and used in pulmonary metastasis experiments: wild type ADAMTS-1 (TA3$_{ADAMTS-1}$), ADAMTS-1$_{NTCF}$ (TA3$_{ADAMTS-1NTCF}$), ADAMTS-1$_{CTCF}$ (TA3$_{ADAMTS-1CTCF}$), and ADAMTS-1$_{minusTSP}$ (TA3$_{ADAMTS-1minusTSP}$). These TA3 transfectants displayed similar growth rate in cell culture condition (data not shown).

Figure 2:
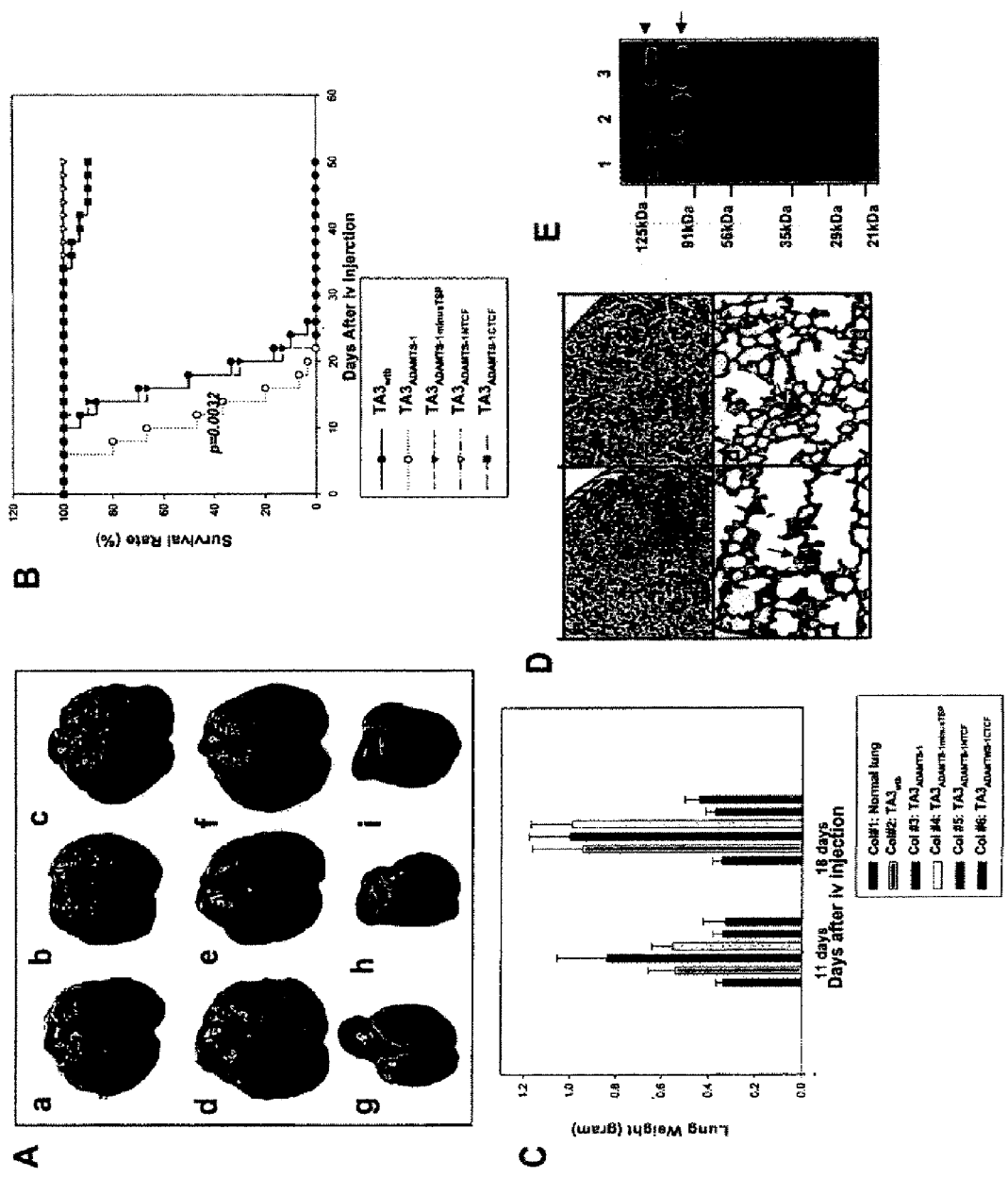
FIG. 2. ADAMTS-1 promotes pulmonary metastasis, while ADAMTS-1$_{NTCF}$ and ADAMTS-1$_{CTCF}$ inhibits the process. A. Representative gross pictures of the mouse lungs two-three weeks after i.v. injection of TA3$_{wtb}$ (a-c) or TA3$_{ADAMTS-1(d-f)}$, or TA3$_{ADAMTS-1NTCF(g-i)}$ cells. B. Survival rate of the experimental mice which were injected with the TA3 transfectants intravenously. Total of thirty mice were used for each type of transfectants. C. Pulmonary metastatic burden is expressed by weight of the lungs derived from the experimental mice 11 days and 18 days after the i.v. injection of the TA3 transfectants. D. The representative H&E stained lung sections were derived the experimental mice injected with TA3$_{wtb}$ (a), TA3$_{ADAMTS-1}$ (b), TA3$_{ADAMTS-1NTCF}$ (c), and TA3$_{ADAMTS-1CTCF}$ (d) cells. Bar, 100 µm. E. Western blot analysis of v5-epitope tagged ADAMTS-1 protein expressed by TA3$_{ADAMTS-1}$ cells in vivo using anti-v5 mAb. The proteins were derived from different pulmonary metastases derived from TA3$_{ADAMTS-1}$ cells. The arrow indicates the mature proteolytically active ADAMTS-1, and the arrowhead marks pro-ADAMTS-1.

Our results showed that overexpression of ADAMTS-1 significantly accelerated pulmonary metastasis and shortened the survival time of the mice (FIGS. 2A-C). On the contrary, ADAMTS-1$_{NTCF}$ or ADAMTS-1$_{CTCF}$, but not ADAMTS-1$_{minusTSP}$ blocks pulmonary metastasis of the TA3 transfectants (FIGS. 2A-C), suggesting that the inhibitory effect of these ADAMTS-1 fragments is likely derived from the TSP type I motifs which exist in ADAMTS-1$_{NTCF}$ and ADAMTS-1$_{CTCF}$, but not in ADAMTS-1$_{minusTSP}$; and the anti-tumor activity is likely masked in full-length ADAMTS-1.

The metastatic tumors derived from TA3$_{wtb}$, TA3$_{ADAMTS-1}$, and TA3$_{ADAMTS-1minusTSP}$ cells are invasive and fused together (FIG. 2A, D, a-b, and data not shown), which made it difficult to determine accurate number of the metastatic lesions. Thus, metastatic burden of the experimental mice was quantified by average weight of the experimental mouse lungs (FIG. 2C). Because there is a significant difference in survival time of these mice and the mice usually succumb to pulmonary metastasis when metastatic burden causes the lung weight to reach 1-1.2 grams, the metastatic burden of the remaining survival mice at day 11 and day 18 after i.v. injection of the TA3 transfectants was measured. At least fifteen experimental mouse lungs were measured for each type of the transfectants at each time point. Our results showed that overexpression of ADAMTS-1 accelerated time that is needed to reach the maximal metastatic burden and shortened the survival time of the mice, while overexpression of ADAMTS-1$_{NTCF}$ or ADAMTS-1$_{CTCF}$ blocked pulmonary metastasis and render most of the experimental mice free of metastatic disease (FIGS. 2B-C).

Histologic analysis of the lung sections showed that TA3$_{wtb}$, TA3$_{ADAMTS-1}$, and TA3$_{ADAMTS-1minusTSP}$ cells are invasive and fill up the pulmonary space (FIG. 2D-a-b, and data not shown). On the contrary, only micrometastasis were detected in the lungs received TA3$_{ADAMTS-1NTCF}$ or TA3$_{ADAMTS-1CTCF}$ cells (FIG. 2D-c, d, arrows). To assess whether ADAMTS-1 expressed by the transfected TA3 cells is cleaved in vivo, different pulmonary tumors derived from TA3$_{ADAMTS-1}$ cells were lysed and the proteins were analyzed by Western blotting with anti-v5 antibody, which recognizes the v5-tagged ADAMTS-1. The result showed that ADAMTS-1 protein is maintained in full-length form in vivo and no cleavage fragments of ADAMTS-1 were detected (FIG. 2E). This result suggests that proteolytic cleavage of ADAMTS-1 regulates ADAMTS-1 function and the cleavage status of ADAMTS-1 in vivo determine its effect (stimulatory or inhibitory) on tumor metastasis.

ADAMTS-1$_{NTCF}$ and ADAMTS-1$_{CTCF}$ Blocks Pulmonary Metastasis by Inhibiting Proliferation and Inducing Apoptosis of Tumor Cells, and by Repressing Tumor Angiogenesis To determine the mechanism underlying the pro-tumor effect of full-length of ADAMTS-1 and the anti-tumor effect of ADAMTS-1$_{NTCF}$ and ADAMTS-1$_{CTCF}$, proliferation and apoptosis rates of the tumor cells and the extent of tumor angiogenesis during pulmonary metastasis of TA3 transfectants were analyzed. A 5-Bromo-2'-deoxy-uridine (Brdu) incorporation assay and in situ detection of apoptotic cells on the sections derived from the experimental mouse lungs (six days after i.v. injection of TA3 transfectants) was performed. Results demonstrated that expression of ADAMTS-1$_{NTCF}$ or ADAMTS-1$_{CTCF}$, but not that of ADAMTS-1$_{minusTSP}$, inhibits proliferation and promotes apoptosis of the tumor cells, and inhibits tumor angiogenesis; while overexpression of full-length exogenous ADAMTS-1 on the top of endogenous ADAMTS-1 has weak effect on tumor cell proliferation and apoptosis and promotes tumor angiogenesis in vivo. These results imply that ADAMTS-1 plays a role in releasing/activating growth/survival/ angiogenesis factors in the microenvironments, while ADAMTS-1$_{NTCF}$ and ADAMTS-1$_{CTCF}$ blocks/interferes activities of the factors that promote tumor cell proliferation and survival and tumor angiogenesis.

ADAMTS-1 Promotes Extravasation of the Tumor Cells and Activation of EGFR and ErbB-2 In Vivo, and Promotes Shedding of AR and HB-EGF Activation of EGFR and ErbB-2 is known to promote proliferation and survival of breast carcinoma cells and is essential for progression of breast cancers. To determine whether ADAMTS-1 promotes activation of EGFR and/or ErbB-2 in vivo, activity of EGFR and ErbB-2 in the lungs where TA3$_{wtb}$, TA3$_{ADAMTS-1}$, TA3$_{ADAMTS-1NTCF}$, or TA3$_{ADAMTS-1CTCF}$ cells were injected intravenously 24 hours prior was assessed. In order to normalizing amount of the tumor cells that were included in the protein lysates and used in the immunoprecipitation, a tumor cells tracking assay to determine the pulmonary extravasation rate of TA3 transfectants that were injected intravenously into their syngenic mice 24 hours prior was performed. The result showed that overexpression of ADAMTS-1 promotes tumor cell extravasation into lung parenchyma, while expression of TA3$_{ADAMTS-1NTCF}$ or TA3$_{ADAMTS-1CTCF}$ inhibits the process (FIGS. 3A-B).

Normal mouse lungs and the mouse lungs that received TA3 transfectants intravenously 24 hour prior were lysed, and the protein lysates that statistically contain the same amount of the tumor cells were used in immunoprecipitation to pull-down EGFR or ErbB-2 and anti-phosphotyrosine antibody was used to detect phosphor-EGFR or phosphor-ErbB-2. The result showed that overexpression of ADAMTS-1 promotes activation of EGFR and ErbB-2 (FIG. 3C). On the contrary, expression of ADAMTS-1$_{NTCF}$ or ADAMTS-1$_{CTCF}$ blocks activation of EGFR and ErbB-2 (FIG. 3C).

Whether increased activation of EGFR and ErbB-2 induced by ADAMTS-1 is achieved via shedding/activating EGF family GF precursors, the ligands of ErbB receptor tyrosine kinases which include EGFR, ErbB-2, -3, and -4. EGF family GFs include EGF, transforming growth factors-α (TGF-α), HB-EGF, AR, betacellulin, epiregulin, neuregulin, and epigen, and are shed from cell surface was investigated. Increasing amount of data suggests that shedding of the EGF family GF precursors are essential in regulating availability and bioactivity of these factors and in activation of the ErbB signaling pathways. The members of ADAM family, especially ADAM17 have been shown to play major but not sole role in shedding of these factors.

To determine whether ADAMTS-1 play an important role in constitutive shedding EGF family GFs especially the ones that bind to heparin, Cos-7 cells with several EGF family GF precursors that are expressed by TA3 cells (data not shown) including HB-EGF, AR, and epigen with were co-transfected with empty expression vector or the expression constructs containing full-length ADAMTS-1, ADAMTS-1E/Q or various ADAMTS-1 fragments. Serum-free cell culture medium (SFM) of the co-transfected Cos-7 cells were collected, concentrated and analyzed. Cos-7 cells express endogenous ADAMTS-1 (data not shown). Overexpression of exogenous ADAMTS-1 promotes shedding of AR and HB-EGF but not shedding of epigen (FIG. 4D). More importantly, overexpress ADAMTS-1E/Q which acts as a dominant negative regulator of endogenous ADAMTS-1 completely blocks the shedding of AR and inhibits the shedding of HB-EGF, while ADAMTS-1 fragments displayed no significant effect on the shedding (FIG. 3D). These data suggest that ADAMTS-1 promotes activation of EGFR and ErbB-2 by promoting shedding and activation of the EGF family GFs.

ADAMTS-$1_{NTCF}$ and ADAMTS-$1_{CTCF}$ Inhibit Activation of Erk1/2 Kinases Induced by the EGF Family GFs Since ADAMTS-$1_{NTCF}$ and ADAMTS-$1_{CTCF}$ display no significant inhibitory effect on shedding of AR and HB-EGF, it was investigated as to whether ADAMTS-$1_{NTCF}$ and ADAMTS-$1_{CTCF}$ inhibits activation of EGFR and ErbB-2 by interfering activity of the soluble EGF family GFs. To assess that, purified soluble AR or HB-EGF was applied to MCF-10A mammary epithelial cells in the presence and absence of the naturalizing antibodies to HB-EGF or AR, ADAMTS-$1_{NTCF}$, ADAMTS-$1_{CTCF}$, or full-length ADAMTS-1. This result showed that the neutralizing antibodies, ADAMTS-$1_{NTCF}$ and ADAMTS-$1_{CTCF}$, but not full-length ADAMTS-1 inhibit Erk1/2 kinase activation induced by soluble AR and HB-EGF. This result suggests that ADAMTS-$1_{NTCF}$ or ADAMTS-$1_{CTCF}$ inhibits activation of EGFR and ErbB-2 by inhibiting their ligand activity likely via interfering the binding between ligands and their receptors and that the different effects of ADAMTS-1 and its cleavage fragments on availability and activity of soluble AR and HB-EGF underlie their opposite roles in tumor metastasis.

Figure 3:
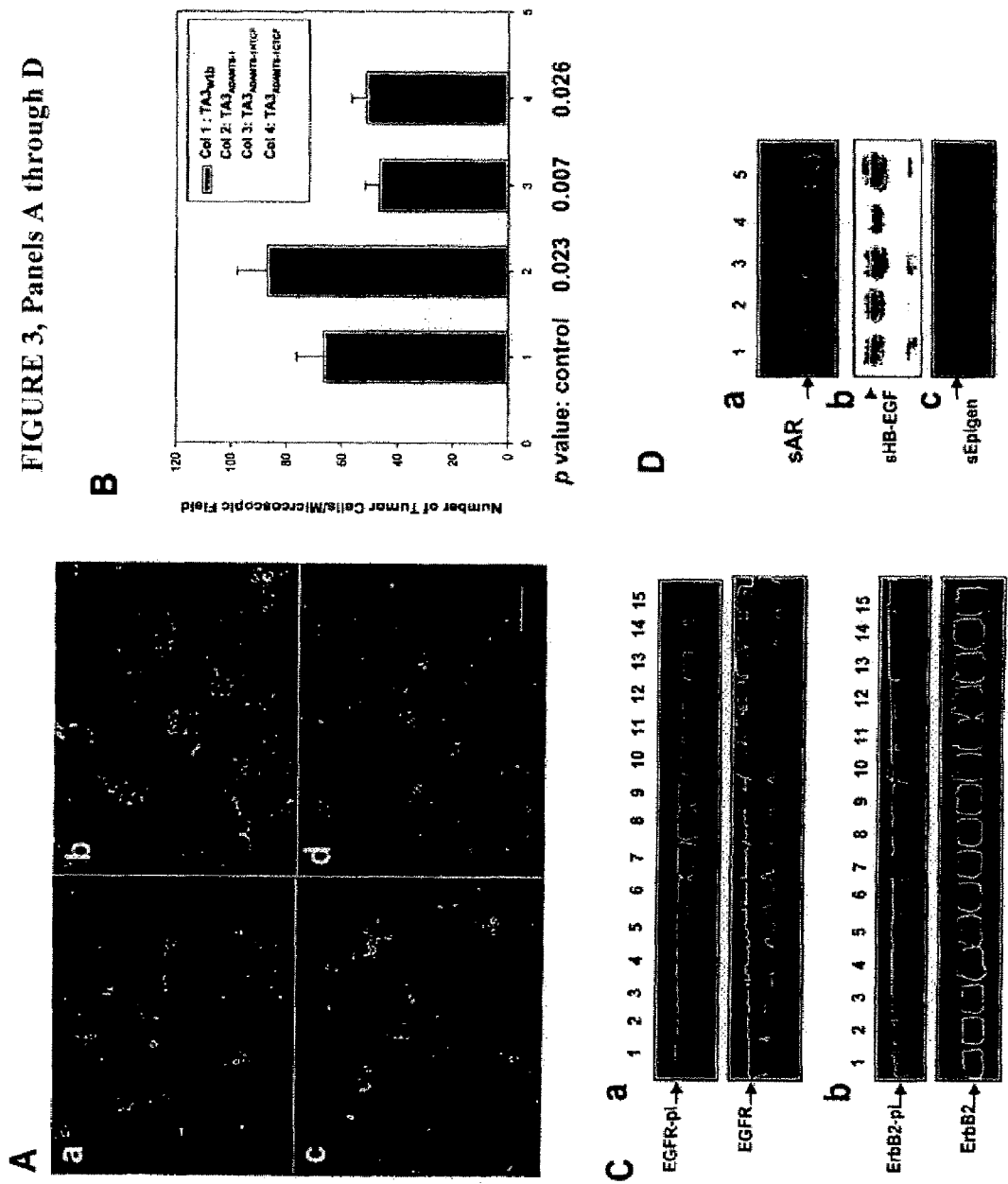
FIG. 3, Panels A-D ADAMTS-1$_{NTCF}$ and ADAMTS-1$_{CTCF}$ block activation of EGFR and ErbB-2 in vivo, while ADAMTS-1 promotes activation of these receptors and shedding of AR and HB-EGF precursors. A. Tumor cell tracking assay was performed to determine the pulmonary extravasation of TA3 transfectants. 24 hours after i.v. injection of the green fluorescein labeled TA3 transfectants, the mice lung were fixed and sectioned. TA3$_{wtb}$ (A-a), TA3$_{ADAMTS-1}$ (A-b), TA3$_{ADAMTS-1NTCF}$ (A-c), and TA3$_{ADAMTS-1CTCF}$ (A-d) cells in the lung parenchyma were shown. B. The pulmonary extravasation rates of the TA3 transfectants were expressed as average number of the tumor cells per microscopic field. C. Activation of EGFR and ErbB-2 in vivo: immunoprecipitation with anti-EGFR (C-a) or anti-ErbB-2 (C-b) antibody was performed using the protein lysates derived from the mouse lungs which were implanted without (lanes 1-3) or with TA3$_{wtb}$ (lanes 4-6), TA3ADAMTS-1 (lanes 7-9), TA3$_{ADAMTS-1NTCF}$ (lane 10-12), and TA3$_{ADAMTS-1CTCF}$ (lanes 13-15) 24 hours prior. To normalize number of the tumor cells that were included in the protein lysates, based on the tumor cell extravasation rates (B), 100 μg of the lung lysates with or without TA3$_{wtb}$ cells, 71 μg of the lung lysates containing TA3$_{ADAMTS-1}$ cells, and 143 μg of the lung lysates containing TA3$_{ADAMTS-1NTCF}$ cells, and 130 μg of the lysates containing TA3$_{ADAMTS-1CTCF}$ cells have been used The precipitated proteins were analyzed by Western blotting with anti-phosphotyrosine antibody to detect phosphor-EGFR (C-a, upper panel) or phosphor-ErbB-2 (C-b, upper panel), or with anti-EGFR (C-a, bottom panel) or anti-ErbB-2 (C-b, bottom panel) antibody to detect total amount of EGFR or ErbB-2, respectively. D. ADAMTS-1 promotes shedding of AR (D-a), HB-EGF (D-b), but not epigen (D-c), and the constitutive shedding of AR and HB-EGF is blocked or inhibited by ADAMTS-1E/Q, respectively (lane 4 in D-a and -b). Cos-7 cells were co-transfected with the expression constructs containing cDNA inserts that encode AR, HB-EGF, or epigen precursors without (lane 1) or with ADAMTS-1$_{NTCF}$ (lane 2), ADAMTS-1$_{CTCF}$ (lane 3), ADAMTS-1E/Q (lane 4), or ADAMTS-1 (lane 5), and the concentrated serum-free culture media derived from these co-transfected Cos-7 cells were analyzed using anti-AR, HB-EGF, or epigen antibody.

To further determine the molecular mechanism underlying the anti-angiogenic activity of ADAMTS-$1_{NTCF}$ and ADAMTS-$1_{CTCF}$, it was investigated how these fragments affect activities of several important growth/angiogenic factors that are known to regulate angiogenesis. Bioactivity of $VEGF_{165}$, basic FGF (bFGF), HB-EGF, and AR were revealed by their ability to induce activation of Erk1/2 kinases in HUVECs in the presence or absence of purified ADAMTS-1 or the ADAMTS-1 fragments. Our results showed that ADAMTS-$1_{NTCF}$ and ADAMTS-$1_{CTCF}$ but not full-length ADAMTS-1 or ADAMTS-$1_{minusTSP}$ block activation of Erk1/2 kinases induced by $VEGF_{165}$, HB-EGF, and AR but not that induced by bFGF (FIG. 3). These results suggest that ADAMTS-$1_{NTCF}$ and ADAMTS-$1_{CTCF}$ block tumor angiogenesis by sequestering the activities of several important heparin binding factors that are essential for endothelial cells proliferation and survival.

ADAMTS-1 was found to inhibit tumor growth by blocking tumor angiogenesis; however, this study did not investigate whether the anti-tumor activity is derived from the full-length ADAMTS-1, its cleavage fragments, or both. On the contrary, increased expression of ADAMTS-1 was correlated to the increased metastatic potential in the clinic tumor samples. The current study was designed to better understand the role of full-length and the cleavage fragments of ADAMTS-1 in tumor metastasis and to elucidate the underlying mechanisms. It was demonstrated that overexpression of ADAMTS-1 promotes tumor metastasis by promoting tumor cell extravasation and tumor angiogenesis. It is well established that tumor cell extravasation is a critical step during tumor metastasis and studies have shown that ADAMTS-1 is capable of degrading aggrecan and versican. The ability of ADAMTS-1 to degrade aggrecan/versican and other not yet identified ECM components is likely responsible for the enhanced extravasation ability of TA3$_{ADAMTS-1}$ cells. Furthermore, as described herein, ADAMTS-1 promotes shedding of AR and HB-EGF, which in turn promotes activation of EGFR and ErbB-2 and proliferation and survival of the tumor cells in vivo.

In the current study, it was demonstrated that ADAMTS-1 undergoes auto-proteolytic cleavage and overexpression of the cleavage fragments of ADAMTS-1 (ADAMTS-$1_{NTCF}$ and ADAMTS-$1_{CTCF}$) block metastasis of TA3 cells by inhibiting extravasation, proliferation and survival of the tumor cells, and by repressing tumor angiogenesis via interfering activities of several important heparin binding growth/angiogenic factors. Furthermore, it was demonstrated that auto-proteolytic cleavage of ADAMTS-1 is blocked by HS, which suggests that the level of HS/HSPG in the microenvironment likely regulates which form of ADAMTS-1 (full-length or the cleavage fragments) presents predominantly in the microenvironment to exert pro- or anti-tumor activity, respectively. Thus, the roles of ADAMTS-1 and its cleavage fragments in tumor metastasis, provided the regulatory mechanism of ADAMTS-1 function (by auto-proteolytic cleavage and HS/HSPGs), and revealed the mechanisms underlying the function of ADAMTS-1 and the ADAMTS-1 cleavage fragments (by regulating availability and activity of the EGF family GFs and ErbB signaling pathway).

Shedding EGF Family GFs by ADAMTS-1

Although functional differences between mature soluble EGF family GFs and their transmembrane precursors are not well-established, the phenotype similarity between TGF-α- and ADAM17-null mice and between HB-EGF-null and HB-EGF cleavage resistant mice clearly suggested that shedding of these precursors is essential for availability and activity of these factors. Several members of ADAM family including ADAM 9, 10, 12, 17 have been implicated in shedding of HB-EGF and AR. The studies using the cells derived from ADAM-9, -10, -12, -15, and/or -17 null-mice have suggested that ADAM17 are the major but not the sole sheddase of AR and HB-EGF, and other member(s) of ADAM and/or ADAMTS family is(are) likely play important roles as well, especially in the non-PMA-induced/metalloproteinase inhibitor sensitive/constitutive shedding of these factors.

Several members of EGF family GFs including HB-EGF and AR bind to HS/HSPGs. ADAMTS-1 binds to HS as well through the spacer region and the TSP type I motifs, which brings the proteinase domain of ADAMTS-1 close to the HS/HSPG bound factors and makes ADAMTS-1 as an ideal sheddase to cleave these HS/HSPG binding GF precursors. The present disclosure has provided evidences that ADAMTS-1 promotes shedding of AR and HB-EGF and ADAMTS-1 may be a major sheddase that is responsible for constitutive shedding of AR and HB-EGF. Soluble AR and HB-EGF shed by ADAMTS-1 can in turn promote tumor cell survival and proliferation and tumor angiogenesis in vivo.

As discussed herein, it is shown that ADAMTS-1 but not the ADAMTS-1 fragments promotes shedding of AR and HB-EGF, suggesting that the intact spacer/Cys-rich domain is required for the shedding and the spacer/Cys-rich domain contains substrate recognition/binding site(s) which is(are) destroyed by the auto-proteolytic cleavage in this region. Since all the members of ADAMTS family have similar domain organization, in addition to ADAMTS-1, other members of the ADAMTS family may also involve in regulating availability and activity of HS/HSPG-binding factors.

The Anti-Tumor Activity of the ADAMTS-1 Fragments is Masked in the Full-Length Molecule.

As described herein, it is demonstrated that in contrast to the effect of full-length ADAMTS-1, the ADAMTS-1 cleavage fragments (ADAMTS-1$_{NTCF}$ and ADAMTS-1$_{CTCF}$) block pulmonary metastasis of TA3 cells. How can autoproteolytic cleavage convert a pro-tumor factor into anti-tumor ones? The results suggest that auto-proteolytic cleavage destroys the substrate binding domain in the spacer/Cys-rich region that is likely required for binding to AR and HB-EGF precursors. In addition, it is described herein that the N-terminal deletion fragment of ADAMTS-1 in which all the TSP type I motifs were deleted (ADAMTS-1$_{minusTSP}$) displayed no anti-tumor activity, suggesting that the anti-tumor activity of ADAMTS-1$_{NTCF}$ and ADAMTS-1$_{CTCF}$ is derived from the TSP type I motif. Even though full-length ADAMTS-1 contains all three TSP type I motifs, they are likely masked and unable to exert anti-tumor activity. Auto-proteolytic cleavage of ADAMTS-1 at the spacer/Cys-rich region not only renders the N-terminal cleavage fragment (ADAMTS-1$_{NTCF}$) that contains the metalloproteinase domain incapable of binding to and shedding AR and HB-EGF precursors (FIG. 3D), but also exposes the cryptic anti-tumor domains in both N- and C-terminal cleavage fragments. In addition to ADAMTS-1, ADAMTS-4, and -12 undergo proteolytic cleavage at their spacer/Cys-rich region as well. The auto-proteolytic cleavage may be a general mechanism that regulates function of many ADAMTS family members, and our results provided the first example of this type of regulatory mechanism.

Figure 4:
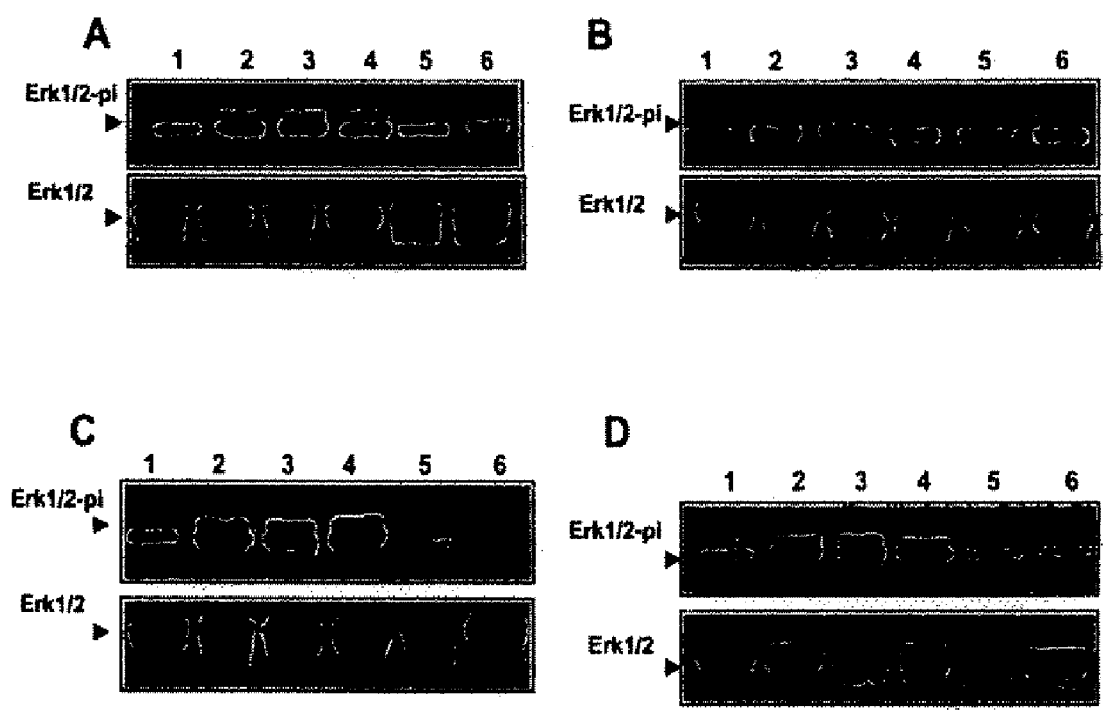
FIG. 4, Panels A through D. ADAMTS-1$_{NTCF}$ and ADAMTS-1$_{CTCF}$ blocks activation of Erk1/2 kinases in HUVECs induce by AR, HB-EGF, or VEGF$_{165}$. VEGF$_{165}$ (A, 15 ng/ml), bFGF (B, 15 ng/ml), HB-EGF (C, 4 ng/ml), or AR (D, 5 ng/ml) was used alone (lane 2) or in the presence of full-length ADAMTS-1 and ADAMTS-1 fragments (lanes 3-6). The serum-starved HUVECs were applied with SFM alone (lane 1), or containing different GFs alone (lane 2) or the GFs plus 400 ng of ADAMTS-1 (lane 3), ADAMTS-1$_{minusTSP}$ (lane 4), ADAMTS-1$_{NTCF}$ (lane 5) or ADAMTS-1$_{CTCF}$ (lane 6). Equal amount of the proteins derived from these HUVECs were analyzed Western blotting with anti-phospho-Erk1/2 to detect phosphor-Erk1/2 (upper panels in A-D) or with anti-Erk antibody to detect total amount of Erk1/2 (bottom panels in A-D).

As described herein, it has been shown that ADAMTS-1$_{NTCF}$ and ADAMTS-1$_{CTCF}$ inhibits activation of Erk1/2 kinase induced by AR, HB-EGF, or VEGF (FIG. 4). A recent study has shown that ADAMTS-1 inhibits VEGF activity by blocking the binding between VEGF and their receptor. Although additional study is required to determine the exact biochemical mechanism underlying the inhibitory effect of ADAMTS-1$_{NTCF}$ and ADAMTS-1$_{CTCF}$, they likely exert their inhibitory effect by sequestering these soluble GFs from their receptors.

The function of ADAMTS-1 is Regulated by HS/HSPGs

As described herein, heparin/HS blocks auto-proteolytic cleavage of ADAMTS-1, and full-length ADAMTS-1 and the ADAMTS-1 cleavage fragments (ADAMTS-1$_{NTCF}$ and ADAMTS-1$_{CTCF}$) displayed opposite effects on tumor metastasis. Thus, ability of ADAMTS-1 to inhibit or promote tumor metastasis is dependent on the ability of tumor cells and their surrounding microenvironment to cleave ADAMTS-1. In other words, in a microenvironment that is highly enriched HS and HSPGs, binding of ADAMTS-1 to HS/HSPGs protects the proteolytic cleavage sites in the spacer/Cys-rich region which keeps ADAMTS-1 in the full-length form and in turn binds and cleaves its substrates including transmembrane AR and HB-EGF. In that situation, full-length ADAMTS-1 exerts pro-tumor activity by releasing and activating pro-proliferation, -survival, and -angiogenic factors. In addition, the anti-tumor activity derived from TSP type I motifs is likely masked in full-length ADAMTS-1. On the contrary, in a microenvironment that is lack of or low in HS/HSPGs, ADAMTS-1 is likely cleaved to generate the cleavage fragments that are without the substrate (AR and HB-EGF) binding site(s) and contain unmask the anti-tumor TSP type I motifs.

Example 3

The Pro-Tumor Effect of Full-length ADAMTS-1 and the Anti-tumor Effect of the ADAMTS-1 Fragments Were Confirmed in Lewis Lung Carcinoma (LLC) Cells.

To confirm the effects of full-length ADAMTS-1 and the ADAMTS-1 fragments on tumor growth and metastasis, and compare their effects with that of thrombospondin-1 and -2, LLC transfectants were established that were transfected with empty expression vectors (LLC$_{wtb}$) or expressing full-length ADAMTS-1, ADAMTS-1E/Q, ADAMTS-1$_{NTF}$, ADAMTS-1$_{CTF}$, thrombospondin-1, or -2 (FIG. 13). ADAMTS-1, thrombospondin-1 and -2 are the members of thrombospondin type I repeat superfamily (TRS). Thrombospondin-1 is a 450 kDa homotrimeric ECM protein and is considered as a potent anti-tumor molecule. Studies have shown that systemic injection or overexpression of thrombospondin-1 inhibits the in vivo growth of several tumor cells including LLC cells (70, 78, 79). A subline of LLC cell (LLC$_{wt}$) that undergoes spontaneous pulmonary metastasis after removal of the primary subcutaneous (s.c.) tumors were used to establish these transfectants. LLC$_{wt}$ cells express a low level of endogenous ADAMTS-1 as assessed by RT-PCR and Western blot analysis (data not shown). Five independent clonal LLC transfectants expressing a high to intermediate level of the same gene products were randomly selected, pooled (FIG. 13), and used in the s.c. tumor growth and spontaneous pulmonary metastasis experiments following the established protocols (80-82, 108, 110).

The results showed that expression of full-length ADAMTS-1 promotes while expression ADAMTS-1$_{NTF}$ or ADAMTS-1$_{CTF}$ and to a less extent that of ADAMTS-1E/Q inhibits s.c. growth and spontaneous pulmonary metastasis of the LLC transfectants (FIG. 13). More importantly, even though the LLC transfectants express a higher level of thrombospondin-1 or -2 comparing to that of ADAMTS-1$_{NTF}$ and ADAMTS-1$_{CTF}$, the inhibitory effect derived from the ADAMTS-1 fragments is stronger than that derived from thrombospondin-1 or -2 (FIG. 13), suggesting that the ADAMTS-1 fragments and their derivatives have unique features and a great potential to be used as the potent anti-cancer agents.

The Metalloproteinase Activity in ADAMTS-1NTF is Not Required for Its Anti-tumor Activity:

To investigate whether metalloproteinase activity in ADAMTS-1$_{NTF}$ is required for the anti-tumor activity of ADAMTS-1NTF, a protease-dead ADAMTS-1NTFE/Q mutant was established, in which E386 is switched to Q in the Zinc-binding pocket of the metalloproteinase domain. The expression constructs were used to transfect TA3 mouse mammary carcinoma cells. Three independent positive colonies that express ADAMTS-1NTFE/Q or ADAMTS-1NTF or transfected with the empty expression vectors (FIG. 14) were used in the pulmonary tumor metastasis experiments. Our results showed that ADAMTS-1$_{NTFE/Q}$ behaved like ADAMTS-1$_{NTF}$ and significantly promoted the survival of the experimental mice and inhibited the pulmonary tumor metastasis (FIG. 14). This result suggests that the metalloproteinase domain of ADAMTS-1 does not contribute to the anti-tumor effect of ADAMTS-1$_{NTF}$.

Example 4

The anti-tumor and anti-angiogenic activity of thrombospodin-1 has been well established and the anti-tumor activity has been mapped to the several domains including the TSP type I repeats. All the members of the ADAMTS family contain at least one TSP-1 motif and belong to the thrombospondin type I repeat (TSR) superfamily (73). Since identification of ADAMTS-1 (22), several studies have been performed to investigate the role of ADAMTS-1 in tumor growth and metastasis, and the results obtained appeared to contradict each other. In pancreatic cancer samples, a higher ADAMTS-1 mRNA level was correlate to the severe lymph node metastasis or retroperitoneal invasion and worse prognosis, suggesting that ADAMTS-1 likely promotes pancreatic cancer invasion and metastasis. However, ADAMTS-1 mRNA is down-regulated in the breast carcinoma samples comparing to the nonneoplastic mammary tissues but with no strong links between the ADAMTS-1 mRNA level and the clinicopathological features of these breast cancer cases studied. These studies have only measured ADAMTS-1 mRNA level but not the protein level and the proteolytic activity of ADAMTS-1, both of which are more relevant to the ADAMTS-1 function.

In addition, ADAMTS-1 was found to inhibit tumor growth by blocking tumor angiogenesis, which is likely achieved by sequestering VEGF$_{165}$ from its receptor, and the metalloproteinase activity of ADAMTS-1 is required for the observed anti-angiogenesis and anti-tumor growth activity. In contrast to this finding, overexpressioin of ADAMTS-1 was found to promote subcutaneous growth of the transfected CHO cells but inhibit experimental metastasis of the same transfectants. However, these studies have neither considered the fact that ADAMTS-1 is proteolytically cleaved, nor investigated the cleavage status of ADAMTS-1 in vivo (in subcutaneous and pulmonary microenvironments), and did not consider the possibility that the requirement of the metalloproteinase activity of ADAMTS-1 for its anti-tumor effect may merely reflect to the fact that the anti-tumor effect is actually derived from the auto-proteolytic cleavage fragments but not the full-length ADAMTS-1, and that the metalloproteinase activity of ADAMTS-1 is required for generating these ADAMTS-1 fragments.

To test this possibility, the how and why full-length and the ADAMTS-1 fragments affect tumor growth and metastasis was investigated. As described herein, it is demonstrated that overexpression of full-length ADAMTS-1, which is maintained in the full-length form during metastasis of TA3 mammary carcinoma cells, promotes the tumor metastasis, and that ADAMTS-1 promotes shedding of AR and HB-EGF precursors and activation of EGFR and ErbB-2 in vivo. In addition, for the first time that ADAMTS-1 undergoes auto-proteolytic cleavage to generate the NH$_2$- and COOH-terminal fragments that contain at least one TSP-1 motif is shown. In contrast to that of full-length ADAMTS-1, overexpression of the fragments of ADAMTS-1 (ADAMTS-1$_{NTCF}$ and ADAMTS-1$_{CTCF}$) that mimic the proteolytic cleavage fragments of ADAMTS-1 blocks pulmonary metastasis of TA3 cells by inhibiting tumor cell extravasation, proliferation and survival, and by repressing tumor angiogenesis. It is demonstrated that the anti-metastatic activity of the ADAMTS-1 fragments requires the TSP-1 motif, which is likely masked in the full-length molecule, and that ADAMTS-1$_{NTF}$ and ADAMTS-1$_{CTF}$ inhibit activation of EGFR and ErbB-2 in vivo and inhibits the Erk1/2 kinase activation induced by soluble AR and HB-EGF.

Furthermore, it is demonstrated that the proteolytic cleavage of ADAMTS-1 is blocked by heparin, and HS, suggesting that the binding of ADAMTS-1 to heparan sulfate proteoglycans (HSPGs) masks the auto-proteolytic cleavage site(s) in the spacer/Cys-rich domain and keep ADAMTS-1 in the full-length form to cleave their substrates. On the other hand, the auto-proteolytic cleavage of ADAMTS-1 in the spacer/Cys-rich domain likely destroys the substrate binding sites and unmasks the anti-tumor TSP-1 domain, which renders the anti-tumor activity to the ADAMTS-1 fragments. Thus, the level of HSPGs in the microenvironment likely regulates the form of ADAMTS-1 (full-length or the cleavage fragments) that exists predominantly in the microenvironment to exert pro- or anti-tumor activity, respectively. It is demonstrated that ADAMTS-1 expressed by TA3 cells is maintained in the full-length form in vivo to exert pro-metastasis activity. Thus, the results have reconciled the apparent contradiction in the previous results and demonstrated that the cleavage status of ADAMTS-1 determines its effect (stimulatory or inhibitory) on tumor growth and metastasis.

The results described herein suggested that ADAMTS-1 plays the multiple roles in tumor growth and metastasis and is a prime target for cancer therapy, and that the ADAMTS-1 fragments have great potential as the potent anti-cancer agents that inhibit not only tumor cell proliferation/survival/invasion, but also tumor angiogenesis.

The Pro-Metastatic Activity of Full-Length ADAMTS-1 Requires Its Metalloproteinase Activity To determine whether the metalloproteinase activity of ADAMTS-1 is required for the pro-metastatic activity of ADAMTS-1, TA3 transfectants expressing the protease-dead mutant of ADAMTS-1 (ADAMTS-1E/Q), which harbors an E$_{386}$ to Q point mutation in the Zinc-binding pocket of the metalloproteinase domain were generated. The study has shown that this mutant lacks the catalytic activity.

In order to assess the effects of ADAMTS-1 E/Q on tumor metastasis reliably, the established clonal TA3 cell line, TA3$_{wtl}$, was used. Like its parental cells, TA3$_{wtl}$ cells express ADAMTS-1 endogenously and undergo pulmonary metastasis after intravenous (i.v.) injection. Five independent clonal TA3 transfectants expressing a high to intermediate level of ADAMTS-1E/Q were randomly selected and used as the pooled population (TA3$_{ADAMTS-1E/Q}$, FIG. 5B) in the pulmonary metastasis experiments. Five independent clonal TA3 transfectants transfected with the empty expression vectors or expressing the following same gene products were used as the pooled population as well: full-length ADAMTS-1 (TA3$_{ADAMTS-1}$), ADAMTS-1$_{NTF}$ (TA3$_{ADAMTS-1NTF}$), ADAMTS-1$_{CTF}$ (TA3$_{ADAMTS-1CTF}$), and ADAMTS-1$_{minusTSP-1}$ (TA3$_{ADAMTS-1minusTSP-1}$). These pooled TA3 transfectants express a similar level of the transfected gene products (FIG. 5B) and displayed a similar growth rate in the cell culture condition with 10% FBS (data not shown).

Figure 5:
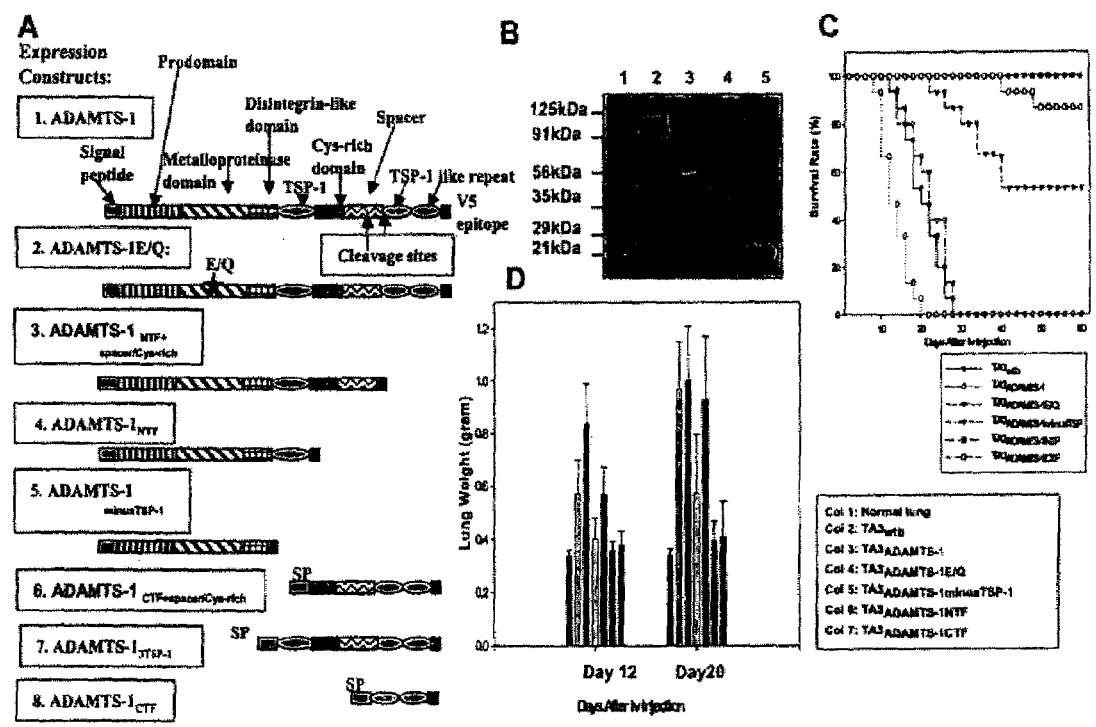
FIG. 5, Panels A through D. Full-length ADMATS-1 promotes pulmonary metastasis of TA3 cells, while ADAMTS-1E/Q, ADAMTS-1$_{NTF}$, or ADAMTS-1$_{CTF}$ inhibits the process. A. Schematic diagram of the domain organization of full-length ADAMTS-1 and the different deletional and point-mutated ADAMTS-1 that were used in FIGS. 1, 2, 3, and 8. B. The expression levels of full-length ADAMTS-1 (lane 1), ADAMTS-1E/Q (lane 2), ADAMTS-1$_{NTF}$ (lane 3), ADAMTS-1$_{minusTSP-1}$ (lane 4), or ADAMTS-1$_{CTF}$ (lane 5) by the pooled populations of TA3 transfectants. C. Survival rates of the experimental mice which were injected with the different TA3 transfectants intravenously. A total of 12 mice were used for each type of transfectants. D. Pulmonary metastatic burden was expressed by the weight of the tumor bearing mouse lungs derived from the experimental mice 12 and 20 days after the i.v. injection of the TA3 transfectants.

It was confirmed that the expression of full-length ADAMTS-1 promotes the pulmonary metastasis of TA3 cells and shortens the survival time of the mice, while ADAMTS-1$_{NTF}$ or ADAMTS-1$_{CTF}$, but not ADAMTS-1$_{minusTSP-1}$ blocks the pulmonary metastasis of the transfectants (FIGS. 5C-D). In addition, the expression of ADAMTS-1E/Q inhibits the pulmonary metastasis of the transfectants and extends the survival time of the mice (FIGS. 5C-D), suggesting that the metalloproteinase activity is required for the pro-metastatic activity of full-length ADAMTS-1. The metastatic burden was quantified by the average weight of the experimental mouse lungs (FIG. 5D). Because there is a significant difference in the survival time of the experimental mice which succumb to pulmonary metastasis when metastatic burden causes the lung weight to reach 1-1.2 grams, the metastatic burden was measured in the remaining survival mice at day 12 and 20 after i.v. injection of these TA3 transfectants. At least 12 mouse lungs were weighted for each type of the transfectants at each time point. We confirmed that overexpression of full-length ADAMTS-1 accelerated the time that is required to reach the maximal metastatic burden and shortened the survival time of the mice, while overexpression of ADAMTS-1E/Q, ADAMTS-$1_{NTF}$, or ADAMTS-$1_{CTF}$ but not ADAMTS-$1_{minusTSP-1}$ reduced the metastatic burden (FIG. 5D). Furthermore, it was demonstrated that the inhibitory effect derived from ADAMTS-$1_{NTF}$ or ADAMTS-$1_{CTF}$ is stronger than that derived from ADAMTS-1E/Q, implying that the underlying mechanisms for their anti-metastatic effects may be different. This hypothesis was supported by the results obtained previously, which indicated that ADAMTS-1E/Q but not ADAMTS-$1_{NTF}$ and ADAMTS-$1_{CTF}$ serves as a dominant negative regulator of full-length endogenous ADAMTS-1 by inhibiting the shedding of HB-EGF and AR transmembrane precursors (FIG. 3). Together, these data suggest that like full-length ADAMTS-1, the anti-tumor TSP-1 domains in ADAMTS-1E/Q are masked, and that the anti-tumor activity is likely derived from the intact spacer/Cys-rich domain, which competes with ADAMTS-1 for the binding to its substrates.

Figure 6:
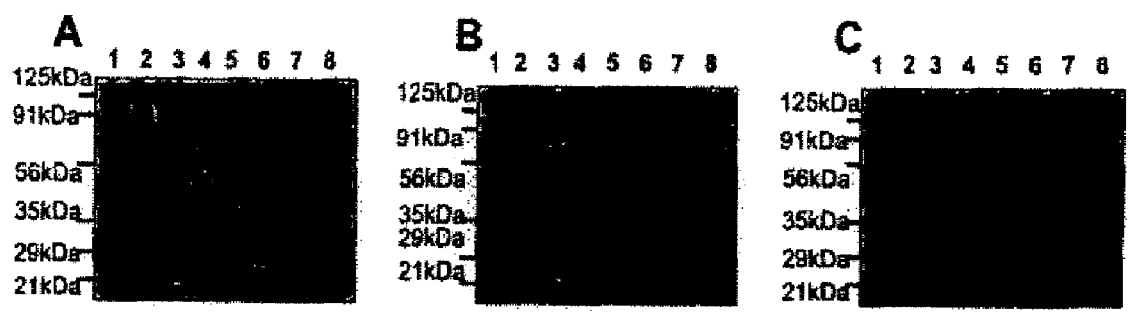
FIG. 6, Panels A-C. The spacer/Cys-rich domain of ADAMTS-1 plays a major role in binding of ADAMTS-1 to the ECM and the cells. Western blotting was performed using anti-v5 antibody to determine the distribution patterns of the v5-epitope tagged full-length ADAMTS-1 (lane 1), ADAMTS-1E/Q (lane 2), ADAMTS-1$_{NTF+spacer/cys-rich}$ (lane 3), ADAMTS-1$_{NTF}$ (lane 4), ADAMTS-1$_{minusTSP-1}$ (lane 5), ADAMTS-1$_{CTF}$ (lane 6), ADAMTS-1$_{CTF+spacer}$ (lane 7), and ADAMTS-1$_{3TSP-1}$ (lane 8) in the cell culture supernatants (A), the ECM materials (B), and the EDTA-lifted Cos-7 cells (C) that were transfected with the corresponding expression constructs.

The Spacer/Cys-Rich Domain is Essential for Binding of ADAMTS-1 to the Cell Surface and the ECM The ADAMTS-1 substrates identified so far are versican, aggrecan, and HB-EGF and AR precursors, which are located on the ECM and the cell surface, respectively. To determine the domain(s) of ADAMTS-1 that mediate(s) the substrate binding, we first assess the ECM and the cell binding capacity of the different deletional mutants of ADAMTS-1 (see FIG. 5A). All the constructs contain the COOH-terminal v5-epitope tags for easy identification and purification, and the constructs were transfected into COS-7 cells. 72 hours after the transfection, the proteins derived from the cell culture supernatants, the ECM materials deposited by the transfected cells, and the lysates of the transfected cells were analyzed by Western blotting with anti-v5 epitope antibody as described (106, 109). The results showed that the spacer/Cys-rich domain is essential for the binding of ADAMTS-1 to the ECM and the cells (FIG. 6), suggesting that the spacer/Cys-rich domain likely mediates the substrate binding of ADAMTS-1.

ADAMTS-1 Promotes Invasion of TA3 Cells Through Matrigel

It is well established that the pericellular proteolysis mediated by MMPs is essential for tumor invasion. As a member of the $Zn^{2+}$-dependent metalloproteinase family, ADAMTS-1 plays an important role in degrading versican, an important component of the ECM and the blood vessel walls. We have shown that ADAMTS-1 promotes extravasation of TA3 cells into lung parenchyma (FIG. 3). To determine how full-length ADAMTS-1 and the fragments of ADAMTS-1 affect tumor cell invasion through Matrigel which mimics the basement membrane as the barriers of tumor cell invasion, an invasion assay by using Transwell cell culture chambers with 8-μm pores (Costar) coated with a layer of Matrigel Collaborative Biomedical) was performed. The DMEM containing 2% FBS was be added into the lower chambers of the Transwells. $2 \times 10^5$ of the different TA3 transfectants were seeded on top of the Transwell in triplicate and incubated for 24 hours. The bottom filters were then be fixed and stained. The cells on the top chambers were removed by wiping with cotton swabs, and the stained cells (blue color) that have migrated through the Matrigel were counted under a microscope. Six randomly selected 100× microscopic fields will be countered. The invasion index of the different TA3 transfectants was calculated as following formula:

Invasion Index=100%×(Average number of cells in lower chamber/microscopic field/numbers of cells seeded on upper chamber/microscopic field).

The results showed that $TA3_{ADAMTS-1}$ cells displayed approximately two time higher invasion index than $TA3_{wtl}$ and $TA3_{ADAMTS-1minusTSP-1}$ cells, and four-eight time higher invasion index compared to $TA3_{ADAMTS-1NTF/TA3}/TA3_{ADAMTS-1CTF}$ and $TA3_{ADAMTS-1E/Q}$ cells, respectively. These results further confirmed that ADAMTS-1 promotes tumor cell invasion, while $TA3_{ADAMTS-1E/Q}$ and to a less extent $TA3_{ADAMTS-1NTF}$, or $TA3_{ADAMTS-1CTF}$ inhibits the process. To determine whether ADAMTS-1 promotes TA3 cell invasion by degrading versican or inhibiting the pro-migratory effect of soluble HB-EGF and AR, the confluence TA3 transfectants were lifted by the EDTA solution and the ECM materials remained on the cell culture dishes were extracted and analyzed by Western blotting with anti-DP antibody, which detects the cleavage fragments of versican. The result showed that increased expression of exogenous ADAMTS-1 but not ADAMTS-$1_{minusTSP-1}$ on top of the endogenous ADAMTS-1 promotes degradation of versican, while expression of ADAMTS-1 E/Q but not ADAMTS-$1_{NTF}$, ADAMTS-$1_{CTF}$ inhibits the degradation. These data suggest that ADAMTS-1E/Q inhibits TA3 cell invasion by blocking the ADAMTS-1 mediated versican degradation, while the weaker inhibitory effect of the ADAMTS-1 fragments is likely derived from their indirect effect on activity of HB-EGF/AR.

Example 5

Following the experimental procedures described in Example 1, addition data was generated showing additional differences between full length ADAMTS-1 and its cleavage products, ADAMTS-$1_{NTCF}$ and ADAMTS-$1_{CTCF}$. Overexpression of ADAMTS-1 promotes growth of TA3 mammary carcinoma (TA3) cells while overexpression of the N- or C-terminal fragment of ADAMTS-1 blocks growth of TA3 cells by inhibiting proliferation and inducing apoptosis of the tumor cells and by inhibiting tumor angiogenesis. ADAMTS-1 expressed by TA3 cells maintained in the full-length form in vivo exerted pro-tumor growth and metastasis activity. In contrast to the of full-length ADAMTS-1, overexpression of the N- or C-terminal fragment of ADAMTS-1 (ADAMTS-$1_{NTCF}$ and ADAMTS-$1_{CTCF}$) inhibits subcutaneous (s.c.) growth of TA3 cells. In addition, unlike full-length ADAMTS-1 which promotes shedding of the EGF family ligands including amphiregulin (AR) and heparin-binding EGH (HB-EGF) and activation of EGF receptor (EGFR) and ErbB-2, the ADAMTS-1 fragments inhibits activation of EGFR and ErbB-2 in vivo.

Figure 7:
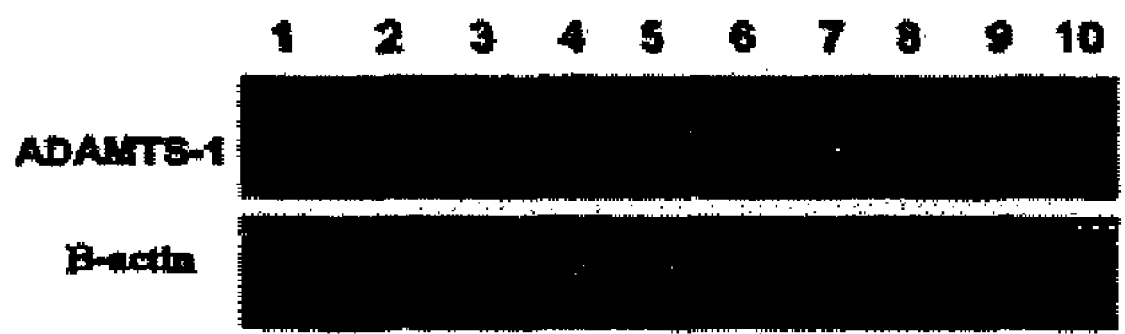
FIG. 7. Expression of ADAMTS-1. Expression of ADAMTS-1 was assessed by RT-PCR using RNAs derived from TA3$_{wt}$, TA3$_{wtl}$, Lewis lung carcinoma cells, CMT-93 colon carcinoma cells, B16F1 and F10 cells, 3T3 fibroblasts, C$_2$C$_{12}$ myoblasts, and mouse placenta (lanes 2-10). Expression of β-actin by these cells was used as controls. In lane 1, reverse transcriptase was not included in RT reaction with RNA derived from TA3$_{wtl}$ cells.
Figure 8:
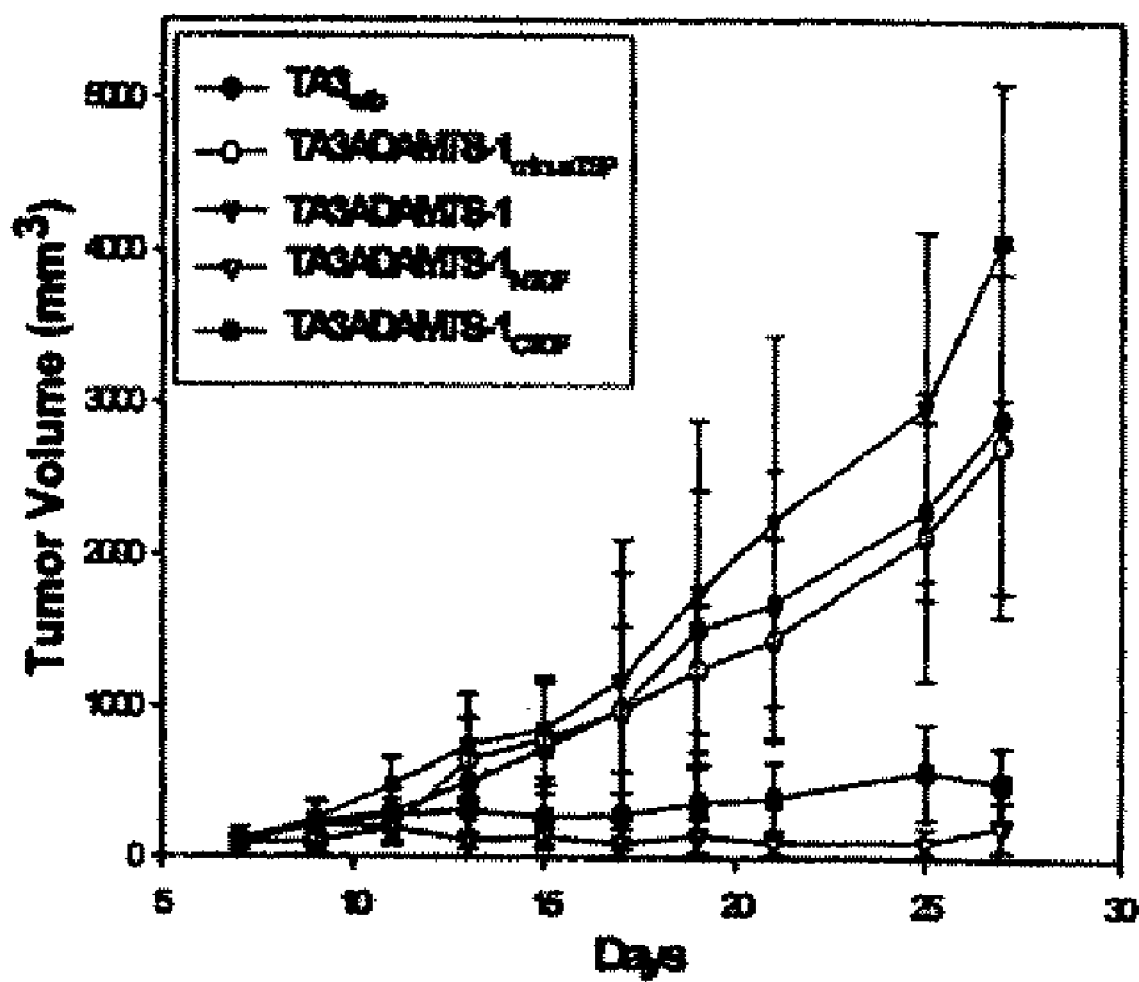
FIG. 8. ADAMTS-1 promotes tumor growth while the cleavage fragments of ADAMTS-1 inhibit tumor growth. Growth rates of the s.c. tumors derived from different TA3 transfectants are expressed as the means of tumors volumes±SD. Total of fifteen mice were used for each type of transfectants.

RT-PCR results showed that like wild type TA3 cells, $TA3_{wtl}$ cells express ADAMTS-1 endogenously as do several other tumor cell lines (FIG. 7). Growth rates of the s.c. solid tumors derived from different TA3 transfectants were measured and the result showed that overexpression of ADAMTS-1 promotes tumor growth, while overexpression of ADAMTS-$1_{NTCF}$ and ADAMTS-$1_{CTCF}$, but not that of ADAMTS-$1_{minusTSP}$ significantly inhibits tumor growth (FIG. 8). These results suggest that the inhibitory effect of the ADAMTS-1 fragments is likely derived from the TSP type I motifs, which exist in ADAMTS-$1_{NTCF}$ and ADAMTS-$1_{CTCF}$, but not in ADAMTS-$1_{minusTSP}$. The data show that ADAMTS-$1_{NTCF}$ or ADAMTS-$1_{CTCF}$, blocks pulmonary metastasis of TA3ADAMTS-$1_{NTCF}$ or TA3ADAMTS-$1_{CTCF}$ cells. The metastatic burden of the experimental mice was quantified by average weight of the experimental mouse lungs received different TA3 transfectants. Results showed that overexpression of ADAMTS-$1_{NTCF}$ or ADAMTS-$1_{CTCF}$ dramatically reduced metastatic burden of the mice received the corresponding TA3 transfectants, and render most of the experimental mice free of metastatic disease and significantly extended survival time of these mice.

Figure 9:
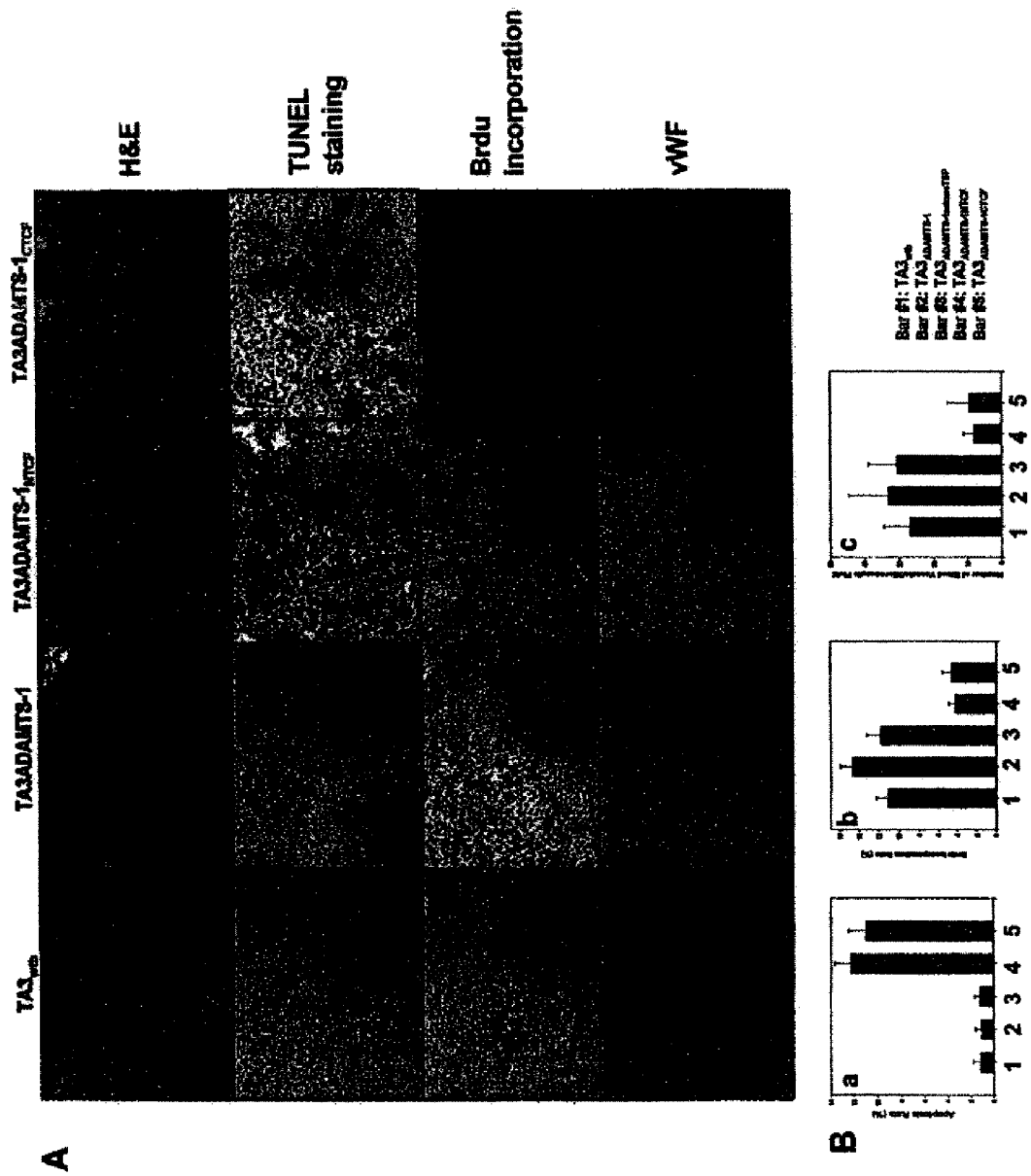
FIG. 9. Panels A and B. The cleavage fragments of ADAMTS-1 blocks subcutaneous tumor growth by inhibiting proliferation and survival of tumor cells, and inhibiting tumor angiogenesis in vivo. The s.c. tumors were section 12 days after implanting TA3$_{wtb}$(A, a-d), TA3ADAMTS-1 (A, e-h), TA3ADAMTS-1$_{NTCF}$ (A, i-l), and TA3ADAMTS-1$_{CTCF}$ (A, m-p). These sections were stained with H&E (A-a, e, I, m), or reacted with Apoptag to detect apoptotic tumor cells in situ (A-b, f, j, n), anti-Brdu antibody to detect proliferating tumor cells (A-c, g, k, o), or with anti-vWF antibody to reveal blood vessels with the tumors (a-d, h, l, p). Bar: 120 μm. The quantitative data that reveals the effects of ADAMTS-1 and the fragments of ADAMTS-1 on tumor cell apoptosis and proliferation in vivo and on tumor angiogenesis are shown in panels B-a, b, c, respectively.

The ADAMTS-1 fragments blocks tumor growth by inhibiting proliferating and inducing apoptosis of tumor cells, and inhibiting tumor angiogenesis. To determine the cellular basis of the pro-tumor effect of full-length of ADAMTS-1 and the anti-tumor effect of ADAMTS-1 fragments, proliferation and apoptosis rates of the tumor cells and tumor angiogenesis during s.c. growth were analyzed. Brdu (5-Bromo-2'-deoxy-uridine) incorporation assay and in situ detection of apoptotic cells were performed on the sections derived from s.c. solid tumors (twelve days after implanting the TA3 cells). Results demonstrated that expression of ADAMTS-$1_{NTCF}$ and to a less extent that of ADAMTS-$1_{CTCF}$, but not expression of ADAMTS-$1_{minusTSP}$, inhibits proliferation and promotes apoptosis of the tumor cells, and inhibits angiogenesis in the subcutaneous space; while expression of exogenous ADAMTS-1 mildly enhances proliferation rate and reduces apoptosis rate of the tumor cells, and promotes tumor angiogenesis in vivo (FIG. 9) These results suggest that ADAMTS-1 may play an important role in releasing/activating growth/survival factors in the microenvironments, while the cleavage fragments of ADAMTS-1 may block the activities of the factors that promote tumor cell proliferation and survival and tumor angiogenesis.

Figure 10:
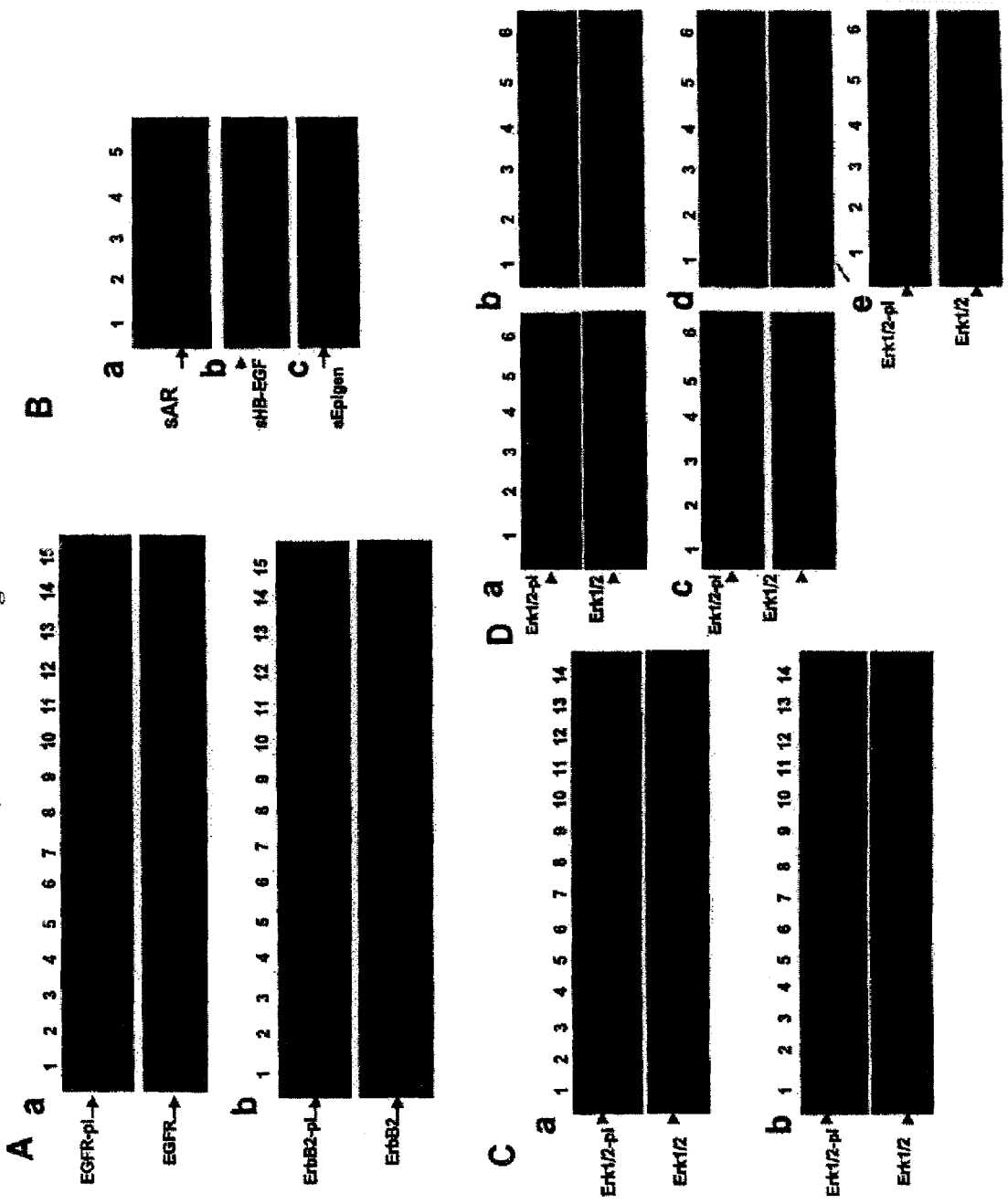
FIG. 10, Panels A through D. The ADAMTS-1 fragments block activation of EGFR and ErbB-2; while ADAMTS-1 promotes shedding of AR and HB-EGF. A. Immunoprecipitation with anti EGFR (A-a) or anti-ErbB-2 (A-b) antibody was performed by using the proteins derived from the mouse lungs received TA3$_{wtb}$ (lanes 1-3), TA3ADAMTS-1 (lanes 4-6), TA3ADAMTS-1$_{minusTSP}$ (lanes 7-9), TA3ADAMTS-1$_{NTCF}$ (lanes 10-12), and TA3ADAMTS-1$_{CTCF}$ (lanes 13-15) intravenously 5 days prior. The precipitated proteins were analyzed Western blotting with anti-phospho-tyrosine antibody to detect phosphor-EGFR (A-a, upper panel) and phosphor-ErbB-2 (A-b, upper panel), respectively or with anti-EGFR (A-a, bottom panel) or anti-ErbB-2 (A-b, bottom panel) antibody to detect total amount of EGFR or ErbB-2, respectively. B. ADAMTS-1 promotes shedding of AR (B-a), HB-EGF (B-b), but not epigen (B-c), and the shedding is blocked by ADAMTS-1E/Q (lane 4). Cos-7 cells were co-transfected with the expression constructs containing cDNA inserts that encode the EGF family ligand precursors with or without (lane 1) of TA3ADAMTS-1$_{NTCF}$ (lane 2), TA3ADAMTS-1$_{CTCF}$ (lane 3), ADAMTS-1E/Q (lane 4), and ADAMTS-1 (lane 5). C. The cell culture supernatants derived from the AR-(C-a) or HB-EGF (C-b) transfected Cos-7 cells were applied to serum-starved MCF-10A cells without (lane 5-6) or without prior absorption of the supernatants with blocking antibodies against AR (a, lane 7-8) or HB-EGF (b, lane 7-8) in the presence of 400 ng of ADAMTS-1 (lane 9-10), ADAMTS-1$_{NTCF}$ (lane 11-12), or ADAMTS-1$_{CTCF}$ (lane 13-14). Serum free medium alone (lane 1-2) or containing 5 ng of AR (a, lane 3-4) or 4 ng of HB-EGF (b, lane 3-4) was applied to serum starved MCF-10A cells. Equal amount of the proteins derived from the MCF-10A cells were analyzed by Western blotting with anti-phospho-Erk1/2 to detect phosphor-Erk1/2 or with anti-Erk antibody to detect total amount of Erk1/2. D. The cleavage fragments of ADAMTS-1 blocks activation of Erk1/2 in HUVECs induced by VEGF 165 (D-a), TGF-.alpha. (D-c), HB-EGF (D-d), and AR (D-e), but not that induced by bFGF (D-b). HUVECs were applied with SFM alone (lane 1) or containing different GFs alone (lane 2) with 400 ng of ADAMTS-1 (lane 3), ADAMTS-1$_{minusTSP}$ (lane 4), ADAMTS-1$_{NTCF}$ (lane 5) or ADAMTS-1$_{CTCF}$ (lane 6). Equal amount of the proteins derived from HUVECs were analyzed Western blotting with anti-phospho-Erk1/2 to detect phosphor-Erk1/2 or with anti-Erk antibody to detect total amount of Erk1/2.
Figure 11:
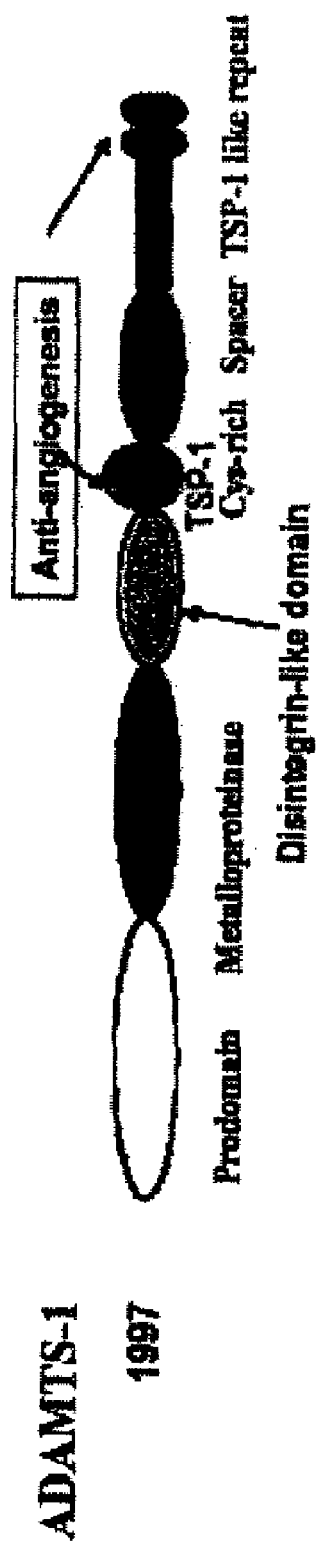
FIG. 11. Domain organization of ADAMTS-1. The various domains of ADAMTS-1 are shown.
Figure 12:
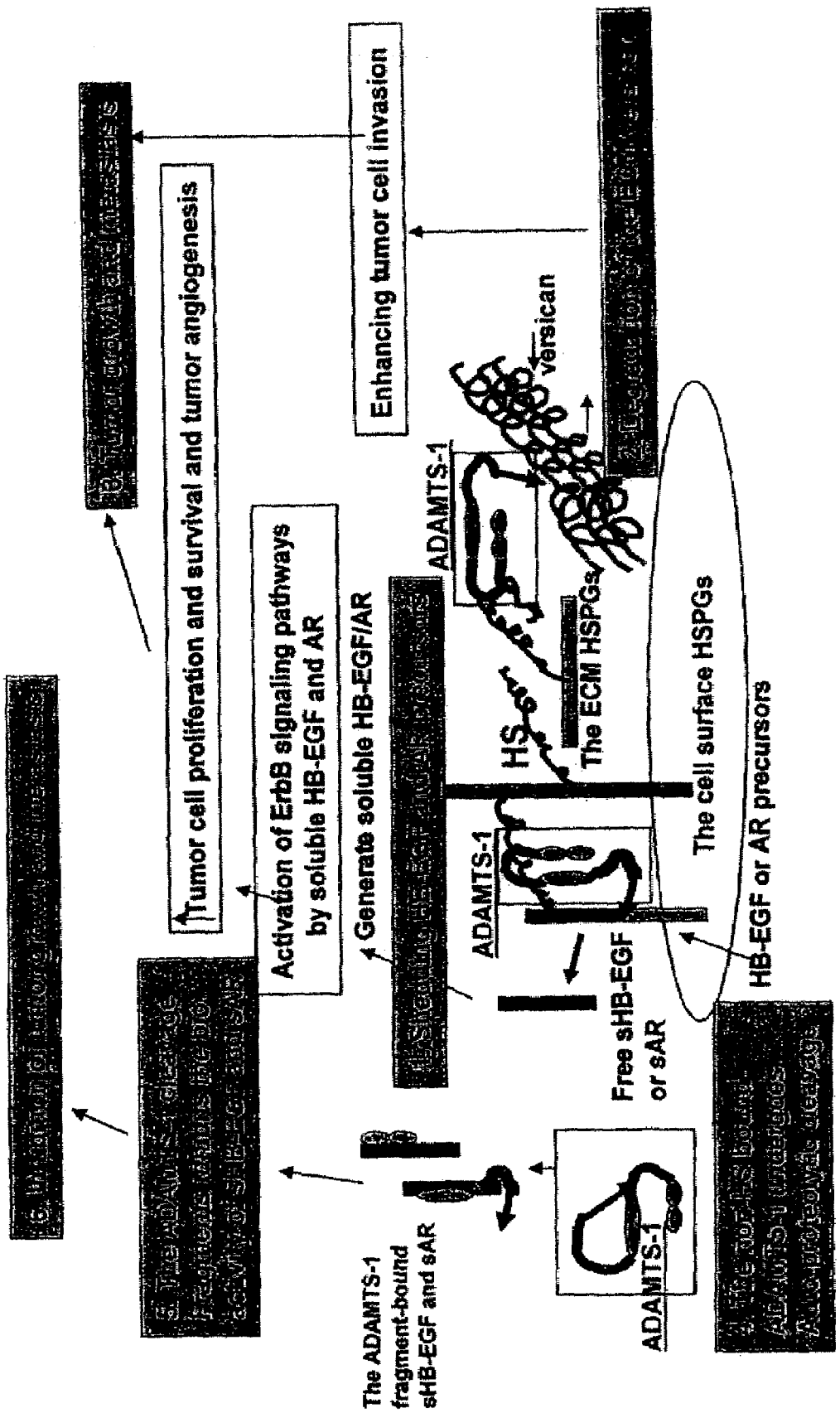
FIG. 12. Possible mechanisms of ADAMTS-1 function. 1)Full-length ADAMTS-1 promotes tumor growth and metastasis by enhancing tumor cell proliferation/survival and tumor angiogenesis through shedding/activating HB-EGF and AR transmembrane precursors and by promoting tumor cell invasion through degrading versican; 2) full-length ADAMTS-1 binds to their substrates through its spacer/Cys-rich domain directly or indirectly through binding to HSPGs. Thus, the whole or different parts of the spacer/Cys-rich domain can be used as a dominant negative regulator of the full-length ADAMTS-1 (by regulating the substrate-binding of ADAMTS-1) and to regulate its own cleavage status (to promote proteolytic cleavage of ADAMTS-1, therefore generate anti-tumor fragments); 3) the anti-tumor activity of the ADAMTS-1 fragments resides in the TSP-1 domains, which exerts the anti-tumor activity by inhibiting bioactivity of several soluble heparin binding growth/angiogenic factors including AR and HB-EGF. Thus, the whole or parts of ADAMTS-1NTF (ADAMTS-1NTFE/Q) and/or ADAMTS-1CTF can be used to inhibit cancers.

Activation of EGFR and ErbB-2 is known to promote proliferation and survival of breast carcinoma cells and play essential roles in progression of breast cancers. To determine whether activation of EGFR and/or ErbB-2 underlies the pro-tumor activity of ADAMTS-1, we assessed activity of EGFR and ErbB-2 in the lungs where TA3$_{wtb}$, TA3$_{ADAMTS-1}$, TA3ADAMTS-$1_{NTCF}$, TA3ADAMTS-$1_{CTCF}$, or ADAMTS-$1_{minusTSP}$ cells were injected five days prior. The result showed that expression of ADAMTS-1 by TA3 cells promotes activation of EGFR and ErbB-2 in vivo (FIG. 10, A). On the contrary, expression of ADAMTS-$1_{NTCF}$ or ADAMTS-$1_{CTCF}$, but not ADAMTS-$1_{minusTSP}$ which lacks TSP type I motifs, blocks activation of EGFR and ErbB-2 in vivo (FIG. 13, A).

Experiments were done to assess whether induces activation of EGFR and ErbB-2 by ADAMTS-1 is achieved via promoting shedding EGF family ligands. EGF family ligands are produced as transmembrane precursors, which are shed and released from cell surface as soluble mature form. Several EGF family ligands are known to be shed-activated by the ADAM family proteinases including ADAM-17. However, studies using the cells derived from ADAM-17 null-mouse suggested that ADAM-17 is not the sole proteinase that is responsible for shedding of TGF-.alpha. and other member(s) of ADAM family is (are) likely to play a role as well. To determine whether ADAMTS-1 play a role in shedding EGF family ligands especially the ones that bind to heparin, several EGF family ligands were co-transfected including HB-EGF, TGF-.alpha., AR, and epigen which are expressed by TA3 cells (data not shown) with or without the full-length ADAMTS-1, ADAMTS-1E/Q and the ADAMTS-1 fragments. The serum-free cell culture medium of the transfected cells were collected and concentrated and analyzed. The results showed that ADAMTS-1 promotes shedding of AR and HB-EGF but not shedding of TGF-.alpha. and epigen; while ADAMTS-1E/Q blocks the shedding. The ADAMTS-1 fragments displayed no effect on the shedding (FIG. 10, B and data not shown).

To determine whether the ADAMTS-1 fragments affect the signal transduction pathways activated by HB-EGF and AR, the serum-free cell culture media (SFM) derived from the co-transfected cells were applied to MCF-10A mammary epithelial cells to determine their ability to induce Erk1/2 kinase activation. The results showed that soluble HB-EGF and AR in the SFM induces activation of Erk1/2 kinases, which is specifically blocked by the corresponding blocking antibodies or the ADAMTS-1 fragments, but not by the full-length ADAMTS-1 (FIG. 10, C). This result suggests that the ADAMTS-1 fragments inhibit activation of EGFR and ErbB-2 by interfering with their ligand activity; and the effects of ADAMTS-1 and its cleavage fragments on the availability and activity of EGF family ligands likely underlies their roles in tumor growth and metastasis.

The affect the fragments have on activities of several important growth/angiogenic factors that are known to regulate angiogenesis was investigated. Activity of VEGF$_{165}$, bFGF, HB-EGF, TGF-α, and AR were revealed by their ability to induce activation of Erk1/2 kinases in HUVECs in the presence or absence of different purified ADAMTS-1 proteins. Results showed that ADAMTS-$1_{NTCF}$ and ADAMTS-$1_{CTCF}$ but not full-length ADAMTS-1 or ADAMTS-$1_{minusTSP}$ block activation of Erk1/2 kinase induced by VEGF$_{165}$, TGF-α, HB-EGF, and AR ADAMTS-1 is widely expressed by tumor cells and undergoes auto-proteolytic cleavage. In addition, overexpression of ADAMTS-1 promotes tumor growth and metastasis by enhancing tumor cell proliferation and survival and by promoting tumor angiogenesis through shedding transmembrane EGF family ligands, AR and HB-EGF, which in turn promotes activation of EGFR and ErbB-2 in vivo.

The results not only provided a potential important target (full-length ADAMTS-1), potent novel anti-cancer reagents (the ADAMTS-1 fragments), and the regulatory reagents for ADAMTS-1 activity (HS/HSPGs) for the treatment of cancers especially breast cancers in the figure, but also revealed the mechanism underlying the function of ADAMTS-1 and the ADAMTS-1 fragments.

The presence of TSP type I motif is a common feature of all members of ADAMTS family, among them ADAMTS-1, -4, AND -12 undergo proteolytic cleavage at their spacer/Cys-rich region, which have potential to generate ADAMTS fragments containing unmasked TSP type I motifs that may possess anti-tumor activity. In addition, as indicated in this study, the auto-proteolytic cleavage may be a general mechanism that regulates the function of ADAMTS family members. Additional work is required to verify these hypotheses and the results obtained in this study provide general rules that may apply the other ADAMTS family members as well.

For subcutaneous tumor growth experiments, five independent clonal TA3 transfectants expressing ADAMTS-1, ADAMTS-1$_{CTCF}$, ADAMTS-1$_{NTCF}$ or ADAMTS-1$_{minusTSP}$, or transfected with the empty expression vector were used in the in vivo experiments. For each type of the experiment, six mice were injected with each clonal transfectants and two independent experiments were performed.

In tumor growth experiments, TA3 transfectants were injected subcutaneously into syngenic A/Jax-mice as described. After solid tumors became visible (7-10 days after the injection), the tumors were measured by a digital caliper every other day for the next two weeks. The largest and shortest diameters of the solid tumors were measured. The tumor volume was calculated by using the following formula: tumor volume=½×(shortest diameter)$^2$×longest diameter (mm$^3$).

Example 6

Determining the Exact Amino Acid Segments in the TSP-1 Domains Containing Anti-Cancer Activity As discussed herein, the ADAMTS-1 fragments that contain either the middle TSP-1 motif (ADAMTS-1$_{NTF}$) or the two COOH-terminal TSP-1modules (ADAMTS-1$_{CTF}$) inhibit growth and/or metastasis of TA3 and LLC, and their inhibitory effect is much stronger than that caused by thrombospondin-1 and -2, suggesting the unique molecular basis underlying the potent inhibitory effect of the ADAMTS-1 fragments is not present in thrombospondin-1 and -2. Also, the TSP-1 domain is required for the anti-tumor activity of ADAMTS-1$_{NTF}$. The middle TSP-1 domain (mTSP-1, amino acids 546-596) in ADAMTS-1 is similar but not identical to the second and third TSP-1 repeats (WXXWXXW) in thrombospondin-1, which have been shown to contain anti-tumor and anti-angiogenic activity (102, 111-113). Even though the COOH-terminal TSP-1 modules (cTSP-1, amino acid 842-895 and 896-951, of ADAMTS-1 do not have high homology to the TSP-1 repeats in thrombospondin-1, the ADAMTS-1 fragments that contain either the mTSP-1 or cTSP-1 domain exhibited the similar anti-tumor activity, implying that the common unidentified unique amino acid segments or three dimension feature (other than the WXXWXXW) in the m/cTSP-1 domains of ADAMTS-1 may be essential for the potent anti-tumor activity. Accordingly, the molecular basis for the potent anti-tumor activity that is unique to the ADAMTS-1 fragments can be identified using this domain. To achieve that, deletions in the TSP-1 domains of ADAMTS-1 can be made and tumor growth and metastasis assays can be performed using TA3 and LLC transfectants expressing these ADAMTS-1 mutants (as described herein).

To Determine Whether the $_{m\ and/or\ c}$fTSP-1 Domain Displays Anti-tumor Activity It was shown that deletion of the middle TSP-1 (mTSP-1) domain from ADAMTS-1$_{NTF}$ (ADAMTS-1$_{minusTSP-1}$) abolishes the potent anti-tumor activity of the fragment, suggesting the anti-tumor activity resided in the mTSP-1 domain and that the ADAMTS-1$_{CTF}$ is composed of the two COOH-terminal TSP-1 (cTSP-1) domains. Thus, whether the mTSP-1 domain and each of the cTSP-1 domains display as potent anti-tumor activity as the ADAMTS-1$_{NTF}$ and ADAMTS-1$_{NTF}$ fragments need to be determined. To achieve that, three expression constructs can be generated that contain the signal peptide plus the mTSP-1 domain (fADAMTS-1$_{mTSP-1}$), the first cTSP-1 (fADAMTS-1$_{cTSP-1-1}$), or the second cTSP-1 (fADAMTS-1$_{cTSP-1-2}$) domain in pEF/6/v5-His expression vectors. They can be used to transfect TA3wtl and LLCwtl cells. Five independent TA3 or LLC transfectants expressing a high to intermediate level of fADAMTS-1mTSP-1, fADAMTS-1cTSP-1-1 or fADAMTS-1cTSP-1-2 will be randomly selected and used as the pooled populations together with the established TA3 and LLC transfectants expressing a similar level of ADAMTS-1CTF or ADAMTS-1$_{NTF}$, or transfected with the expression vector alone in the s.c. tumor growth and metastasis experiments.

mTSP-1 domain inhibits growth and metastasis of TA3 and LLC cells in a similar extent as that of ADAMTS-1$_{NTF}$; while expression of each of the cTSP-1 domains display a weaker anti-tumor effect compared to that caused by ADAMTS-1$_{CTF}$, which contains two TSP-1 modules. These small recombinant proteins (53-56 amino acid long) are used as anti-cancers agents.

Deletions and Mutations in the m or cTSP-1 Domains of ADAMTS-1 and Establish TA3 and LLC Transfectants Expressing These ADAMTS-1 Mutants Within in the TSP type I repeats of thrombospondin-1, in addition to WXXWXXW motif, the CSVTCG motif, which binds to CD36, has been shown to contain anti-tumor and anti-angiogenic activity. The $_{m/cTSP-1}$ domains of ADAMTS-1 contain the motifs that are similar to WXXWXXW and/or CSVTCG motifs. In addition, the consensus motif search (GCG genomics) has demonstrated that the most consensus motif among the m and cTSP-1 domains of ADAMTS-1 is the WGE/DCSKTC motif (FIG. 15). Thus, three deletions in $_{m/cTSP-1}$ domains are made: WGPWGP-WGD (ADAMTS-1$_{mTSP-1WXXWEdel}$) or WV/QI/VEIGE/DWG/S (ADAMTS-1$_{cTSP-1WXXXXWdel}$), WGDCSRTC (ADAMTS-1$_{mTSP-1WGdel}$) or WG/SE/PCSKTC (ADAMTS-1$_{cTSP-1WG/Sdel}$), CSRTCGGG (ADAMTS-1$_{mTSP-1CSdel}$) or CSKTCGS/KG (ADAMTS-1$_{cTSP-1CSdel}$, FIG. 15).

The deletional mutagenesis are performed as described using fADAMTS-1$_{mTSP-1}$ and fADAMTS-1$_{cTSP-1-1}$, or fADAMTS-1$_{cTSP-1-2}$ (in pEF/6/v5-His expression vectors) as the templates. These expression constructs are used to transfect Cos-7 cells transiently to assess the expression capacity of these v5-epitope tagged fragments. All the deletional mutants are established in cell lines and their proper expression in Cos-7 cells is demonstrated. These deletional constructs are used to transfect TA3$_{wtl}$ and LLC$_{wtl}$ cells. Five independent TA3 or LLC transfectants expressing a high to intermediate level of each of the mutants are used as the pooled populations in the s.c. tumor growth and metastasis experiments together with the established TA3 and LLC transfectants expressing ADAMTS-1$_{NTF}$, ADAMTS-$_{CTF}$, fADAMTS-1$_{mTSP-1}$ and fADAMTS-1$_{cTSP-1-1}$, or fADAMTS-1$_{cTSP-1-2}$, or transfected with the expression vector alone (the control).

The disclosures of each and every patent, patent application, publication, and accession number cited herein are hereby incorporated herein by reference in their entirety. The appended sequence listing is hereby incorporated herein by reference in its entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated polypeptide fragment of ADAMTS-1 that inhibits growth and/or metastasis of solid tumors overexpressing epidermal growth factor (EGF) family ligands or solid tumors with activated erbB-signaling pathways, wherein the fragment is selected from the group consisting of SEQ ID NOs: 5, 7, 9, and 11.

2. A pharmaceutical composition comprising a polypeptide of claim 1.

3. A composition comprising two or more different polypeptide fragments of ADAMTS-1 that inhibit cell proliferation or metastasis of solid tumors overexpressing EGF family ligands or solid tumors with activated erbB-signaling pathways, wherein said different fragments are selected from the group consisting of SEQ ID NOs: 5, 7, 9, and 11.

4. The composition of claim 3 wherein said composition is a pharmaceutical composition.

5. A method inhibiting growth and/or metastasis of solid tumors overexpressing epidermal growth factor (EGF) family ligands or solid tumors with activated erbB-signaling pathways in an individual comprising administering to the individual a therapeutically effective amount of a composition of claim 2.

6. The isolated polypeptide fragment of claim 1, wherein said fragment inhibits mammary carcinoma tumor growth and/or metastasis.

7. The composition of claim 3, wherein said composition inhibits cell proliferation or metastasis of a mammary carcinoma.

8. The isolated polypeptide fragment of claim 1, wherein said fragment inhibits growth and/or metastasis of tumors overexpressing heparin-binding EGF or amphiregulin.

9. The composition of claim 3, wherein said composition inhibits cell proliferation or metastasis of a tumors overexpressing heparin-binding EGF or amphiregulin.

10. A method of inhibiting growth and/or metastasis of solid tumors overexpressing epidermal growth factor (EGF) family ligands or solid tumors with activated erbB-signaling pathways in an individual comprising administering to the individual a therapeutically effective amount of a composition of claim 4.

11. The method of claim 10, wherein said tumor is a mammary carcinoma.

12. The method of claim 11, wherein said tumor overexpresses heparin-binding EGF or amphiregulin.

13. The method of claim 5, wherein said tumor is a mammary carcinoma.

14. The method of claim 5, wherein said tumor overexpresses heparin-binding EGF or amphiregulin.

* * * * *

SEQUENCE LISTING

<160> NUMBER OF SEQ ID NOS: 36

<210> SEQ ID NO 1
<211> LENGTH: 968
<212> TYPE: PRT
<213> ORGANISM: Mus musculus

<400> SEQUENCE: 1

```
Met Gln Pro Lys Val Pro Leu Gly Ser Arg Lys Gln Lys Pro Cys Ser
1               5                   10                  15

Asp Met Gly Asp Val Gln Arg Ala Ala Arg Ser Arg Gly Ser Leu Ser
            20                  25                  30

Ala His Met Leu Leu Leu Leu Ala Ser Ile Thr Met Leu Leu Cys
        35                  40                  45

Ala Arg Gly Ala His Gly Arg Pro Thr Glu Glu Asp Glu Glu Leu Val
    50                  55                  60

Leu Pro Ser Leu Glu Arg Ala Pro Gly His Asp Ser Thr Thr Thr Arg
65                  70                  75                  80

Leu Arg Leu Asp Ala Phe Gly Gln Gln Leu His Leu Lys Leu Gln Pro
                85                  90                  95

Asp Ser Gly Phe Leu Ala Pro Gly Phe Thr Leu Gln Thr Val Gly Arg
            100                 105                 110

Ser Pro Gly Ser Glu Ala Gln His Leu Asp Pro Thr Gly Asp Leu Ala
        115                 120                 125

His Cys Phe Tyr Ser Gly Thr Val Asn Gly Asp Pro Gly Ser Ala Ala
    130                 135                 140

Ala Leu Ser Leu Cys Glu Gly Val Arg Gly Ala Phe Tyr Leu Gln Gly
145                 150                 155                 160

Glu Glu Phe Phe Ile Gln Pro Ala Pro Gly Val Ala Thr Glu Arg Leu
                165                 170                 175

Ala Pro Ala Val Pro Glu Glu Ser Ser Ala Arg Pro Gln Phe His
            180                 185                 190

Ile Leu Arg Arg Arg Arg Gly Ser Gly Ala Lys Cys Gly Val
        195                 200                 205

Met Asp Asp Glu Thr Leu Pro Thr Ser Asp Ser Arg Pro Glu Ser Gln
    210                 215                 220

Asn Thr Arg Asn Gln Trp Pro Val Arg Asp Pro Thr Pro Gln Asp Ala
225                 230                 235                 240

Gly Lys Pro Ser Gly Pro Gly Ser Ile Arg Lys Lys Arg Phe Val Ser
                245                 250                 255

Ser Pro Arg Tyr Val Glu Thr Met Leu Val Ala Asp Gln Ser Met Ala
            260                 265                 270

Asp Phe His Gly Ser Gly Leu Lys His Tyr Leu Leu Thr Leu Phe Ser
        275                 280                 285

Val Ala Ala Arg Phe Tyr Lys His Pro Ser Ile Arg Asn Ser Ile Ser
    290                 295                 300

Leu Val Val Val Lys Ile Leu Val Ile Tyr Glu Gln Lys Gly Pro
305                 310                 315                 320

Glu Val Thr Ser Asn Ala Ala Leu Thr Leu Arg Asn Phe Cys Asn Trp
                325                 330                 335

Gln Lys Gln His Asn Ser Pro Ser Asp Arg Asp Pro Glu His Tyr Asp
            340                 345                 350

Thr Ala Ile Leu Phe Thr Arg Gln Asp Leu Cys Gly Ser His Thr Cys
```

-continued

```
             355                 360                 365
Asp Thr Leu Gly Met Ala Asp Val Gly Thr Val Cys Asp Pro Ser Arg
    370                 375                 380
Ser Cys Ser Val Ile Glu Asp Asp Gly Leu Gln Ala Ala Phe Thr Thr
385                 390                 395                 400
Ala His Glu Leu Gly His Val Phe Asn Met Pro His Asp Asp Ala Lys
                405                 410                 415
His Cys Ala Ser Leu Asn Gly Val Thr Gly Asp Ser His Leu Met Ala
                420                 425                 430
Ser Met Leu Ser Ser Leu Asp His Ser Gln Pro Trp Ser Pro Cys Ser
        435                 440                 445
Ala Tyr Met Val Thr Ser Phe Leu Asp Asn Gly His Gly Glu Cys Leu
        450                 455                 460
Met Asp Lys Pro Gln Asn Pro Ile Lys Leu Pro Ser Asp Leu Pro Gly
465                 470                 475                 480
Thr Leu Tyr Asp Ala Asn Arg Gln Cys Gln Phe Thr Phe Gly Glu Glu
                485                 490                 495
Ser Lys His Cys Pro Asp Ala Ala Ser Thr Cys Thr Thr Leu Trp Cys
                500                 505                 510
Thr Gly Thr Ser Gly Gly Leu Leu Val Cys Gln Thr Lys His Phe Pro
        515                 520                 525
Trp Ala Asp Gly Thr Ser Cys Gly Glu Gly Lys Trp Cys Val Ser Gly
        530                 535                 540
Lys Cys Val Asn Lys Thr Asp Met Lys His Phe Ala Thr Pro Val His
545                 550                 555                 560
Gly Ser Trp Gly Pro Trp Gly Pro Trp Gly Asp Cys Ser Arg Thr Cys
                565                 570                 575
Gly Gly Gly Val Gln Tyr Thr Met Arg Glu Cys Asp Asn Pro Val Pro
                580                 585                 590
Lys Asn Gly Gly Lys Tyr Cys Glu Gly Lys Arg Val Arg Tyr Arg Ser
        595                 600                 605
Cys Asn Ile Glu Asp Cys Pro Asp Asn Asn Gly Lys Thr Phe Arg Glu
        610                 615                 620
Glu Gln Cys Glu Ala His Asn Glu Phe Ser Lys Ala Ser Phe Gly Asn
625                 630                 635                 640
Glu Pro Thr Val Glu Trp Thr Pro Lys Tyr Ala Gly Val Ser Pro Lys
                645                 650                 655
Asp Arg Cys Lys Leu Thr Cys Glu Ala Lys Gly Ile Gly Tyr Phe Phe
                660                 665                 670
Val Leu Gln Pro Lys Val Val Asp Gly Thr Pro Cys Ser Pro Asp Ser
        675                 680                 685
Thr Ser Val Cys Val Gln Gly Gln Cys Val Lys Ala Gly Cys Asp Arg
        690                 695                 700
Ile Ile Asp Ser Lys Lys Lys Phe Asp Lys Cys Gly Val Cys Gly Gly
705                 710                 715                 720
Asn Gly Ser Thr Cys Lys Lys Met Ser Gly Ile Val Thr Ser Thr Arg
                725                 730                 735
Pro Gly Tyr His Asp Ile Val Thr Ile Pro Ala Gly Ala Thr Asn Ile
                740                 745                 750
Glu Val Lys His Arg Asn Gln Arg Gly Ser Arg Asn Asn Gly Ser Phe
        755                 760                 765
Leu Ala Ile Arg Ala Ala Asp Gly Thr Tyr Ile Leu Asn Gly Asn Phe
        770                 775                 780
```

Thr Leu Ser Thr Leu Glu Gln Asp Leu Thr Tyr Lys Gly Thr Val Leu
785                 790                 795                 800

Arg Tyr Ser Gly Ser Ser Ala Ala Leu Glu Arg Ile Arg Ser Phe Ser
            805                 810                 815

Pro Leu Lys Glu Pro Leu Thr Ile Gln Val Leu Met Val Gly His Ala
            820                 825                 830

Leu Arg Pro Lys Ile Lys Phe Thr Tyr Phe Met Lys Lys Lys Thr Glu
            835                 840                 845

Ser Phe Asn Ala Ile Pro Thr Phe Ser Glu Trp Val Ile Glu Glu Trp
850                 855                 860

Gly Glu Cys Ser Lys Thr Cys Gly Ser Gly Trp Gln Arg Arg Val Val
865                 870                 875                 880

Gln Cys Arg Asp Ile Asn Gly His Pro Ala Ser Glu Cys Ala Lys Glu
            885                 890                 895

Val Lys Pro Ala Ser Thr Arg Pro Cys Ala Asp Leu Pro Cys Pro His
            900                 905                 910

Trp Gln Val Gly Asp Trp Ser Pro Cys Ser Lys Thr Cys Gly Lys Gly
            915                 920                 925

Tyr Lys Lys Arg Thr Leu Lys Cys Val Ser His Asp Gly Gly Val Leu
930                 935                 940

Ser Asn Glu Ser Cys Asp Pro Leu Lys Lys Pro Lys His Tyr Ile Asp
945                 950                 955                 960

Phe Cys Thr Leu Thr Gln Cys Ser
                965

<210> SEQ ID NO 2
<211> LENGTH: 2910
<212> TYPE: DNA
<213> ORGANISM: Mus musculus

<400> SEQUENCE: 2
gccatgcagc caaaagtccc tttggggtca cgcaagcaga agccctgctc cgacatgggg      60
gacgtccagc gggcagcgag atctcggggc tctctgtccg cacacatgct gttgctgctc     120
ctcgcttcca taacaatgct gctatgtgcg cggggcgcac acgggcgccc cacggaggaa     180
gatgaggagc tggtcctgcc ctcgctggag gcgccccggg ccacgattc accaccaca      240
cgccttcgtc tggacgcctt tggccagcag ctacatctga gttgcagcc ggacagcggt      300
ttcttggcgc tggcttcac cctgcagact gtggggcgca gtcccgggtc cgaggcacaa      360
catctggacc ccaccgggga cctggctcac tgcttctact ctggcacggt gaacggtgat      420
cccggctctg ccgcagccct cagcctctgt gaaggtgtgc gtggtgcctt ctacctacaa      480
ggagaggagt tcttcattca gccagcgcct ggagtggcca ccgagcgcct ggcccctgcc      540
gtgcccgagg aggagtcatc cgcacggccg cagttccaca tcctgaggcg aaggcggcgg      600
ggcagtggcg gcgccaagtg cggcgtcatg gacgacgaga ccctgccaac cagcgactcg      660
cgacccgaga gccagaacac ccggaaccag tggcctgtgc gggacccac gcctcaggac      720
gcgggaaagc catcaggacc aggaagcata aggaagaagc gatttgtgtc cagccccgt      780
tatgtggaaa ccatgctcgt ggctgaccag tccatggccg acttccacgg cagcggtcta      840
aagcattacc ttctaaccct gttctcggtg gcagccaggt tttacaagca tcccagcatt      900
aggaattcaa ttagcctggt ggtggtgaag atcttggtca tatatgagga gcagaaggga      960
ccagaagtta cctccaatgc agctctcacc cttcggaatt ctgcaactg gcagaaacaa     1020

-continued

```
cacaacagcc ccagtgaccg ggatccagag cactatgaca ctgcaattct gttcaccaga    1080
caggatttat gtggctccca cacgtgtgac actctcggga tggcagatgt tggaactgta    1140
tgtgacccca gcaggagctg ctcagtcata aagatgatg gtttgcaagc cgccttcacc    1200
acagcccacg aattgggcca tgtgtttaac atgccgcacg atgatgctaa gcactgtgcc    1260
agcttgaatg tgtgactgg cgattctcat ctgatggcct cgatgctctc cagcttagac    1320
catagccagc cctggtcacc ttgcagtgcc tacatggtca cgtccttcct agataatgga    1380 cacgggaat gtttgatgga caagccccag aatccaatca agctcccttc tgatcttccc    1440
ggtaccttgt acgatgccaa ccgccagtgt cagtttacat tcggagagga atccaagcac    1500
tgccctgatg cagccagcac atgtactacc ctgtggtgca ctggcaccct cggtggctta    1560
ctggtgtgcc aaacaaaaca cttcccttgg gcagatggca ccagctgtgg agaagggaag    1620
tggtgtgtca gtggcaagtg cgtgaacaag acagacatga agcattttgc tactcctgtt    1680
catggaagct ggggaccatg gggaccgtgg ggagactgct caagaacctg tggtggtgga    1740
gttcaataca caatgagaga atgtgacaac ccagtcccaa agaacggagg aagtactgt    1800 gaaggcaaac gagtccgcta caggtcctgt aacatcgagg actgtccaga caataacgga    1860
aaaacgttca gagaggagca gtgcgaggcg cacaatgagt tttccaaagc ttcctttggg    1920
aatgagccca ctgtagagtg gacacccaag tacgccggcg tctcgccaaa ggacaggtgc    1980
aagctcacct gtgaagccaa aggcattggc tactttttcg tcttacagcc caaggttgta    2040
gatggcactc cctgtagtcc agactctacc tctgtctgtg tgcaagggca gtgtgtgaaa    2100
gctggctgtg atcgcatcat agactccaaa aagaagtttg ataagtgtgg cgtttgtgga    2160
ggaaacggtt ccacatgcaa gaagatgtca ggaatagtca ctagtacaag acctgggtat    2220
catgacattg tcacaattcc tgctggagcc accaacattg aagtgaaaca tcggaatcaa    2280 aggggtcca gaaacaatgg cagctttctg gctattagag ccgctgatgg tacctatatt    2340
ctgaatggaa acttcactct gtccacacta gagcaagacc tcacctacaa aggtactgtc    2400
ttaaggtaca gtggttcctc ggctgcgctg gagagaatcc gcagctttag tccactcaaa    2460
gaacccttaa ccatccaggt tcttatggta ggccatgctc tccgacccaa aattaaattc    2520
acctacttta tgaagaagaa gacagagtca ttcaacgcca ttcccacatt ttctgagtgg    2580
gtgattgaag agtgggggga gtgctccaag acatgcggct caggttggca gagaagagta    2640
gtgcagtgca gagacattaa tggacaccct gcttccgaat gtgcaaagga agtgaagcca    2700
gccagtacca gaccttgtgc agaccttcct tgcccacact ggcaggtggg ggattggtca    2760
ccatgttcca aaacttgcgg gaagggttac aagaagagaa ccttgaaatg tgtgtcccac    2820
gatgggggcg tgttatcaaa tgagagctgt gatcctttga agaagccaaa gcattacatt    2880
gacttttgca cactgacaca gtgcagttaa                                    2910
```

<210> SEQ ID NO 3
<211> LENGTH: 967
<212> TYPE: PRT
<213> ORGANISM: Homo sapiens

<400> SEQUENCE: 3

Met Gln Arg Ala Val Pro Glu Gly Phe Gly Arg Lys Leu Gly Ser
1               5                   10                  15

Asp Met Gly Asn Ala Glu Arg Ala Pro Gly Ser Arg Ser Phe Gly Pro
                20                  25                  30

Val Pro Thr Leu Leu Leu Leu Ala Ala Ala Leu Leu Ala Val Ser Asp

-continued

```
                35                  40                  45
Ala Leu Gly Arg Pro Ser Glu Glu Asp Glu Leu Val Pro Glu
 50                  55                  60

Leu Glu Arg Ala Pro Gly His Gly Thr Thr Arg Leu Arg Leu His Ala
 65                  70                  75                  80

Phe Asp Gln Gln Leu Asp Leu Glu Leu Arg Pro Asp Ser Ser Phe Leu
                 85                  90                  95

Ala Pro Gly Phe Thr Leu Gln Asn Val Gly Arg Lys Ser Gly Ser Glu
                100                 105                 110

Thr Pro Leu Pro Glu Thr Asp Leu Ala His Cys Phe Tyr Ser Gly Thr
                115                 120                 125

Val Asn Gly Asp Pro Ser Ser Ala Ala Ala Leu Ser Leu Cys Glu Gly
130                 135                 140

Val Arg Gly Ala Phe Tyr Leu Leu Gly Glu Ala Tyr Phe Ile Gln Pro
145                 150                 155                 160

Leu Pro Ala Ala Ser Glu Arg Leu Ala Thr Ala Ala Pro Gly Glu Lys
                165                 170                 175

Pro Pro Ala Pro Leu Gln Phe His Leu Leu Arg Arg Asn Arg Gln Gly
                180                 185                 190

Asp Val Gly Gly Thr Cys Gly Val Val Asp Asp Glu Pro Arg Pro Thr
                195                 200                 205

Gly Lys Ala Glu Thr Glu Asp Glu Glu Gly Thr Glu Gly Glu Asp
                210                 215                 220

Glu Gly Ala Gln Trp Ser Pro Gln Asp Pro Ala Leu Gln Gly Val Gly
225                 230                 235                 240

Gln Pro Thr Gly Thr Gly Ser Ile Arg Lys Lys Arg Phe Val Ser Ser
                245                 250                 255

His Arg Tyr Val Glu Thr Met Leu Val Ala Asp Gln Ser Met Ala Glu
                260                 265                 270

Phe His Gly Ser Gly Leu Lys His Tyr Leu Leu Thr Leu Phe Ser Val
                275                 280                 285

Ala Ala Arg Leu Tyr Lys His Pro Ser Ile Arg Asn Ser Val Ser Leu
290                 295                 300

Val Val Val Lys Ile Leu Val Ile His Asp Glu Gln Lys Gly Pro Glu
305                 310                 315                 320

Val Thr Ser Asn Ala Ala Leu Thr Leu Arg Asn Phe Cys Asn Trp Gln
                325                 330                 335

Lys Gln His Asn Pro Pro Ser Asp Arg Asp Ala Glu His Tyr Asp Thr
                340                 345                 350

Ala Ile Leu Phe Thr Arg Gln Asp Leu Cys Gly Ser Gln Thr Cys Asp
                355                 360                 365

Thr Leu Gly Met Ala Asp Val Gly Thr Val Cys Asp Pro Ser Arg Ser
                370                 375                 380

Cys Ser Val Ile Glu Asp Asp Gly Leu Gln Ala Ala Phe Thr Thr Ala
385                 390                 395                 400

His Glu Leu Gly His Val Phe Asn Met Pro His Asp Asp Ala Lys Gln
                405                 410                 415

Cys Ala Ser Leu Asn Gly Val Asn Gln Asp Ser His Met Met Ala Ser
                420                 425                 430

Met Leu Ser Asn Leu Asp His Ser Gln Pro Trp Ser Pro Cys Ser Ala
                435                 440                 445

Tyr Met Ile Thr Ser Phe Leu Asp Asn Gly His Gly Glu Cys Leu Met
                450                 455                 460
```

-continued

```
Asp Lys Pro Gln Asn Pro Ile Gln Leu Pro Gly Asp Leu Pro Gly Thr
465                 470                 475                 480

Ser Tyr Asp Ala Asn Arg Gln Cys Gln Phe Thr Phe Gly Glu Asp Ser
                485                 490                 495

Lys His Cys Pro Asp Ala Ala Ser Thr Cys Ser Thr Leu Trp Cys Thr
                500                 505                 510

Gly Thr Ser Gly Gly Val Leu Val Cys Gln Thr Lys His Phe Pro Trp
            515                 520                 525

Ala Asp Gly Thr Ser Cys Gly Glu Gly Lys Trp Cys Ile Asn Gly Lys
530                 535                 540

Cys Val Asn Lys Thr Asp Arg Lys His Phe Asp Thr Pro Phe His Gly
545                 550                 555                 560

Ser Trp Gly Met Trp Gly Pro Trp Gly Asp Cys Ser Arg Thr Cys Gly
                565                 570                 575

Gly Gly Val Gln Tyr Thr Met Arg Glu Cys Asp Asn Pro Val Pro Lys
            580                 585                 590

Asn Gly Gly Lys Tyr Cys Glu Gly Lys Arg Val Arg Tyr Arg Ser Cys
                595                 600                 605

Asn Leu Glu Asp Cys Pro Asp Asn Asn Gly Lys Thr Phe Arg Glu Glu
            610                 615                 620

Gln Cys Glu Ala His Asn Glu Phe Ser Lys Ala Ser Phe Gly Ser Gly
625                 630                 635                 640

Pro Ala Val Glu Trp Ile Pro Lys Tyr Ala Gly Val Ser Pro Lys Asp
                645                 650                 655

Arg Cys Lys Leu Ile Cys Gln Ala Lys Gly Ile Gly Tyr Phe Phe Val
                660                 665                 670

Leu Gln Pro Lys Val Val Asp Gly Thr Pro Cys Ser Pro Asp Ser Thr
            675                 680                 685

Ser Val Cys Val Gln Gly Gln Cys Val Lys Ala Gly Cys Asp Arg Ile
690                 695                 700

Ile Asp Ser Lys Lys Lys Phe Asp Lys Cys Gly Val Cys Gly Gly Asn
705                 710                 715                 720

Gly Ser Thr Cys Lys Lys Ile Ser Gly Ser Val Thr Ser Ala Lys Pro
                725                 730                 735

Gly Tyr His Asp Ile Ile Thr Ile Pro Thr Gly Ala Thr Asn Ile Glu
            740                 745                 750

Val Lys Gln Arg Asn Gln Arg Gly Ser Arg Asn Asn Gly Ser Phe Leu
                755                 760                 765

Ala Ile Lys Ala Ala Asp Gly Thr Tyr Ile Leu Asn Gly Asp Tyr Thr
770                 775                 780

Leu Ser Thr Leu Glu Gln Asp Ile Met Tyr Lys Gly Val Val Leu Arg
785                 790                 795                 800

Tyr Ser Gly Ser Ser Ala Ala Leu Glu Arg Ile Arg Ser Phe Ser Pro
                805                 810                 815

Leu Lys Glu Pro Leu Thr Ile Gln Val Leu Thr Val Gly Asn Ala Leu
                820                 825                 830

Arg Pro Lys Ile Lys Tyr Thr Tyr Phe Val Lys Lys Lys Glu Ser
                835                 840                 845

Phe Asn Ala Ile Pro Thr Phe Ser Ala Trp Val Ile Glu Glu Trp Gly
                850                 855                 860

Glu Cys Ser Lys Ser Cys Glu Leu Gly Trp Gln Arg Arg Leu Val Glu
865                 870                 875                 880
```

```
Cys Arg Asp Ile Asn Gly Gln Pro Ala Ser Glu Cys Ala Lys Glu Val
                885                 890                 895

Lys Pro Ala Ser Thr Arg Pro Cys Ala Asp His Pro Cys Pro Gln Trp
            900                 905                 910

Gln Leu Gly Glu Trp Ser Ser Cys Ser Lys Thr Cys Gly Lys Gly Tyr
        915                 920                 925

Lys Lys Arg Ser Leu Lys Cys Leu Ser His Asp Gly Gly Val Leu Ser
    930                 935                 940

His Glu Ser Cys Asp Pro Leu Lys Lys Pro Lys His Phe Ile Asp Phe
945                 950                 955                 960

Cys Thr Met Ala Glu Cys Ser
                965

<210> SEQ ID NO 4
<211> LENGTH: 2907
<212> TYPE: DNA
<213> ORGANISM: Homo sapiens

<400> SEQUENCE: 4
```

| | | | | |
|---|---|---|---|---|
| gcaatgcagc | gagctgtgcc | cgaggggttc | ggaaggcgca | agctgggcag cgacatgggg | 60 |
| aacgcggagc | gggctccggg | gtctcggagc | tttgggcccg | tacccacgct gctgctgctc | 120 |
| gccgcggcgc | tactggccgt | gtcggacgca | ctcgggcgcc | cctccgagga ggacgaggag | 180 |
| ctagtggtgc | cggagctgga | gcgcgccccg | ggacacggga | ccacgcgcct ccgcctgcac | 240 |
| gcctttgacc | agcagctgga | tctggagctg | cggcccgaca | gcagcttttt ggcgcccggc | 300 |
| ttcacgctcc | agaacgtggg | gcgcaaatcc | gggtccgaga | cgccgcttcc ggaaaccgac | 360 |
| ctggcgcact | gcttctactc | cggcaccgtg | aatggcgatc | ccagctcggc tgccgccctc | 420 |
| agcctctgcg | agggcgtgcg | cggcgccttc | tacctgctgg | gggaggcgta tttcatccag | 480 |
| ccgctgcccg | ccgccagcga | gcgcctcgcc | accgccgccc | caggggagaa gccgccggca | 540 |
| ccactacagt | tccacctcct | gcggcggaat | cggcagggcg | acgtcggcgg cacgtgcggg | 600 |
| gtcgtggacg | acgagccccg | gccgactggg | aaagcggaga | ccgaagacga ggacgaaggg | 660 |
| actgagggcg | aggacgaagg | ggctcagtgg | tcgccgcagg | acccggcact gcaaggcgta | 720 |
| ggacagccca | caggaactgg | aagcataaga | aagaagcgat | ttgtgtccag tcaccgctat | 780 |
| gtggaaacca | tgcttgtggc | agaccagtcg | atggcagaat | tccacggcag tggtctaaag | 840 |
| cattaccttc | tcacgttgtt | ttcggtggca | gccagattgt | acaaacaccc cagcattcgt | 900 |
| aattcagtta | gcctggtggt | ggtgaagatc | ttggtcatcc | acgatgaaca gaaggggccg | 960 |
| gaagtgacct | ccaatgctgc | cctcactctg | cggaactttt | gcaactgcaa gaagcagcac | 1020 |
| aacccaccca | gtgaccggga | tgcagagcac | tatgacacag | caattctttt caccagacag | 1080 |
| gacttgtgtg | gtcccagac | atgtgatact | cttgggatgg | ctgatgttgg aactgtgtgt | 1140 |
| gatccgagca | gaagctgctc | cgtcatagaa | gatgatggtt | acaagctgc cttcaccaca | 1200 |
| gcccatgaat | taggccacgt | gtttaacatg | ccacatgatg | atgcaaagca gtgtgccagc | 1260 |
| cttaatggtg | tgaaccagga | ttcccacatg | atggcgtcaa | tgctttccaa cctgaccac | 1320 |
| agccagcctt | ggtctccttg | cagtgcctac | atgattacat | catttctgga taatggtcat | 1380 |
| ggggaatgtt | tgatggacaa | gcctcagaat | cccatacagc | tcccaggcga tctccctggc | 1440 |
| acctcgtacg | atgccaaccg | gcagtgccag | tttacatttg | gggaggactc caaacactgc | 1500 |
| cccgatgcag | ccagcacatg | tagcaccttg | tggtgtaccg | gcacctctgg tggggtgctg | 1560 |
| gtgtgtcaaa | ccaaacactt | cccgtgggcg | gatggcacca | gctgtggaga agggaaatgg | 1620 |

-continued

```
tgtatcaacg gcaagtgtgt gaacaaaacc gacagaaagc attttgatac gccttttcat      1680
ggaagctggg gaatgtgggg gccttgggga gactgttcga gaacgtgcgg tggaggagtc      1740
cagtacacga tgagggaatg tgacaaccca gtcccaaaga atggagggaa gtactgtgaa      1800
ggcaaacgag tgcgctacag atcctgtaac cttgaggact gtccagacaa taatggaaaa      1860
acctttagag aggaacaatg tgaagcacac aacgagtttt caaaagcttc ctttgggagt      1920
gggcctgcgg tggaatggat tcccaagtac gctggcgtct caccaaagga caggtgcaag      1980
ctcatctgcc aagccaaagg cattggctac ttcttcgttt tgcagcccaa ggttgtagat      2040
ggtactccat gtagcccaga ttccacctct gtctgtgtgc aaggacagtg tgtaaaagct      2100
ggttgtgatc gcatcataga ctccaaaaag aagtttgata atgtggtgt ttgcggggga      2160 aatggatcta cttgtaaaaa aatatcagga tcagttacta gtgcaaaacc tggatatcat      2220
gatatcatca caattccaac tggagccacc aacatcgaag tgaaacagcg aaccagagg       2280 ggatccagga acaatggcag ctttcttgcc atcaaagctg ctgatggcac atatattctt      2340
aatggtgact acactttgtc caccttagag caagacatta tgtacaaagg tgttgtcttg      2400
aggtacagcg gctcctctgc ggcattggaa agaattcgca gctttagccc tctcaaagag      2460
cccttgacca tccaggttct tactgtgggc aatgccttc gacctaaaat taaatacacc       2520
tacttcgtaa agaagaagaa ggaatctttc aatgctatcc cactttttc agcatgggtc       2580 attgaagagt ggggcgaatg ttctaagtca tgtgaattgg gttggcagag aagactggta      2640
gaatgccgag acattaatgg acagcctgct tccgagtgtg caaggaagt gaagccagcc       2700 agcaccagac cttgtgcaga ccatccctgc ccccagtggc agctggggga gtggtcatca      2760
tgttctaaga cctgtgggaa gggttacaaa aaaagaagct gaagtgtct gtcccatgat       2820 ggaggggtgt tatctcatga gagctgtgat ccttaaaaga aacctaaaca tttcatagac      2880
ttttgcacaa tggcagaatg cagttaa                                          2907
```

<210> SEQ ID NO 5
<211> LENGTH: 166
<212> TYPE: PRT
<213> ORGANISM: Mus musculus

<400> SEQUENCE: 5

```
Met Gly Asp Val Gln Arg Ala Ala Arg Ser Arg Gly Ser Leu Ser Ala
1               5                   10                  15

His Met Leu Leu Leu Leu Ala Ser Ile Thr Met Leu Leu Cys Ala
            20                  25                  30

Arg Gly Ala His Gly Arg Pro Thr Glu Lys Lys Lys Thr Glu Ser Phe
        35                  40                  45

Asn Ala Ile Pro Thr Phe Ser Glu Trp Val Ile Glu Glu Trp Gly Glu
    50                  55                  60

Cys Ser Lys Thr Cys Gly Ser Gly Trp Gln Arg Arg Val Val Gln Cys
65                  70                  75                  80

Arg Asp Ile Asn Gly His Pro Ala Ser Glu Cys Ala Lys Glu Val Lys
                85                  90                  95

Pro Ala Ser Thr Arg Pro Cys Ala Asp Leu Pro Cys Pro His Trp Gln
            100                 105                 110

Val Gly Asp Trp Ser Pro Cys Ser Lys Thr Cys Gly Lys Gly Tyr Lys
        115                 120                 125

Lys Arg Thr Leu Lys Cys Val Ser His Asp Gly Gly Val Leu Ser Asn
    130                 135                 140
```

-continued

Glu Ser Cys Asp Pro Leu Lys Lys Pro Lys His Tyr Ile Asp Phe Cys
145                 150                 155                 160

Thr Leu Thr Gln Cys Ser
            165

<210> SEQ ID NO 6
<211> LENGTH: 504
<212> TYPE: DNA
<213> ORGANISM: Mus musculus

<400> SEQUENCE: 6
gacatggggg acgtccagcg ggcagcgaga tctcggggct ctctgtccgc acacatgctg     60
ttgctgctcc tcgcttccat aacaatgctg ctatgtgcgc ggggcgcaca cgggcgcccc    120
acggagaaga agaagacaga gtcattcaac gccattccca cattttctga gtgggtgatt    180
gaagagtggg gggagtgctc caagacatgc ggctcaggtt ggcagagaag agtagtgcag    240
tgcagagaca ttaatggaca ccctgcttcc gaatgtgcaa aggaagtgaa gccagccagt    300
accagacctt gtgcagacct tccttgccca cactggcagg tggggattg gtcaccatgt     360 tccaaaactt gcgggaaggg ttacaagaag agaaccttga atgtgtgtc ccacgatggg     420 ggcgtgttat caaatgagag ctgtgatcct ttgaagaagc caaagcatta cattgacttt    480
tgcacactga cacagtgcag ttaa                                           504

<210> SEQ ID NO 7
<211> LENGTH: 179
<212> TYPE: PRT
<213> ORGANISM: Homo sapiens

<400> SEQUENCE: 7

Met Gln Arg Ala Val Pro Glu Gly Phe Gly Arg Arg Lys Leu Gly Ser
1               5                   10                  15

Asp Met Gly Asn Ala Glu Arg Ala Pro Gly Ser Arg Ser Phe Gly Pro
            20                  25                  30

Val Pro Thr Leu Leu Leu Ala Ala Ala Leu Leu Ala Val Ser Asp Ala
        35                  40                  45

Ala Leu Gly Arg Pro Ser Glu Lys Lys Glu Ser Phe Asn Ala Ile Pro
    50                  55                  60

Thr Phe Ser Ala Trp Val Ile Glu Glu Trp Gly Glu Cys Ser Lys Ser
65                  70                  75                  80

Cys Glu Leu Gly Trp Gln Arg Arg Leu Val Glu Cys Arg Asp Ile Asn
                85                  90                  95

Gly Gln Pro Ala Ser Glu Cys Ala Lys Glu Val Lys Pro Ala Ser Thr
            100                 105                 110

Arg Pro Cys Ala Asp His Pro Cys Pro Gln Trp Gln Leu Gly Glu Trp
        115                 120                 125

Ser Ser Cys Ser Lys Thr Cys Gly Lys Gly Tyr Lys Lys Arg Ser Leu
    130                 135                 140

Lys Cys Leu Ser His Asp Gly Gly Val Leu Ser His Glu Ser Cys Asp
145                 150                 155                 160

Pro Leu Lys Lys Pro Lys His Phe Ile Asp Phe Cys Thr Met Ala Glu
                165                 170                 175

Cys Ser

<210> SEQ ID NO 8
<211> LENGTH: 543

<212> TYPE: DNA
<213> ORGANISM: Homo sapiens

<400> SEQUENCE: 8

```
gcaatgcagc gagctgtgcc cgaggggttc ggaaggcgca agctgggcag cgacatgggg      60
aacgcggagc gggctccggg gtctcggagc tttgggcccg tacccacgct gctgctgctc     120
gccgcggcgc tactggccgt gtcggacgca ctcgggcgcc cctccgagaa gaagaaggaa     180
tctttcaatg ctatccccac ttttcagca tgggtcattg aagagtgggg cgaatgttct     240
aagtcatgtg aattgggttg cagagaaga ctggtagaat gccgagacat taatggacag     300
cctgcttccg agtgtgcaaa ggaagtgaag ccagccagca ccagaccttg tgcagaccat     360
ccctgccccc agtggcagct gggggagtgg tcatcatgtt ctaagacctg tgggaagggt     420
tacaaaaaaa gaagcttgaa gtgtctgtcc catgatggag gggtgttatc tcatgagagc     480
tgtgatcctt taagaaaacc taaacatttc atagactttt gcacaatggc agaatgcagt     540
taa                                                                  543
```

<210> SEQ ID NO 9
<211> LENGTH: 596
<212> TYPE: PRT
<213> ORGANISM: Mus musculus

<400> SEQUENCE: 9

```
Met Gly Asp Val Gln Arg Ala Ala Arg Ser Arg Gly Ser Leu Ser Ala
1               5                   10                  15

His Met Leu Leu Leu Leu Ala Ser Ile Thr Met Leu Leu Cys Ala
                20                  25                  30

Arg Gly Ala His Gly Arg Pro Thr Glu Glu Asp Glu Glu Leu Val Leu
            35                  40                  45

Pro Ser Leu Glu Arg Ala Pro Gly His Asp Ser Thr Thr Thr Arg Leu
        50                  55                  60

Arg Leu Asp Ala Phe Gly Gln Gln Leu His Leu Lys Leu Gln Pro Asp
65                  70                  75                  80

Ser Gly Phe Leu Ala Pro Gly Phe Thr Leu Gln Thr Val Gly Arg Ser
                85                  90                  95

Pro Gly Ser Glu Ala Gln His Leu Asp Pro Thr Gly Asp Leu Ala His
            100                 105                 110

Cys Phe Tyr Ser Gly Thr Val Asn Gly Asp Pro Gly Ser Ala Ala Ala
        115                 120                 125

Leu Ser Leu Cys Glu Gly Val Arg Gly Ala Phe Tyr Leu Gln Gly Glu
    130                 135                 140

Glu Phe Phe Ile Gln Pro Ala Pro Gly Val Ala Thr Glu Arg Leu Ala
145                 150                 155                 160

Pro Ala Val Pro Glu Glu Glu Ser Ser Ala Arg Pro Gln Phe His Ile
                165                 170                 175

Leu Arg Arg Arg Arg Arg Gly Ser Gly Gly Ala Lys Cys Gly Val Met
            180                 185                 190

Asp Asp Glu Thr Leu Pro Thr Ser Asp Ser Arg Pro Glu Ser Gln Asn
        195                 200                 205

Thr Arg Asn Gln Trp Pro Val Arg Asp Pro Thr Pro Gln Asp Ala Gly
    210                 215                 220

Lys Pro Ser Gly Pro Gly Ser Ile Arg Lys Lys Arg Phe Val Ser Ser
225                 230                 235                 240

Pro Arg Tyr Val Glu Thr Met Leu Val Ala Asp Gln Ser Met Ala Asp
```

-continued

```
                245                 250                 255
Phe His Gly Ser Gly Leu Lys His Tyr Leu Leu Thr Leu Phe Ser Val
            260                 265                 270
Ala Ala Arg Phe Tyr Lys His Pro Ser Ile Arg Asn Ser Ile Ser Leu
            275                 280                 285
Val Val Val Lys Ile Leu Val Ile Tyr Glu Glu Gln Lys Gly Pro Glu
            290                 295                 300
Val Thr Ser Asn Ala Ala Leu Thr Leu Arg Asn Phe Cys Asn Trp Gln
305                 310                 315                 320
Lys Gln His Asn Ser Pro Ser Asp Arg Asp Pro Glu His Tyr Asp Thr
            325                 330                 335
Ala Ile Leu Phe Thr Arg Gln Asp Leu Cys Gly Ser His Thr Cys Asp
            340                 345                 350
Thr Leu Gly Met Ala Asp Val Gly Thr Val Cys Asp Pro Ser Arg Ser
            355                 360                 365
Cys Ser Val Ile Glu Asp Asp Gly Leu Gln Ala Ala Phe Thr Thr Ala
            370                 375                 380
His Glu Leu Gly His Val Phe Asn Met Pro His Asp Asp Ala Lys His
385                 390                 395                 400
Cys Ala Ser Leu Asn Gly Val Thr Gly Asp Ser His Leu Met Ala Ser
            405                 410                 415
Met Leu Ser Ser Leu Asp His Ser Gln Pro Trp Ser Pro Cys Ser Ala
            420                 425                 430
Tyr Met Val Thr Ser Phe Leu Asp Asn Gly His Gly Glu Cys Leu Met
            435                 440                 445
Asp Lys Pro Gln Asn Pro Ile Lys Leu Pro Ser Asp Leu Pro Gly Thr
450                 455                 460
Leu Tyr Asp Ala Asn Arg Gln Cys Gln Phe Thr Phe Gly Glu Glu Ser
465                 470                 475                 480
Lys His Cys Pro Asp Ala Ala Ser Thr Cys Thr Thr Leu Trp Cys Thr
                485                 490                 495
Gly Thr Ser Gly Gly Leu Leu Val Cys Gln Thr Lys His Phe Pro Trp
            500                 505                 510
Ala Asp Gly Thr Ser Cys Gly Glu Gly Lys Trp Cys Val Ser Gly Lys
            515                 520                 525
Cys Val Asn Lys Thr Asp Met Lys His Phe Ala Thr Pro Val His Gly
            530                 535                 540
Ser Trp Gly Pro Trp Gly Pro Trp Gly Asp Cys Ser Arg Thr Cys Gly
545                 550                 555                 560
Gly Gly Val Gln Tyr Thr Met Arg Glu Cys Asp Asn Pro Val Pro Lys
            565                 570                 575
Asn Gly Gly Lys Tyr Cys Glu Gly Lys Arg Val Arg Tyr Arg Ser Cys
            580                 585                 590
Asn Ile Glu Asp
        595
```

<210> SEQ ID NO 10
<211> LENGTH: 1794
<212> TYPE: DNA
<213> ORGANISM: Mus musculus

<400> SEQUENCE: 10

```
gacatggggg acgtccagcg ggcagcgaga tctcggggct ctctgtccgc acacatgctg      60
ttgctgctcc tcgcttccat aacaatgctg ctatgtgcgc ggggcgcaca cgggcgcccc     120
```

-continued

```
acggaggaag atgaggagct ggtcctgccc tcgctggagc gcgccccggg ccacgattcc      180
accaccacac gccttcgtct ggacgccttt ggccagcagc tacatctgaa gttgcagccg      240
gacagcggtt tcttggcgcc tggcttcacc ctgcagactg tggggcgcag tcccgggtcc      300
gaggcacaac atctggaccc caccggggac ctggctcact gcttctactc tggcacggtg      360
aacggtgatc ccggctctgc cgcagccctc agcctctgtg aaggtgtgcg tggtgccttc      420
tacctacaag gagaggagtt cttcattcag ccagcgcctg gagtggccac cgagcgcctg      480
gcccctgccg tgcccgagga ggagtcatcc gcacggccgc agttccacat cctgaggcga      540
aggcggcggg gcagtggcgg cgccaagtgc ggcgtcatgg acgacgagac cctgccaacc      600
agcgactcgc gacccgagag ccagaacacc cggaaccagt ggcctgtgcg ggaccccacg      660
cctcaggacg cgggaaagcc atcaggacca ggaagcataa ggaagaagcg atttgtgtcc      720 agccccgtt atgtggaaac catgctcgtg gctgaccagt ccatggccga cttccacggc      780
agcggtctaa agcattacct tctaaccctg ttctcggtgg cagccaggtt ttacaagcat      840
cccagcatta ggaattcaat agcctggtg gtggtgaaga tcttggtcat atatgaggag      900
cagaagggac agaagttac ctccaatgca gctctcaccc ttcggaattt ctgcaactgg      960
cagaaacaac acaacagccc cagtgaccgg atccagagc actatgacac tgcaattctg     1020
ttcaccagac aggatttatg tggctcccac acgtgtgaca ctctcgggat ggcagatgtt     1080
ggaactgtat gtgaccccag caggagctgc tcagtcatag aagatgatgg tttgcaagcc     1140
gccttcacca cagcccacga attgggccat gtgtttaaca tgccgcacga tgatgctaag     1200
cactgtgcca gcttgaatgg tgtgactggc gattctcatc tgatggcctc gatgctctcc     1260
agcttagacc atagccagcc ctggtcacct tgcagtgcct acatggtcac gtccttccta     1320
gataatggac acggggaatg tttgatggac aagccccaga tccaatcaa gctcccttct     1380 gatcttcccg gtaccttgta cgatgccaac cgccagtgtc agtttacatt cggagaggaa     1440
tccaagcact gccctgatgc agccagcaca tgtactaccc tgtggtgcac tggcacctcc     1500
ggtggcttac tggtgtgcca aacaaaaac ttcccttggg cagatggcac cagctgtgga     1560
gaagggaagt ggtgtgtcag tggcaagtgc gtgaacaaga cagacatgaa gcattttgct     1620
actcctgttc atgaagctg gggaccatgg gaccgtggg gagactgctc aagaacctgt     1680
ggtggtggag ttcaatacac aatgagagaa tgtgacaacc cagtcccaaa gaacggaggg     1740
aagtactgtg aaggcaaacg agtccgctac aggtcctgta acatcgagga ctaa          1794
```

<210> SEQ ID NO 11
<211> LENGTH: 595
<212> TYPE: PRT
<213> ORGANISM: Homo sapiens

<400> SEQUENCE: 11

```
Met Gly Asn Ala Glu Arg Ala Pro Gly Ser Arg Ser Phe Gly Pro Val
1               5                   10                  15

Pro Thr Leu Leu Leu Leu Ala Ala Ala Leu Leu Ala Val Ser Asp Ala
            20                  25                  30

Leu Gly Arg Pro Ser Glu Glu Asp Glu Glu Leu Val Val Pro Glu Leu
        35                  40                  45

Glu Arg Ala Pro Gly His Gly Thr Thr Arg Leu Arg Leu His Ala Phe
    50                  55                  60

Asp Gln Gln Leu Asp Leu Glu Leu Arg Pro Asp Ser Ser Phe Leu Ala
65                  70                  75                  80
```

-continued

```
Pro Gly Phe Thr Leu Gln Asn Val Gly Arg Lys Ser Gly Ser Glu Thr
                85                  90                  95
Pro Leu Pro Glu Thr Asp Leu Ala His Cys Phe Tyr Ser Gly Thr Val
            100                 105                 110
Asn Gly Asp Pro Ser Ser Ala Ala Leu Ser Leu Cys Glu Gly Val
        115                 120                 125
Arg Gly Ala Phe Tyr Leu Leu Gly Glu Ala Tyr Phe Ile Gln Pro Leu
    130                 135                 140
Pro Ala Ala Ser Glu Arg Leu Ala Thr Ala Ala Pro Gly Glu Lys Pro
145                 150                 155                 160
Pro Ala Pro Leu Gln Phe His Leu Leu Arg Arg Asn Arg Gln Gly Asp
                165                 170                 175
Val Gly Gly Thr Cys Gly Val Val Asp Glu Pro Arg Pro Thr Gly
            180                 185                 190
Lys Ala Glu Thr Glu Asp Glu Asp Gly Thr Glu Gly Glu Asp Glu
        195                 200                 205
Gly Ala Gln Trp Ser Pro Gln Asp Pro Ala Leu Gln Gly Val Gly Gln
    210                 215                 220
Pro Thr Gly Thr Gly Ser Ile Arg Lys Lys Arg Phe Val Ser Ser His
225                 230                 235                 240
Arg Tyr Val Glu Thr Met Leu Val Ala Asp Gln Ser Met Ala Glu Phe
                245                 250                 255
His Gly Ser Gly Leu Lys His Tyr Leu Leu Thr Leu Phe Ser Val Ala
            260                 265                 270
Ala Arg Leu Tyr Lys His Pro Ser Ile Arg Asn Ser Val Ser Leu Val
        275                 280                 285
Val Val Lys Ile Leu Val Ile His Asp Glu Gln Lys Gly Pro Glu Val
    290                 295                 300
Thr Ser Asn Ala Ala Leu Thr Leu Arg Asn Phe Cys Asn Trp Gln Lys
305                 310                 315                 320
Gln His Asn Pro Pro Ser Asp Arg Asp Ala Glu His Tyr Asp Thr Ala
                325                 330                 335
Ile Leu Phe Thr Arg Gln Asp Leu Cys Gly Ser Gln Thr Cys Asp Thr
            340                 345                 350
Leu Gly Met Ala Asp Val Gly Thr Val Cys Asp Pro Ser Arg Ser Cys
        355                 360                 365
Ser Val Ile Glu Asp Asp Gly Leu Gln Ala Ala Phe Thr Thr Ala His
    370                 375                 380
Glu Leu Gly His Val Phe Asn Met Pro His Asp Asp Ala Lys Gln Cys
385                 390                 395                 400
Ala Ser Leu Asn Gly Val Asn Gln Asp Ser His Met Met Ala Ser Met
                405                 410                 415
Leu Ser Asn Leu Asp His Ser Gln Pro Trp Ser Pro Cys Ser Ala Tyr
            420                 425                 430
Met Ile Thr Ser Phe Leu Asp Asn Gly His Gly Glu Cys Leu Met Asp
        435                 440                 445
Lys Pro Gln Asn Pro Ile Gln Leu Pro Gly Asp Leu Pro Gly Thr Ser
    450                 455                 460
Tyr Asp Ala Asn Arg Gln Cys Gln Phe Thr Phe Gly Glu Asp Ser Lys
465                 470                 475                 480
His Cys Pro Asp Ala Ala Ser Thr Cys Ser Thr Leu Trp Cys Thr Gly
                485                 490                 495
```

```
Thr Ser Gly Gly Val Leu Val Cys Gln Thr Lys His Phe Pro Trp Ala
        500                 505                 510
Asp Gly Thr Ser Cys Gly Glu Gly Lys Trp Cys Ile Asn Gly Lys Cys
        515                 520                 525
Val Asn Lys Thr Asp Arg Lys His Phe Asp Thr Pro Phe His Gly Ser
        530                 535                 540
Trp Gly Met Trp Gly Pro Trp Gly Asp Cys Ser Arg Thr Cys Gly Gly
545                 550                 555                 560
Gly Val Gln Tyr Thr Met Arg Glu Cys Asp Asn Pro Val Pro Lys Asn
                565                 570                 575
Gly Gly Lys Tyr Cys Glu Gly Lys Arg Val Arg Tyr Arg Ser Cys Asn
                580                 585                 590
Leu Glu Asp
        595

<210> SEQ ID NO 12
<211> LENGTH: 1842
<212> TYPE: DNA
<213> ORGANISM: Homo sapiens

<400> SEQUENCE: 12
```

| | | | | |
|---|---|---|---|---|
| gcaatgcagc gagctgtgcc cgaggggttc ggaaggcgca agctgggcag cgacatgggg | 60 |
| aacgcggagc gggctccggg gtctcggagc tttgggcccg tacccacgct gctgctgctc | 120 |
| gccgcggcgc tactggccgt gtcggacgca ctcgggcgcc cctccgagga ggacgaggag | 180 |
| ctagtggtgc cggagctgga gcgcgccccg ggacacggga ccacgcgcct ccgcctgcac | 240 |
| gcctttgacc agcagctgga tctggagctg cggcccgaca gcagcttttt ggcgcccggc | 300 |
| ttcacgctcc agaacgtggg gcgcaaatcc gggtccgaga cgccgcttcc ggaaaccgac | 360 |
| ctggcgcact gcttctactc cggcaccgtg aatggcgatc ccagctcggc tgccgccctc | 420 |
| agcctctgcg agggcgtgcg cggcgccttc tacctgctgg gggaggcgta tttcatccag | 480 |
| ccgctgcccg ccgccagcga gcgcctcgcc accgccgccc aggggagaa gccgccggca | 540 |
| ccactacagt tccacctcct gcggcggaat cggcagggcg acgtcggcgg cacgtgcggg | 600 |
| gtcgtggacg acgagccccg gccgactggg aaagcggaga ccgaagacga ggacgaaggg | 660 |
| actgagggcg aggacgaagg ggctcagtgg tcgccgcagg acccggcact gcaaggcgta | 720 |
| ggacagccca caggaactgg aagcataaga aagaagcgat tgtgtccag tcaccgctat | 780 |
| gtggaaacca tgcttgtggc agaccagtcg atggcagaat tccacggcag tggtctaaag | 840 |
| cattaccttc tcacgttgtt ttcggtggca gccagattgt acaaacaccc cagcattcgt | 900 |
| aattcagtta gcctggtggt ggtgaagatc ttggtcatcc acgatgaaca gaaggggccg | 960 |
| gaagtgacct ccaatgctgc cctcactctg cggaactttt gcaactggca gaagcagcac | 1020 |
| aacccaccca gtgaccggga tgcagagcac tatgacacag caattcttt caccagacag | 1080 |
| gacttgtgtg ggtcccagac atgtgatact cttgggatgg ctgatgttgg aactgtgtgt | 1140 |
| gatccgagca gaagctgctc cgtcatagaa gatgatggtt acaagctgc cttcaccaca | 1200 |
| gcccatgaat taggccacgt gtttaacatg ccacatgatg atgcaaagca gtgtgccagc | 1260 |
| cttaatggtg tgaaccagga ttcccacatg atggcgtcaa tgctttccaa cctgaccac | 1320 |
| agccagcctt ggtctccttg cagtgcctac atgattcat catttctgga taatggtcat | 1380 |
| ggggaatgtt tgatggacaa gcctcagaat cccatacagc tcccaggcga tctccctggc | 1440 |
| acctcgtacg atgccaaccg gcagtgccag tttacatttg gggaggactc caaacactgc | 1500 |

```
cccgatgcag ccagcacatg tagcaccttg tggtgtaccg gcacctctgg tggggtgctg    1560
gtgtgtcaaa ccaaacactt cccgtgggcg gatggcacca gctgtggaga agggaaatgg    1620
tgtatcaacg gcaagtgtgt gaacaaaacc gacagaaagc attttgatac gccttttcat    1680
ggaagctggg gaatgtgggg ccttgggga gactgttcga gaacgtgcgg tggaggagtc    1740
cagtacacga tgagggaatg tgacaaccca gtcccaaaga atggagggaa gtactgtgaa    1800
ggcaaacgag tgcgctacag atcctgtaac cttgaggact aa                      1842
```

```
<210> SEQ ID NO 13
<211> LENGTH: 545
<212> TYPE: PRT
<213> ORGANISM: Mus musculus

<400> SEQUENCE: 13
```

```
Met Gly Asp Val Gln Arg Ala Ala Arg Ser Arg Gly Ser Leu Ser Ala
1               5                   10                  15

His Met Leu Leu Leu Leu Ala Ser Ile Thr Met Leu Leu Cys Ala
            20                  25                  30

Arg Gly Ala His Gly Arg Pro Thr Glu Glu Asp Glu Glu Leu Val Leu
        35                  40                  45

Pro Ser Leu Glu Arg Ala Pro Gly His Asp Ser Thr Thr Thr Arg Leu
    50                  55                  60

Arg Leu Asp Ala Phe Gly Gln Gln Leu His Leu Lys Leu Gln Pro Asp
65                  70                  75                  80

Ser Gly Phe Leu Ala Pro Gly Phe Thr Leu Gln Thr Val Gly Arg Ser
                85                  90                  95

Pro Gly Ser Glu Ala Gln His Leu Asp Pro Thr Gly Asp Leu Ala His
            100                 105                 110

Cys Phe Tyr Ser Gly Thr Val Asn Gly Asp Pro Gly Ser Ala Ala Ala
        115                 120                 125

Leu Ser Leu Cys Glu Gly Val Arg Gly Ala Phe Tyr Leu Gln Gly Glu
    130                 135                 140

Glu Phe Phe Ile Gln Pro Ala Pro Gly Val Ala Thr Glu Arg Leu Ala
145                 150                 155                 160

Pro Ala Val Pro Glu Glu Ser Ser Ala Arg Pro Gln Phe His Ile
                165                 170                 175

Leu Arg Arg Arg Arg Arg Gly Ser Gly Gly Ala Lys Cys Gly Val Met
            180                 185                 190

Asp Asp Glu Thr Leu Pro Thr Ser Asp Ser Arg Pro Ser Gln Asn
        195                 200                 205

Thr Arg Asn Gln Trp Pro Val Arg Asp Pro Thr Pro Gln Asp Ala Gly
    210                 215                 220

Lys Pro Ser Gly Pro Gly Ser Ile Arg Lys Lys Arg Phe Val Ser Ser
225                 230                 235                 240

Pro Arg Tyr Val Glu Thr Met Leu Val Ala Asp Gln Ser Met Ala Asp
                245                 250                 255

Phe His Gly Ser Gly Leu Lys His Tyr Leu Leu Thr Leu Phe Ser Val
            260                 265                 270

Ala Ala Arg Phe Tyr Lys His Pro Ser Ile Arg Asn Ser Ile Ser Leu
        275                 280                 285

Val Val Val Lys Ile Leu Val Ile Tyr Glu Glu Gln Lys Gly Pro Glu
    290                 295                 300

Val Thr Ser Asn Ala Ala Leu Thr Leu Arg Asn Phe Cys Asn Trp Gln
305                 310                 315                 320
```

-continued

```
Lys Gln His Asn Ser Pro Ser Asp Arg Asp Pro Glu His Tyr Asp Thr
                325                 330                 335

Ala Ile Leu Phe Thr Arg Gln Asp Leu Cys Gly Ser His Thr Cys Asp
            340                 345                 350

Thr Leu Gly Met Ala Asp Val Gly Thr Val Cys Asp Pro Ser Arg Ser
        355                 360                 365

Cys Ser Val Ile Glu Asp Gly Leu Gln Ala Phe Thr Thr Ala
    370                 375                 380

His Glu Leu Gly His Val Phe Asn Met Pro His Asp Ala Lys His
385                 390                 395                 400

Cys Ala Ser Leu Asn Gly Val Thr Gly Asp Ser His Leu Met Ala Ser
                405                 410                 415

Met Leu Ser Ser Leu Asp His Ser Gln Pro Trp Ser Pro Cys Ser Ala
            420                 425                 430

Tyr Met Val Thr Ser Phe Leu Asp Asn Gly His Gly Glu Cys Leu Met
        435                 440                 445

Asp Lys Pro Gln Asn Pro Ile Lys Leu Pro Ser Asp Leu Pro Gly Thr
    450                 455                 460

Leu Tyr Asp Ala Asn Arg Gln Cys Gln Phe Thr Phe Gly Glu Glu Ser
465                 470                 475                 480

Lys His Cys Pro Asp Ala Ala Ser Thr Cys Thr Thr Leu Trp Cys Thr
                485                 490                 495

Gly Thr Ser Gly Gly Leu Leu Val Cys Gln Thr Lys His Phe Pro Trp
            500                 505                 510

Ala Asp Gly Thr Ser Cys Gly Glu Gly Lys Trp Cys Val Ser Gly Lys
        515                 520                 525

Cys Val Asn Lys Thr Asp Met Lys His Phe Ala Thr Pro Val His Gly
    530                 535                 540

Ser
545

<210> SEQ ID NO 14
<211> LENGTH: 1641
<212> TYPE: DNA
<213> ORGANISM: Mus musculus

<400> SEQUENCE: 14
gacatggggg acgtccagcg ggcagcgaga tctcggggct ctctgtccgc acacatgctg      60
ttgctgctcc tcgcttccat aacaatgctg ctatgtgcgc ggggcgcaca cgggcgcccc    120
acggaggaag atgaggagct ggtcctgccc tcgctggagc gcgccccggg ccacgattcc    180
accaccacac gccttcgtct ggacgccttt ggccagcagc tacatctgaa gttgcagccg    240 acagcggtt tcttggcgcc tggcttcacc ctgcagactg tggggcgcag tcccgggtcc    300
gaggcacaac atctggaccc caccggggac ctggctcact gcttctactc tggcacggtg    360
aacggtgatc ccggctctgc cgcagcccts agcctctgtg aaggtgtgcg tggtgccttc    420
tacctacaag agaggagtt cttcattcag ccagcgcctg gagtggccac cgagcgcctg    480
gcccctgccg tgcccgagga ggagtcatcc gcacggccgc agttccacat cctgaggcga    540
aggcggcggg gcagtggcgg cgccaagtgc ggcgtcatgg acgacgagac cctgccaacc    600
agcgactcgc gacccgagag ccagaacacc cggaaccagt ggcctgtgcg gaccccacg    660 cctcaggacg cggaaagcc atcaggacca ggaagcataa ggaagaagcg atttgtgtcc    720
agcccccgtt atgtggaaac catgctcgtg gctgaccagt ccatggccga cttccacggc    780
```

-continued

```
agcggtctaa agcattacct tctaaccctg ttctcggtgg cagccaggtt ttacaagcat      840
cccagcatta ggaattcaat tagcctggtg gtggtgaaga tcttggtcat atatgaggag      900
cagaagggac agaagttac ctccaatgca gctctcaccc ttcggaattt ctgcaactgg       960
cagaaacaac acaacagccc cagtgaccgg atccagagc actatgacac tgcaattctg      1020
ttcaccagac aggatttatg tggctcccac acgtgtgaca ctctcgggat ggcagatgtt     1080
ggaactgtat gtgaccccag caggagctgc tcagtcatag aagatgatgg tttgcaagcc     1140
gccttcacca cagcccacga attgggccat gtgtttaaca tgccgcacga tgatgctaag     1200
cactgtgcca gcttgaatgg tgtgactggc gattctcatc tgatggcctc gatgctctcc     1260
agcttagacc atagccagcc ctggtcacct tgcagtgcct acatggtcac gtccttccta     1320
gataatggac acggggaatg tttgatggac aagccccaga atccaatcaa gctcccttct     1380
gatcttcccg gtaccttgta cgatgccaac cgccagtgtc agtttacatt cggagaggaa     1440
tccaagcact gccctgatgc agccagcaca tgtactaccc tgtggtgcac tggcacctcc     1500
ggtggcttac tggtgtgcca aacaaaaacac ttcccttggg cagatggcac cagctgtgga    1560
gaagggaagt ggtgtgtcag tggcaagtgc gtgaacaaga cagacatgaa gcattttgct    1620
actcctgttc atggaagcta a                                               1641
```

<210> SEQ ID NO 15
<211> LENGTH: 561
<212> TYPE: PRT
<213> ORGANISM: Homo sapiens

<400> SEQUENCE: 15

```
Met Gln Arg Ala Val Pro Glu Gly Phe Gly Arg Lys Leu Gly Ser
1               5                  10                  15

Asp Met Gly Asn Ala Glu Arg Ala Pro Gly Ser Arg Ser Phe Gly Pro
                20                  25                  30

Val Pro Thr Leu Leu Leu Ala Ala Leu Leu Ala Val Ser Asp
            35                  40                  45

Ala Leu Gly Arg Pro Ser Glu Glu Asp Glu Glu Leu Val Val Pro Glu
        50                  55                  60

Leu Glu Arg Ala Pro Gly His Gly Thr Thr Arg Leu Arg Leu His Ala
65                  70                  75                  80

Phe Asp Gln Gln Leu Asp Leu Glu Leu Arg Pro Asp Ser Ser Phe Leu
                85                  90                  95

Ala Pro Gly Phe Thr Leu Gln Asn Val Gly Arg Lys Ser Gly Ser Glu
            100                 105                 110

Thr Pro Leu Pro Glu Thr Asp Leu Ala His Cys Phe Tyr Ser Gly Thr
        115                 120                 125

Val Asn Gly Asp Pro Ser Ser Ala Ala Ala Leu Ser Leu Cys Glu Gly
    130                 135                 140

Val Arg Gly Ala Phe Tyr Leu Leu Gly Glu Ala Tyr Phe Ile Gln Pro
145                 150                 155                 160

Leu Pro Ala Ala Ser Glu Arg Leu Ala Thr Ala Pro Gly Glu Lys
                165                 170                 175

Pro Pro Ala Pro Leu Gln Phe His Leu Leu Arg Arg Asn Arg Gln Gly
            180                 185                 190

Asp Val Gly Gly Thr Cys Gly Val Val Asp Asp Glu Pro Arg Pro Thr
        195                 200                 205

Gly Lys Ala Glu Thr Glu Asp Glu Asp Glu Gly Thr Glu Gly Glu Asp
```

Glu Gly Ala Gln Trp Ser Pro Gln Asp Pro Ala Leu Gln Gly Val Gly
225                 230                 235                 240

Gln Pro Thr Gly Thr Gly Ser Ile Arg Lys Lys Arg Phe Val Ser Ser
            245                 250                 255

His Arg Tyr Val Glu Thr Met Leu Val Ala Asp Gln Ser Met Ala Glu
                260                 265                 270

Phe His Gly Ser Gly Leu Lys His Tyr Leu Leu Thr Leu Phe Ser Val
            275                 280                 285

Ala Ala Arg Leu Tyr Lys His Pro Ser Ile Arg Asn Ser Val Ser Leu
290                 295                 300

Val Val Val Lys Ile Leu Val Ile His Asp Glu Gln Lys Gly Pro Glu
305                 310                 315                 320

Val Thr Ser Asn Ala Ala Leu Thr Leu Arg Asn Phe Cys Asn Trp Gln
                325                 330                 335

Lys Gln His Asn Pro Pro Ser Asp Arg Asp Ala Glu His Tyr Asp Thr
                340                 345                 350

Ala Ile Leu Phe Thr Arg Gln Asp Leu Cys Gly Ser Gln Thr Cys Asp
            355                 360                 365

Thr Leu Gly Met Ala Asp Val Gly Thr Val Cys Asp Pro Ser Arg Ser
370                 375                 380

Cys Ser Val Ile Glu Asp Asp Gly Leu Gln Ala Ala Phe Thr Thr Ala
385                 390                 395                 400

His Glu Leu Gly His Val Phe Asn Met Pro His Asp Asp Ala Lys Gln
                405                 410                 415

Cys Ala Ser Leu Asn Gly Val Asn Gln Asp Ser His Met Met Ala Ser
            420                 425                 430

Met Leu Ser Asn Leu Asp His Ser Gln Pro Trp Ser Pro Cys Ser Ala
435                 440                 445

Tyr Met Ile Thr Ser Phe Leu Asp Asn Gly His Gly Glu Cys Leu Met
            450                 455                 460

Asp Lys Pro Gln Asn Pro Ile Gln Leu Pro Gly Asp Leu Pro Gly Thr
465                 470                 475                 480

Ser Tyr Asp Ala Asn Arg Gln Cys Gln Phe Thr Phe Gly Glu Asp Ser
                485                 490                 495

Lys His Cys Pro Asp Ala Ala Ser Thr Cys Ser Thr Leu Trp Cys Thr
            500                 505                 510

Gly Thr Ser Gly Gly Val Leu Val Cys Gln Thr Lys His Phe Pro Trp
515                 520                 525

Ala Asp Gly Thr Ser Cys Gly Glu Gly Lys Trp Cys Ile Asn Gly Lys
530                 535                 540

Cys Val Asn Lys Thr Asp Arg Lys His Phe Asp Thr Pro Phe His Gly
545                 550                 555                 560

Ser

<210> SEQ ID NO 16
<211> LENGTH: 1689
<212> TYPE: DNA
<213> ORGANISM: Homo sapiens

<400> SEQUENCE: 16
gcaatgcagc gagctgtgcc cgaggggttc ggaaggcgca agctgggcag cgacatgggg      60
aacgcggagc gggctccggg gtctcggagc tttgggcccg tacccacgct gctgctgctc     120

| | |
|---|---|
| gccgcggcgc tactggccgt gtcggacgca ctcgggcgcc cctccgagga ggacgaggag | 180 |
| ctagtggtgc cggagctgga gcgcgccccg ggacacggga ccacgcgcct ccgcctgcac | 240 |
| gcctttgacc agcagctgga tctggagctg cggcccgaca gcagcttttt ggcgcccggc | 300 |
| ttcacgctcc agaacgtggg gcgcaaatcc gggtccgaga cgccgcttcc ggaaaccgac | 360 |
| ctggcgcact gcttctactc cggcaccgtg aatggcgatc ccagctcggc tgccgccctc | 420 |
| agcctctgcg agggcgtgcg cggcgccttc tacctgctgg gggaggcgta tttcatccag | 480 |
| ccgctgcccg ccgccagcga gcgcctcgcc accgccgccc aggggagaa gccgccggca | 540 |
| ccactacagt tccacctcct gcggcggaat cggcagggcg acgtcggcgg cacgtgcggg | 600 |
| gtcgtggacg acgagccccg gccgactggg aaagcggaga ccgaagacga ggacgaaggg | 660 |
| actgagggcg aggacgaagg ggctcagtgg tcgccgcagg acccggcact gcaaggcgta | 720 |
| ggacagccca caggaactgg aagcataaga agaagcgat tgtgtccag tcaccgctat | 780 |
| gtggaaacca tgcttgtggc agaccagtcg atggcagaat ccacggcag tggtctaaag | 840 |
| cattaccttc tcacgttgtt ttcggtggca gccagattgt acaaacaccc cagcattcgt | 900 |
| aattcagtta gcctggtggt ggtgaagatc ttggtcatcc acgatgaaca aaggggccg | 960 |
| gaagtgacct ccaatgctgc cctcactctg cggaactttt gcaactggca gaagcagcac | 1020 |
| aacccaccca gtgaccggga tgcagagcac tatgacacag caattctttt caccagacag | 1080 |
| gacttgtgtg ggtcccagac atgtgatact cttgggatgg ctgatgttgg aactgtgtgt | 1140 |
| gatccgagca gaagctgctc cgtcatgaaa atgatggtt acaagctgc cttcaccaca | 1200 |
| gcccatgaat taggccacgt gtttaacatg ccacatgatg atgcaaagca gtgtgccagc | 1260 |
| cttaatggtg tgaaccagga ttcccacatg atggcgtcaa tgctttccaa cctggaccac | 1320 |
| agccagcctt ggtctccttg cagtgcctac atgattacat catttctgga taatggtcat | 1380 |
| ggggaatgtt tgatggacaa gcctcagaat cccatacagc tcccaggcga tctccctggc | 1440 |
| acctcgtacg atgccaaccg gcagtgccag tttacatttg gggaggactc caaacactgc | 1500 |
| cccgatgcag ccagcacatg tagcaccttg tggtgtaccg gcacctctgg tggggtgctg | 1560 |
| gtgtgtcaaa ccaaacactt cccgtgggcg gatggcacca gctgtggaga agggaaatgg | 1620 |
| tgtatcaacg gcaagtgtgt gaacaaaacc gacagaaagc attttgatac gccttttcat | 1680 |
| ggaagctaa | 1689 |

<210> SEQ ID NO 17
<211> LENGTH: 159
<212> TYPE: PRT
<213> ORGANISM: Mus musculus

<400> SEQUENCE: 17

Met Gly Asp Val Gln Arg Ala Ala Arg Ser Arg Gly Ser Leu Ser Ala
1               5                   10                  15

His Met Leu Leu Leu Leu Ala Ser Ile Thr Met Leu Leu Cys Ala
            20                  25                  30

Arg Gly Ala His Gly Arg Pro Thr Glu Lys Lys Met Ser Gly Ile Val
        35                  40                  45

Thr Ser Thr Arg Pro Gly Tyr His Asp Ile Val Thr Ile Pro Ala Gly
    50                  55                  60

Ala Thr Asn Ile Glu Val Lys His Arg Asn Gln Arg Gly Ser Arg Asn
65                  70                  75                  80

Asn Gly Ser Phe Leu Ala Ile Arg Ala Ala Asp Gly Thr Tyr Ile Leu
                85                  90                  95

```
Asn Gly Asn Phe Thr Leu Ser Thr Leu Glu Gln Asp Leu Thr Tyr Lys
            100                 105                 110
Gly Thr Val Leu Arg Tyr Ser Gly Ser Ser Ala Ala Leu Glu Arg Ile
        115                 120                 125
Arg Ser Phe Ser Pro Leu Lys Glu Pro Leu Thr Ile Gln Val Leu Met
    130                 135                 140
Val Gly His Ala Leu Arg Pro Lys Ile Lys Phe Thr Tyr Phe Met
145                 150                 155

<210> SEQ ID NO 18
<211> LENGTH: 483
<212> TYPE: DNA
<213> ORGANISM: Mus musculus

<400> SEQUENCE: 18
gacatggggg acgtccagcg ggcagcgaga tctcggggct ctctgtccgc acacatgctg    60
ttgctgctcc tcgcttccat aacaatgctg ctatgtgcgc ggggcgcaca cgggcgcccc   120
acggagaaga agatgtcagg aatagtcact agtacaagac ctgggtatca tgacattgtc   180
acaattcctg ctggagccac caacattgaa gtgaaacatc ggaatcaaag ggggtccaga   240
aacaatggca gctttctggc tattagagcc gctgatggta cctatattct gaatggaaac   300
ttcactctgt ccacactaga gcaagacctc acctacaaag gtactgtctt aaggtacagt   360
ggttcctcgg ctgcgctgga gagaatccgc agctttagtc cactcaaaga acccttaacc   420
atccaggttc ttatggtagg ccatgctctc cgacccaaaa ttaaattcac ctactttatg   480
taa                                                                483

<210> SEQ ID NO 19
<211> LENGTH: 173
<212> TYPE: PRT
<213> ORGANISM: Homo sapiens

<400> SEQUENCE: 19

Met Gln Arg Ala Val Pro Glu Gly Phe Gly Arg Arg Lys Leu Gly Ser
1               5                   10                  15
Asp Met Gly Asn Ala Glu Arg Ala Pro Gly Ser Arg Ser Phe Gly Pro
            20                  25                  30
Val Pro Thr Leu Leu Leu Ala Ala Ala Leu Leu Ala Val Ser Asp Ala
        35                  40                  45
Ala Leu Gly Arg Pro Ser Glu Lys Lys Ile Ser Gly Ser Val Thr Ser
    50                  55                  60
Ala Lys Pro Gly Tyr His Asp Ile Ile Thr Ile Pro Thr Gly Ala Thr
65                  70                  75                  80
Asn Ile Glu Val Lys Gln Arg Asn Gln Arg Gly Ser Arg Asn Asn Gly
            85                  90                  95
Ser Phe Leu Ala Ile Lys Ala Ala Asp Gly Thr Tyr Ile Leu Asn Gly
            100                 105                 110
Asp Tyr Thr Leu Ser Thr Leu Glu Gln Asp Ile Met Tyr Lys Gly Val
        115                 120                 125
Val Leu Arg Tyr Ser Gly Ser Ser Ala Ala Leu Glu Arg Ile Arg Ser
    130                 135                 140
Phe Ser Pro Leu Lys Glu Pro Leu Thr Ile Gln Val Leu Thr Val Gly
145                 150                 155                 160
Asn Ala Leu Arg Pro Lys Ile Lys Tyr Thr Tyr Phe Val
            165                 170
```

<210> SEQ ID NO 20
<211> LENGTH: 525
<212> TYPE: DNA
<213> ORGANISM: Homo sapiens

<400> SEQUENCE: 20

| | |
|---|---|
| gcaatgcagc gagctgtgcc cgaggggttc ggaaggcgca agctgggcag cgacatgggg | 60 |
| aacgcggagc gggctccggg gtctcggagc tttgggcccg tacccacgct gctgctgctc | 120 |
| gccgcggcgc tactggccgt gtcggacgca ctcgggcgcc cctccgagaa aaaaatatca | 180 |
| ggatcagtta ctagtgcaaa acctggatat catgatatca tcacaattcc aactggagcc | 240 |
| accaacatcg aagtgaaaca gcggaaccag aggggatcca ggaacaatgg cagctttctt | 300 |
| gccatcaaag ctgctgatgg cacatatatt cttaatggtg actacacttt gtccacctta | 360 |
| gagcaagaca ttatgtacaa aggtgttgtc ttgaggtaca gcggctcctc tgcggcattg | 420 |
| gaaagaattc gcagctttag ccctctcaaa gagcccttga ccatccaggt tcttactgtg | 480 |
| ggcaatgccc ttcgacctaa aattaaatac acctacttcg tataa | 525 |

<210> SEQ ID NO 21
<211> LENGTH: 271
<212> TYPE: PRT
<213> ORGANISM: Mus musculus

<400> SEQUENCE: 21

```
Met Gly Asp Val Gln Arg Ala Ala Arg Ser Arg Gly Ser Leu Ser Ala
1               5                   10                  15

His Met Leu Leu Leu Leu Ala Ser Ile Thr Met Leu Leu Cys Ala
            20                  25                  30

Arg Gly Ala His Gly Arg Pro Thr Glu Cys Pro Asp Asn Asn Gly Lys
        35                  40                  45

Thr Phe Arg Glu Glu Gln Cys Glu Ala His Asn Glu Phe Ser Lys Ala
    50                  55                  60

Ser Phe Gly Asn Glu Pro Thr Val Glu Trp Thr Pro Lys Tyr Ala Gly
65                  70                  75                  80

Val Ser Pro Lys Asp Arg Cys Lys Leu Thr Cys Glu Ala Lys Gly Ile
                85                  90                  95

Gly Tyr Phe Phe Val Leu Gln Pro Lys Val Asp Gly Thr Pro Cys
            100                 105                 110

Ser Pro Asp Ser Thr Ser Val Cys Val Gln Gly Gln Cys Val Lys Ala
        115                 120                 125

Gly Cys Asp Arg Ile Ile Asp Ser Lys Lys Phe Asp Lys Cys Gly
    130                 135                 140

Val Cys Gly Gly Asn Gly Ser Thr Cys Lys Lys Met Ser Gly Ile Val
145                 150                 155                 160

Thr Ser Thr Arg Pro Gly Tyr His Asp Ile Val Thr Ile Pro Ala Gly
                165                 170                 175

Ala Thr Asn Ile Glu Val Lys His Arg Asn Gln Arg Gly Ser Arg Asn
            180                 185                 190

Asn Gly Ser Phe Leu Ala Ile Arg Ala Ala Asp Gly Thr Tyr Ile Leu
        195                 200                 205

Asn Gly Asn Phe Thr Leu Ser Thr Leu Glu Gln Asp Leu Thr Tyr Lys
    210                 215                 220

Gly Thr Val Leu Arg Tyr Ser Gly Ser Ser Ala Ala Leu Glu Arg Ile
225                 230                 235                 240
```

Arg Ser Phe Ser Pro Leu Lys Glu Pro Leu Thr Ile Gln Val Leu Met
            245                 250                 255

Val Gly His Ala Leu Arg Pro Lys Ile Lys Phe Thr Tyr Phe Met
            260                 265                 270

<210> SEQ ID NO 22
<211> LENGTH: 819
<212> TYPE: DNA
<213> ORGANISM: Mus musculus

<400> SEQUENCE: 22
gacatggggg acgtccagcg ggcagcgaga tctcggggct ctctgtccgc acacatgctg     60
ttgctgctcc tcgcttccat aacaatgctg ctatgtgcgc ggggcgcaca cgggcgcccc    120
acggagtgtc cagacaataa cggaaaaacg ttcagagagg agcagtgcga ggcgcacaat    180 gagtttttcca aagcttcctt tgggaatgag cccactgtag agtggacacc caagtacgcc    240
ggcgtctcgc caaaggacag gtgcaagctc acctgtgaag ccaaaggcat tggctacttt    300
ttcgtcttac agcccaaggt tgtagatggc actccctgta gtccagactc tacctctgtc    360
tgtgtgcaag ggcagtgtgt gaaagctggc tgtgatcgca tcatagactc aaaaagaag    420 tttgataagt gtggcgtttg tggaggaaac ggttccacat gcaagaagat gtcaggaata    480
gtcactagta caagacctgg gtatcatgac attgtcacaa ttcctgctgg agccaccaac    540
attgaagtga acatcggaa tcaaggggg tccagaaaca atggcagctt tctggctatt    600
agagccgctg atggtaccta tattctgaat ggaaacttca ctctgtccac actagagcaa    660
gacctcacct acaaaggtac tgtcttaagg tacagtggtt cctcggctgc gctggagaga    720
atccgcagct ttagtccact caaagaaccc ttaaccatcc aggttcttat ggtaggccat    780
gctctccgac ccaaaattaa attcacctac tttatgtaa                          819

<210> SEQ ID NO 23
<211> LENGTH: 285
<212> TYPE: PRT
<213> ORGANISM: Homo sapiens

<400> SEQUENCE: 23

Met Gln Arg Ala Val Pro Glu Gly Phe Gly Arg Arg Lys Leu Gly Ser
1               5                   10                  15

Asp Met Gly Asn Ala Glu Arg Ala Pro Gly Ser Arg Ser Phe Gly Pro
            20                  25                  30

Val Pro Thr Leu Leu Leu Ala Ala Ala Leu Leu Ala Val Ser Asp
        35                  40                  45

Ala Leu Gly Arg Pro Ser Glu Cys Pro Asp Asn Gly Lys Thr Phe
    50                  55                  60

Arg Glu Glu Gln Cys Glu Ala His Asn Glu Phe Ser Lys Ala Ser Phe
65                  70                  75                  80

Gly Ser Gly Pro Ala Val Glu Trp Ile Pro Lys Tyr Ala Gly Val Ser
            85                  90                  95

Pro Lys Asp Arg Cys Lys Leu Ile Cys Gln Ala Lys Gly Ile Gly Tyr
            100                 105                 110

Phe Phe Val Leu Gln Pro Lys Val Val Asp Gly Thr Pro Cys Ser Pro
            115                 120                 125

Asp Ser Thr Ser Val Cys Val Gln Gly Gln Cys Val Lys Ala Gly Cys
        130                 135                 140

Asp Arg Ile Ile Asp Ser Lys Lys Lys Phe Asp Lys Cys Gly Val Cys

```
                145                 150                 155                 160
Gly Gly Asn Gly Ser Thr Cys Lys Lys Ile Ser Gly Ser Val Thr Ser
                    165                 170                 175

Ala Lys Pro Gly Tyr His Asp Ile Ile Thr Ile Pro Thr Gly Ala Thr
            180                 185                 190

Asn Ile Glu Val Lys Gln Arg Asn Gln Arg Gly Ser Arg Asn Asn Gly
        195                 200                 205

Ser Phe Leu Ala Ile Lys Ala Ala Asp Gly Thr Tyr Ile Leu Asn Gly
    210                 215                 220

Asp Tyr Thr Leu Ser Thr Leu Glu Gln Asp Ile Met Tyr Lys Gly Val
225                 230                 235                 240

Val Leu Arg Tyr Ser Gly Ser Ser Ala Ala Leu Glu Arg Ile Arg Ser
                245                 250                 255

Phe Ser Pro Leu Lys Glu Pro Leu Thr Ile Gln Val Leu Thr Val Gly
            260                 265                 270

Asn Ala Leu Arg Pro Lys Ile Lys Tyr Thr Tyr Phe Val
        275                 280                 285

<210> SEQ ID NO 24
<211> LENGTH: 861
<212> TYPE: PRT
<213> ORGANISM: Homo sapiens

<400> SEQUENCE: 24

Gly Cys Ala Ala Thr Gly Cys Ala Gly Cys Gly Ala Gly Cys Thr Gly
1               5                   10                  15

Thr Gly Cys Cys Cys Gly Ala Gly Gly Gly Gly Thr Thr Cys Gly Gly
                20                  25                  30

Ala Ala Gly Gly Cys Gly Cys Cys Ala Gly Cys Thr Gly Gly Gly Cys
            35                  40                  45

Ala Gly Cys Gly Gly Cys Ala Thr Gly Gly Gly Ala Ala Cys Gly
        50                  55                  60

Cys Gly Gly Ala Gly Cys Gly Gly Gly Cys Thr Cys Cys Gly Gly Gly
65                  70                  75                  80

Gly Thr Cys Thr Cys Gly Gly Ala Gly Cys Thr Thr Gly Gly Gly
                85                  90                  95

Cys Cys Cys Gly Thr Ala Cys Cys Ala Cys Gly Cys Thr Gly Cys
            100                 105                 110

Thr Gly Cys Thr Gly Cys Thr Cys Gly Cys Cys Gly Cys Gly Gly Cys
    115                 120                 125

Gly Cys Thr Ala Cys Thr Gly Gly Cys Cys Gly Thr Gly Thr Cys Gly
    130                 135                 140

Gly Ala Cys Gly Cys Ala Cys Thr Cys Gly Gly Cys Gly Cys Cys
145                 150                 155                 160

Cys Cys Thr Cys Cys Gly Ala Gly Thr Gly Thr Cys Cys Ala Gly Ala
                165                 170                 175

Cys Ala Ala Thr Ala Ala Thr Gly Gly Ala Ala Ala Ala Cys Cys
            180                 185                 190

Thr Thr Thr Ala Gly Ala Gly Ala Gly Gly Ala Ala Cys Ala Ala Thr
        195                 200                 205

Gly Thr Gly Ala Ala Gly Cys Ala Cys Ala Ala Cys Gly Ala
    210                 215                 220

Gly Thr Thr Thr Cys Ala Ala Ala Ala Gly Cys Thr Thr Cys Cys
225                 230                 235                 240
```

-continued

```
Thr Thr Thr Gly Gly Gly Ala Gly Thr Gly Gly Gly Cys Cys Thr Gly
                245                 250                 255

Cys Gly Gly Thr Gly Gly Ala Ala Thr Gly Gly Ala Thr Thr Cys Cys
            260                 265                 270

Cys Ala Ala Gly Thr Ala Cys Gly Cys Thr Gly Gly Cys Gly Thr Cys
        275                 280                 285

Thr Cys Ala Cys Cys Ala Ala Ala Gly Gly Ala Cys Ala Gly Gly Thr
    290                 295                 300

Gly Cys Ala Ala Gly Cys Thr Cys Ala Thr Cys Thr Gly Cys Cys Ala
305                 310                 315                 320

Ala Gly Cys Cys Ala Ala Ala Gly Gly Cys Ala Thr Thr Gly Gly Cys
                325                 330                 335

Thr Ala Cys Thr Thr Cys Thr Thr Cys Gly Thr Thr Thr Thr Gly Cys
            340                 345                 350

Ala Gly Cys Cys Cys Ala Ala Gly Gly Thr Thr Gly Thr Ala Gly Ala
        355                 360                 365

Thr Gly Gly Thr Ala Cys Thr Cys Cys Ala Thr Gly Thr Ala Gly Cys
    370                 375                 380

Cys Cys Ala Gly Ala Thr Thr Cys Cys Ala Cys Cys Thr Cys Thr Gly
385                 390                 395                 400

Thr Cys Thr Gly Thr Gly Thr Gly Cys Ala Ala Gly Gly Ala Cys Ala
                405                 410                 415

Gly Thr Gly Thr Gly Thr Ala Ala Ala Ala Gly Cys Thr Gly Gly Thr
            420                 425                 430

Thr Gly Thr Gly Ala Thr Cys Gly Cys Ala Thr Cys Ala Thr Ala Gly
        435                 440                 445

Ala Cys Thr Cys Cys Ala Ala Ala Ala Ala Gly Ala Ala Gly Thr Thr
    450                 455                 460

Thr Gly Ala Thr Ala Ala Ala Thr Gly Thr Gly Gly Thr Gly Thr Thr
465                 470                 475                 480

Thr Gly Cys Gly Gly Gly Gly Gly Ala Ala Ala Thr Gly Gly Ala Thr
                485                 490                 495

Cys Thr Ala Cys Thr Thr Gly Thr Ala Ala Ala Ala Ala Ala Ala Thr
            500                 505                 510

Ala Thr Cys Ala Gly Gly Ala Thr Cys Ala Gly Thr Thr Ala Cys Thr
        515                 520                 525

Ala Gly Thr Gly Cys Ala Ala Ala Ala Cys Cys Thr Gly Gly Ala Thr
    530                 535                 540

Ala Thr Cys Ala Thr Gly Ala Thr Ala Thr Cys Ala Thr Cys Ala Cys
545                 550                 555                 560

Ala Ala Thr Thr Cys Cys Ala Ala Cys Thr Gly Gly Ala Gly Cys Cys
                565                 570                 575

Ala Cys Cys Ala Ala Cys Ala Thr Cys Gly Ala Ala Gly Thr Gly Ala
            580                 585                 590

Ala Ala Cys Ala Gly Cys Gly Gly Ala Ala Cys Cys Ala Gly Ala Gly
        595                 600                 605

Gly Gly Gly Ala Thr Cys Cys Ala Gly Gly Ala Ala Cys Ala Ala Thr
    610                 615                 620

Gly Gly Cys Ala Gly Cys Thr Thr Thr Cys Thr Thr Gly Cys Cys Ala
625                 630                 635                 640

Thr Cys Ala Ala Ala Gly Cys Thr Gly Cys Thr Gly Ala Thr Gly Gly
                645                 650                 655

Cys Ala Cys Ala Thr Ala Thr Ala Thr Thr Cys Thr Thr Ala Ala Thr
```

-continued

```
                    660                 665                 670
Gly Gly Thr Gly Ala Cys Thr Ala Cys Ala Cys Thr Thr Thr Gly Thr
                675                 680                 685
Cys Cys Ala Cys Cys Thr Thr Ala Gly Ala Gly Cys Ala Ala Gly Ala
            690                 695                 700
Cys Ala Thr Thr Ala Thr Gly Thr Ala Cys Ala Ala Ala Gly Gly Thr
705                 710                 715                 720
Gly Thr Thr Gly Thr Cys Thr Thr Gly Ala Gly Gly Thr Ala Cys Ala
                725                 730                 735
Gly Cys Gly Gly Cys Thr Cys Cys Thr Cys Thr Gly Cys Gly Gly Cys
            740                 745                 750
Ala Thr Thr Gly Gly Ala Ala Ala Gly Ala Ala Thr Cys Gly Cys
            755                 760                 765
Ala Gly Cys Thr Thr Thr Ala Gly Cys Cys Cys Thr Cys Thr Cys Ala
        770                 775                 780
Ala Ala Gly Ala Gly Cys Cys Thr Thr Gly Ala Cys Cys Ala Thr
785                 790                 795                 800
Cys Cys Ala Gly Gly Thr Thr Cys Thr Thr Ala Cys Thr Gly Thr Gly
                805                 810                 815
Gly Gly Cys Ala Ala Thr Gly Cys Cys Cys Thr Thr Cys Gly Ala Cys
            820                 825                 830
Cys Thr Ala Ala Ala Thr Ala Ala Ala Thr Ala Cys Ala Cys
        835                 840                 845
Cys Thr Ala Cys Thr Thr Cys Gly Thr Ala Thr Ala Ala
    850                 855                 860

<210> SEQ ID NO 25
<211> LENGTH: 447
<212> TYPE: PRT
<213> ORGANISM: Mus musculus

<400> SEQUENCE: 25

Met Gly Asp Val Gln Arg Ala Ala Arg Ser Arg Gly Ser Leu Ser Ala
1               5                   10                  15

His Met Leu Leu Leu Leu Ala Ser Ile Thr Met Leu Leu Cys Ala
                20                  25                  30

Arg Gly Ala His Gly Arg Pro Thr Glu Trp Gly Pro Trp Gly Pro Trp
            35                  40                  45

Gly Asp Cys Ser Arg Thr Cys Gly Gly Gly Val Gln Tyr Thr Met Arg
    50                  55                  60

Glu Cys Asp Asn Pro Val Pro Lys Asn Gly Gly Lys Tyr Cys Glu Gly
65                  70                  75                  80

Lys Arg Val Arg Tyr Arg Ser Cys Asn Ile Glu Asp Cys Pro Asp Asn
                85                  90                  95

Asn Gly Lys Thr Phe Arg Glu Glu Gln Cys Glu Ala His Asn Glu Phe
            100                 105                 110

Ser Lys Ala Ser Phe Gly Asn Glu Pro Thr Val Glu Trp Thr Pro Lys
        115                 120                 125

Tyr Ala Gly Val Ser Pro Lys Asp Arg Cys Lys Leu Thr Cys Glu Ala
    130                 135                 140

Lys Gly Ile Gly Tyr Phe Phe Val Leu Gln Pro Lys Val Val Asp Gly
145                 150                 155                 160

Thr Pro Cys Ser Pro Asp Ser Thr Ser Val Cys Val Gln Gly Gln Cys
                165                 170                 175
```

| | | | | | | | | | | | |
|---|---|---|---|---|---|---|---|---|---|---|---|
|Val|Lys|Ala|Gly|Cys|Asp|Arg|Ile|Ile|Asp|Ser|Lys|Lys|Phe|Asp|
| | | |180| | | | |185| | | |190| | |

Val Lys Ala Gly Cys Asp Arg Ile Ile Asp Ser Lys Lys Phe Asp
              180                 185                 190

Lys Cys Gly Val Cys Gly Gly Asn Gly Ser Thr Cys Lys Lys Met Ser
            195                 200                 205

Gly Ile Val Thr Ser Thr Arg Pro Gly Tyr His Asp Ile Val Thr Ile
        210                 215                 220

Pro Ala Gly Ala Thr Asn Ile Glu Val Lys His Arg Asn Gln Arg Gly
225                 230                 235                 240

Ser Arg Asn Asn Gly Ser Phe Leu Ala Ile Arg Ala Ala Asp Gly Thr
                245                 250                 255

Tyr Ile Leu Asn Gly Asn Phe Thr Leu Ser Thr Leu Glu Gln Asp Leu
            260                 265                 270

Thr Tyr Lys Gly Thr Val Leu Arg Tyr Ser Gly Ser Ser Ala Ala Leu
        275                 280                 285

Glu Arg Ile Arg Ser Phe Ser Pro Leu Lys Glu Pro Leu Thr Ile Gln
    290                 295                 300

Val Leu Met Val Gly His Ala Leu Arg Pro Lys Ile Lys Phe Thr Tyr
305                 310                 315                 320

Phe Met Lys Lys Lys Thr Glu Ser Phe Asn Ala Ile Pro Thr Phe Ser
                325                 330                 335

Glu Trp Val Ile Glu Glu Trp Gly Cys Ser Lys Thr Cys Gly Ser
            340                 345                 350

Gly Trp Gln Arg Arg Val Val Gln Cys Arg Asp Ile Asn Gly His Pro
        355                 360                 365

Ala Ser Glu Cys Ala Lys Glu Val Lys Pro Ala Ser Thr Arg Pro Cys
    370                 375                 380

Ala Asp Leu Pro Cys Pro His Trp Gln Val Gly Asp Trp Ser Pro Cys
385                 390                 395                 400

Ser Lys Thr Cys Gly Lys Gly Tyr Lys Lys Arg Thr Leu Lys Cys Val
                405                 410                 415

Ser His Asp Gly Gly Val Leu Ser Asn Glu Ser Cys Asp Pro Leu Lys
            420                 425                 430

Lys Pro Lys His Tyr Ile Asp Phe Cys Thr Leu Thr Gln Cys Ser
        435                 440                 445

<210> SEQ ID NO 26
<211> LENGTH: 1347
<212> TYPE: DNA
<213> ORGANISM: Mus musculus

<400> SEQUENCE: 26

```
gacatggggg acgtccagcg ggcagcgaga tctcggggct ctctgtccgc acacatgctg      60
ttgctgctcc tcgcttccat aacaatgctg ctatgtgcgc ggggcgcaca cgggcgcccc     120
acggagtggg gaccatgggg accgtgggga gactgctcaa gaacctgtgg tggtggagtt     180
caatacacaa tgagagaatg tgacaaccca gtcccaaaga acggagggaa gtactgtgaa     240
ggcaaacgag tccgctacag gtcctgtaac atcgaggact gtccagacaa taacggaaaa     300
acgttcagag aggagcagtg cgaggcgcac aatgagtttt ccaaagcttc ctttgggaat     360
gagcccactg tagagtggac acccaagtac gccggcgtct cgccaaagga caggtgcaag     420
ctcacctgtg aagccaaagg cattggctac ttttttcgtct tacagcccaa ggttgtagat     480
ggcactccct gtagtccaga ctctacctct gtctgtgtgc aagggcagtg tgtgaaagct     540
ggctgtgatc gcatccatga ctccaaaaag aagtttgata gtgtggcgt ttgtggagga     600
```

```
aacggttcca catgcaagaa gatgtcagga atagtcacta gtacaagacc tgggtatcat    660
gacattgtca caattcctgc tggagccacc aacattgaag tgaaacatcg gaatcaaagg    720
gggtccagaa acaatggcag ctttctggct attagagccg ctgatggtac ctatattctg    780
aatgaaaact tcactctgtc cacactagag caagacctca cctacaaagg tactgtctta    840
aggtacagtg gttcctcggc tgcgctggag agaatccgca gctttagtcc actcaaagaa    900
cccttaacca tccaggttct tatggtaggc catgctctcc gacccaaaat taaattcacc    960
tactttatga agaagaagac agagtcattc aacgccattc ccacattttc tgagtgggtg   1020
attgaagagt gggggagtg ctccaagaca tgcggctcag gttggcagag aagagtagtg   1080
cagtgcagag acattaatgg acaccctgct tccgaatgtg caaggaagt gaagccagcc   1140
agtaccagac cttgtgcaga ccttccttgc ccacactggc aggtggggga ttggtcacca   1200
tgttccaaaa cttgcgggaa gggttacaag aagagaacct tgaaatgtgt gtcccacgat   1260
ggggcgtgt tatcaaatga gagctgtgat cctttgaaga agccaaagca ttacattgac   1320
ttttgcacac tgacacagtg cagttaa                                      1347
```

<210> SEQ ID NO 27
<211> LENGTH: 410
<212> TYPE: PRT
<213> ORGANISM: Homo sapiens

<400> SEQUENCE: 27

```
Met Gln Arg Ala Val Pro Glu Gly Phe Gly Arg Arg Lys Leu Gly Ser
1               5                   10                  15

Asp Met Gly Asn Ala Glu Arg Ala Pro Gly Ser Arg Ser Phe Gly Pro
            20                  25                  30

Val Pro Thr Leu Leu Leu Ala Ala Ala Leu Leu Ala Val Ser Asp
        35                  40                  45

Ala Leu Gly Arg Pro Ser Glu Cys Pro Asp Asn Asn Gly Lys Thr Phe
    50                  55                  60

Arg Glu Glu Gln Cys Glu Ala His Asn Glu Phe Ser Lys Ala Ser Phe
65                  70                  75                  80

Gly Ser Gly Pro Ala Val Glu Trp Ile Pro Lys Tyr Ala Gly Val Ser
                85                  90                  95

Pro Lys Asp Arg Cys Lys Leu Ile Cys Gln Ala Lys Gly Ile Gly Tyr
            100                 105                 110

Phe Phe Val Leu Gln Pro Lys Val Val Asp Gly Thr Pro Cys Ser Pro
        115                 120                 125

Asp Ser Thr Ser Val Cys Val Gln Gly Gln Cys Val Lys Ala Gly Cys
    130                 135                 140

Asp Arg Ile Ile Asp Ser Lys Lys Lys Phe Asp Lys Cys Gly Val Cys
145                 150                 155                 160

Gly Gly Asn Gly Ser Thr Cys Lys Lys Ile Ser Gly Ser Val Thr Ser
                165                 170                 175

Ala Lys Pro Gly Tyr His Asp Ile Ile Thr Ile Pro Thr Gly Ala Thr
            180                 185                 190

Asn Ile Glu Val Lys Gln Arg Asn Gln Arg Gly Ser Arg Asn Asn Gly
        195                 200                 205

Ser Phe Leu Ala Ile Lys Ala Ala Asp Gly Thr Tyr Ile Leu Asn Gly
    210                 215                 220

Asp Tyr Thr Leu Ser Thr Leu Glu Gln Asp Ile Met Tyr Lys Gly Val
225                 230                 235                 240
```

```
Val Leu Arg Tyr Ser Gly Ser Ser Ala Ala Leu Glu Arg Ile Arg Ser
                245                 250                 255

Phe Ser Pro Leu Lys Glu Pro Leu Thr Ile Gln Val Leu Thr Val Gly
            260                 265                 270

Asn Ala Leu Arg Pro Lys Ile Lys Tyr Thr Tyr Phe Val Lys Lys Lys
        275                 280                 285

Lys Glu Ser Phe Asn Ala Ile Pro Thr Phe Ser Ala Trp Val Ile Glu
    290                 295                 300

Glu Trp Gly Glu Cys Ser Lys Ser Cys Glu Leu Gly Trp Gln Arg Arg
305                 310                 315                 320

Leu Val Glu Cys Arg Asp Ile Asn Gly Gln Pro Ala Ser Glu Cys Ala
                325                 330                 335

Lys Glu Val Lys Pro Ala Ser Thr Arg Pro Cys Ala Asp His Pro Cys
            340                 345                 350

Pro Gln Trp Gln Leu Gly Glu Trp Ser Ser Cys Ser Lys Thr Cys Gly
        355                 360                 365

Lys Gly Tyr Lys Lys Arg Ser Leu Lys Cys Leu Ser His Asp Gly Gly
    370                 375                 380

Val Leu Ser His Glu Ser Cys Asp Pro Leu Lys Lys Pro Lys His Phe
385                 390                 395                 400

Ile Asp Phe Cys Thr Met Ala Glu Cys Ser
                405                 410

<210> SEQ ID NO 28
<211> LENGTH: 1389
<212> TYPE: DNA
<213> ORGANISM: Homo sapiens

<400> SEQUENCE: 28
gcaatgcagc gagctgtgcc cgaggggttc ggaaggcgca agctgggcag cgacatgggg      60
aacgcggagc gggctccggg gtctcggagc tttgggcccg tacccacgct gctgctgctc     120
gccgcggcgc tactggccgt gtcggacgca ctcgggcgcc cctccgagtg gggaatgtgg     180
gggccttggg gagactgttc gagaacgtgc ggtggaggag tccagtacac gatgagggaa     240
tgtgacaacc cagtcccaaa gaatggaggg aagtactgtg aaggcaaacg agtgcgctac     300
agatcctgta accttgagga ctgtccagac aataatggaa aaacctttag agaggaacaa     360
tgtgaagcac acaacgagtt ttcaaaagct tcctttggga gtgggcctgc ggtggaatgg     420
attcccaagt acgctggcgt ctcaccaaag gacaggtgca agctcatctg ccaagccaaa     480
ggcattggct acttcttcgt tttgcagccc aaggttgtag atggtactcc atgtagccca     540
gattccacct ctgtctgtgt gcaaggacag tgtgtaaaag ctggttgtga tcgcatcata     600
gactccaaaa agaagtttga taaatgtggt gtttgcgggg gaaatggatc tacttgtaaa     660
aaaatatcag gatcagttac tagtgcaaaa cctggatatc atgatatcat cacaattcca     720
actggagcca ccaacatcga agtgaaacag cggaaccaga ggggatccag gaacaatggc     780
agctttcttg ccatcaaagc tgctgatggc acatatattc ttaatggtga ctacactttg     840
tccaccttag agcaagacat tatgtacaaa ggtgttgtct tgaggtacag cggctcctct     900
gcggcattgg aaagaattcg cagctttagc cctctcaaag agcccttgac catccaggtt     960
cttactgtgg gcaatgccct tcgacctaaa attaaataca cctacttcgt aaagaagaag    1020
aaggaatctt tcaatgctat ccccactttt tcagcatggg tcattgaaga gtggggcgaa    1080
tgttctaagt catgtgaatt gggttggcag agaagactgg tagaatgccg agacattaat    1140
```

```
ggacagcctg cttccgagtg tgcaaaggaa gtgaagccag ccagcaccag accttgtgca    1200
gaccatccct gcccccagtg gcagctgggg gagtggtcat catgttctaa gacctgtggg    1260
aagggttaca aaaaagaag cttgaagtgt ctgtcccatg atggaggggt gttatctcat     1320
gagagctgtg atcctttaaa gaaacctaaa catttcatag acttttgcac aatggcagaa    1380
tgcagttaa                                                            1389
```

<210> SEQ ID NO 29
<211> LENGTH: 951
<212> TYPE: PRT
<213> ORGANISM: Mus musculus

<400> SEQUENCE: 29

```
Met Gly Asp Val Gln Arg Ala Ala Arg Ser Arg Gly Ser Leu Ser Ala
1               5                   10                  15

His Met Leu Leu Leu Leu Ala Ser Ile Thr Met Leu Leu Cys Ala
            20                  25                  30

Arg Gly Ala His Gly Arg Pro Thr Glu Glu Asp Glu Glu Leu Val Leu
        35                  40                  45

Pro Ser Leu Glu Arg Ala Pro Gly His Asp Ser Thr Thr Thr Arg Leu
    50                  55                  60

Arg Leu Asp Ala Phe Gly Gln Gln Leu His Leu Lys Leu Gln Pro Asp
65                  70                  75                  80

Ser Gly Phe Leu Ala Pro Gly Phe Thr Leu Gln Thr Val Gly Arg Ser
                85                  90                  95

Pro Gly Ser Glu Ala Gln His Leu Asp Pro Thr Gly Asp Leu Ala His
            100                 105                 110

Cys Phe Tyr Ser Gly Thr Val Asn Gly Asp Pro Gly Ser Ala Ala Ala
        115                 120                 125

Leu Ser Leu Cys Glu Gly Val Arg Gly Ala Phe Tyr Leu Gln Gly Glu
    130                 135                 140

Glu Phe Phe Ile Gln Pro Ala Pro Gly Val Ala Thr Glu Arg Leu Ala
145                 150                 155                 160

Pro Ala Val Pro Glu Glu Glu Ser Ser Ala Arg Pro Gln Phe His Ile
                165                 170                 175

Leu Arg Arg Arg Arg Gly Ser Gly Gly Ala Lys Cys Gly Val Met
            180                 185                 190

Asp Asp Glu Thr Leu Pro Thr Ser Asp Ser Arg Pro Glu Ser Gln Asn
        195                 200                 205

Thr Arg Asn Gln Trp Pro Val Arg Asp Pro Thr Pro Gln Asp Ala Gly
    210                 215                 220

Lys Pro Ser Gly Pro Gly Ser Ile Arg Lys Arg Phe Val Ser Ser
225                 230                 235                 240

Pro Arg Tyr Val Glu Thr Met Leu Val Ala Asp Gln Ser Met Ala Asp
                245                 250                 255

Phe His Gly Ser Gly Leu Lys His Tyr Leu Leu Thr Leu Phe Ser Val
            260                 265                 270

Ala Ala Arg Phe Tyr Lys His Pro Ser Ile Arg Asn Ser Ile Ser Leu
        275                 280                 285

Val Val Val Lys Ile Leu Val Ile Tyr Glu Glu Gln Lys Gly Pro Glu
    290                 295                 300

Val Thr Ser Asn Ala Ala Leu Thr Leu Arg Asn Phe Cys Asn Trp Gln
305                 310                 315                 320

Lys Gln His Asn Ser Pro Ser Asp Arg Asp Pro Glu His Tyr Asp Thr
```

```
                    325                 330                 335
Ala Ile Leu Phe Thr Arg Gln Asp Leu Cys Gly Ser His Thr Cys Asp
                340                 345                 350

Thr Leu Gly Met Ala Asp Val Gly Thr Val Cys Asp Pro Ser Arg Ser
                355                 360                 365

Cys Ser Val Ile Glu Asp Asp Gly Leu Gln Ala Ala Phe Thr Thr Ala
            370                 375                 380

His Gln Leu Gly His Val Phe Asn Met Pro His Asp Asp Ala Lys His
385                 390                 395                 400

Cys Ala Ser Leu Asn Gly Val Thr Gly Asp Ser His Leu Met Ala Ser
                405                 410                 415

Met Leu Ser Ser Leu Asp His Ser Gln Pro Trp Ser Pro Cys Ser Ala
                420                 425                 430

Tyr Met Val Thr Ser Phe Leu Asp Asn Gly His Gly Glu Cys Leu Met
            435                 440                 445

Asp Lys Pro Gln Asn Pro Ile Lys Leu Pro Ser Asp Leu Pro Gly Thr
                450                 455                 460

Leu Tyr Asp Ala Asn Arg Gln Cys Gln Phe Thr Phe Gly Glu Glu Ser
465                 470                 475                 480

Lys His Cys Pro Asp Ala Ala Ser Thr Cys Thr Thr Leu Trp Cys Thr
                485                 490                 495

Gly Thr Ser Gly Gly Leu Leu Val Cys Gln Thr Lys His Phe Pro Trp
            500                 505                 510

Ala Asp Gly Thr Ser Cys Gly Glu Gly Lys Trp Cys Val Ser Gly Lys
            515                 520                 525

Cys Val Asn Lys Thr Asp Met Lys His Phe Ala Thr Pro Val His Gly
530                 535                 540

Ser Trp Gly Pro Trp Gly Pro Trp Gly Asp Cys Ser Arg Thr Cys Gly
545                 550                 555                 560

Gly Gly Val Gln Tyr Thr Met Arg Glu Cys Asp Asn Pro Val Pro Lys
                565                 570                 575

Asn Gly Gly Lys Tyr Cys Glu Gly Lys Arg Val Arg Tyr Arg Ser Cys
                580                 585                 590

Asn Ile Glu Asp Cys Pro Asp Asn Asn Gly Lys Thr Phe Arg Glu Glu
            595                 600                 605

Gln Cys Glu Ala His Asn Glu Phe Ser Lys Ala Ser Phe Gly Asn Glu
        610                 615                 620

Pro Thr Val Glu Trp Thr Pro Lys Tyr Ala Gly Val Ser Pro Lys Asp
625                 630                 635                 640

Arg Cys Lys Leu Thr Cys Glu Ala Lys Gly Ile Gly Tyr Phe Phe Val
                645                 650                 655

Leu Gln Pro Lys Val Val Asp Gly Thr Pro Cys Ser Pro Asp Ser Thr
                660                 665                 670

Ser Val Cys Val Gln Gly Gln Cys Val Lys Ala Gly Cys Asp Arg Ile
            675                 680                 685

Ile Asp Ser Lys Lys Phe Asp Lys Cys Gly Val Cys Gly Gly Asn
            690                 695                 700

Gly Ser Thr Cys Lys Lys Met Ser Gly Ile Val Thr Ser Thr Arg Pro
705                 710                 715                 720

Gly Tyr His Asp Ile Val Thr Ile Pro Ala Gly Ala Thr Asn Ile Glu
            725                 730                 735

Val Lys His Arg Asn Gln Arg Gly Ser Arg Asn Asn Gly Ser Phe Leu
            740                 745                 750
```

```
Ala Ile Arg Ala Ala Asp Gly Thr Tyr Ile Leu Asn Gly Asn Phe Thr
            755                 760                 765

Leu Ser Thr Leu Glu Gln Asp Leu Thr Tyr Lys Gly Thr Val Leu Arg
        770                 775                 780

Tyr Ser Gly Ser Ser Ala Ala Leu Glu Arg Ile Arg Ser Phe Ser Pro
785                 790                 795                 800

Leu Lys Glu Pro Leu Thr Ile Gln Val Leu Met Val Gly His Ala Leu
                805                 810                 815

Arg Pro Lys Ile Lys Phe Thr Tyr Phe Met Lys Lys Thr Glu Ser
            820                 825                 830

Phe Asn Ala Ile Pro Thr Phe Ser Glu Trp Val Ile Glu Glu Trp Gly
        835                 840                 845

Glu Cys Ser Lys Thr Cys Gly Ser Gly Trp Gln Arg Arg Val Val Gln
    850                 855                 860

Cys Arg Asp Ile Asn Gly His Pro Ala Ser Glu Cys Ala Lys Glu Val
865                 870                 875                 880

Lys Pro Ala Ser Thr Arg Pro Cys Ala Asp Leu Pro Cys Pro His Trp
                885                 890                 895

Gln Val Gly Asp Trp Ser Pro Cys Ser Lys Thr Cys Gly Lys Gly Tyr
            900                 905                 910

Lys Lys Arg Thr Leu Lys Cys Val Ser His Asp Gly Gly Val Leu Ser
        915                 920                 925

Asn Glu Ser Cys Asp Pro Leu Lys Lys Pro Lys His Tyr Ile Asp Phe
    930                 935                 940

Cys Thr Leu Thr Gln Cys Ser
945                 950

<210> SEQ ID NO 30
<211> LENGTH: 2859
<212> TYPE: DNA
<213> ORGANISM: Mus musculus

<400> SEQUENCE: 30
gacatggggg acgtccagcg ggcagcgaga tctcggggct ctctgtccgc acacatgctg      60
ttgctgctcc tcgcttccat aacaatgctg ctatgtgcgc ggggcgcaca cgggcgcccc     120
acggaggaag atgaggagct ggtcctgccc tcgctggagc gcgccccggg ccacgattcc     180
accaccacac gccttcgtct ggacgccttt ggccagcagc tacatctgaa gttgcagccg     240
gacagcggtt tcttggcgcc tggcttcacc ctgcagactg tggggcgcag tcccgggtcc     300
gaggcacaac atctggaccc caccggggac ctggctcact gcttctactc tggcacggtg     360
aacggtgatc ccggctctgc cgcagccctc agcctctgtg aaggtgtgcg tggtgccttc     420
tacctacaag agaggagtt cttcattcag ccagcgcctg agtggccac cgagcgcctg     480 gccccctgccg tgcccgagga ggagtcatcc gcacggccgc agttccacat cctgaggcga     540
aggcggcggg gcagtggcgg cgccaagtgc ggcgtcatgg acgacgagac cctgccaacc     600
agcgactcgc gacccgagag ccagaacacc cggaaccagt ggcctgtgcg ggaccccacg     660
cctcaggacg cgggaaagcc atcaggacca ggaagcataa ggaagaagcg atttgtgtcc     720 agccccgtt atgtggaaac catgctcgtg gctgaccagt ccatggccga cttccacggc     780
agcggtctaa agcattacct tctaacccctg ttctcggtgg cagccaggtt ttacaagcat     840
cccagcatta ggaattcaat tagcctggtg gtggtgaaga tcttggtcat atatgaggag     900
cagaagggac cagaagttac ctccaatgca gctctcaccc ttcggaattt ctgcaactgg     960
```

-continued

```
cagaaacaac acaacagccc cagtgaccgg gatccagagc actatgacac tgcaattctg   1020
ttcaccagac aggatttatg tggctcccac acgtgtgaca ctctcgggat ggcagatgtt   1080
ggaactgtat gtgacccccag caggagctgc tcagtcatag aagatgatgg tttgcaagcc   1140
gccttcacca cagcccacca attgggccat gtgtttaaca tgccgcacga tgatgctaag   1200
cactgtgcca gcttgaatgg tgtgactggc gattctcatc tgatggcctc gatgctctcc   1260
agcttagacc atagccagcc ctggtcacct tgcagtgcct acatggtcac gtccttccta   1320
gataatggac acggggaatg tttgatggac aagccccaga tccaatcaa gctcccttct   1380 gatcttcccg gtaccttgta cgatgccaac cgccagtgtc agtttacatt cggagaggaa   1440
tccaagcact gccctgatgc agccagcaca tgtactaccc tgtggtgcac tggcacctcc   1500
ggtggcttac tggtgtgcca acaaaaacac ttcccttggg cagatggcac cagctgtgga   1560
gaagggaagt ggtgtgtcag tggcaagtgc gtgaacaaga cagacatgaa gcattttgct   1620
actcctgttc atggaagctg ggaccatggg gaccgtgggg gagactgctc aagaacctgt   1680
ggtggtggag ttcaatacac aatgagagaa tgtgacaacc cagtcccaaa gaacggaggg   1740
aagtactgtg aaggcaaacg agtccgctac aggtcctgta acatcgagga ctgtccagac   1800
aataacggaa aaacgttcag agaggagcag tgcgaggcgc acaatgagtt tccaaagct   1860 tccttttggga atgagcccac tgtagagtgg acacccaagt acgccggcgt ctcgccaaag   1920
gacaggtgca agctcacctg tgaagccaaa ggcattggct acttttttcgt cttacagccc   1980 aaggttgtag atggcactcc ctgtagtcca gactctacct ctgtctgtgt gcaagggcag   2040
tgtgtgaaag ctggctgtga tcgcatcata gactccaaaa agaagtttga taagtgtggc   2100
gtttgtggag gaaacggttc cacatgcaag aagatgtcag gaatagtcac tagtacaaga   2160
cctgggtatc atgacattgt cacaattcct gctggagcca ccaacattga agtgaaacat   2220
cggaatcaaa gggggtccag aaacaatggc agctttctgg ctattagagc cgctgatggt   2280
acctatattc tgaatggaaa cttcactctg tccacactag agcaagacct cacctacaaa   2340
ggtactgtct taaggtacag tggttcctcg gctgcgctgg agagaatccg cagctttagt   2400
ccactcaaag aacccttaac catccaggtt cttatggtag ccatgctct ccgacccaaa   2460 attaaattca cctactttat gaagaagaag acagagtcat tcaacgccat tcccacattt   2520
tctgagtggg tgattgaaga gtggggggag tgctccaaga catgcggctc aggttggcag   2580
agaagagtag tgcagtgcag agacattaat ggacaccctg cttccgaatg tgcaaaggaa   2640
gtgaagccag ccagtaccag accttgtgca gaccttcctt gcccacactg gcaggtgggg   2700
gattggtcac catgttccaa aacttgcggg aagggttaca agaagagaac cttgaaatgt   2760
gtgtcccacg atgggggcgt gttatcaaat gagagctgtg atccttttgaa gaagccaaag   2820 cattacattg acttttgcac actgacacag tgcagttaa   2859
```

<210> SEQ ID NO 31
<211> LENGTH: 950
<212> TYPE: PRT
<213> ORGANISM: Homo sapiens

<400> SEQUENCE: 31

```
Met Gly Asn Ala Glu Arg Ala Pro Gly Ser Arg Ser Phe Gly Pro Val
 1               5                  10                  15

Pro Thr Leu Leu Leu Leu Ala Ala Ala Leu Leu Ala Val Ser Asp Ala
            20                  25                  30
```

-continued

```
Leu Gly Arg Pro Ser Glu Glu Asp Glu Leu Val Val Pro Glu Leu
        35                  40                  45

Glu Arg Ala Pro Gly His Gly Thr Thr Arg Leu Arg Leu His Ala Phe
    50                  55                  60

Asp Gln Gln Leu Asp Leu Glu Leu Arg Pro Asp Ser Ser Phe Leu Ala
65                  70                  75                  80

Pro Gly Phe Thr Leu Gln Asn Val Gly Arg Lys Ser Gly Ser Glu Thr
                85                  90                  95

Pro Leu Pro Glu Thr Asp Leu Ala His Cys Phe Tyr Ser Gly Thr Val
            100                 105                 110

Asn Gly Asp Pro Ser Ser Ala Ala Leu Ser Leu Cys Glu Gly Val
            115                 120                 125

Arg Gly Ala Phe Tyr Leu Leu Gly Glu Ala Tyr Phe Ile Gln Pro Leu
        130                 135                 140

Pro Ala Ala Ser Glu Arg Leu Ala Thr Ala Ala Pro Gly Glu Lys Pro
145                 150                 155                 160

Pro Ala Pro Leu Gln Phe His Leu Leu Arg Arg Asn Arg Gln Gly Asp
                165                 170                 175

Val Gly Gly Thr Cys Gly Val Val Asp Asp Glu Pro Arg Pro Thr Gly
            180                 185                 190

Lys Ala Glu Thr Glu Asp Glu Asp Glu Gly Thr Glu Gly Glu Asp Glu
        195                 200                 205

Gly Ala Gln Trp Ser Pro Gln Asp Pro Ala Leu Gln Gly Val Gly Gln
    210                 215                 220

Pro Thr Gly Thr Gly Ser Ile Arg Lys Lys Arg Phe Val Ser Ser His
225                 230                 235                 240

Arg Tyr Val Glu Thr Met Leu Val Ala Asp Gln Ser Met Ala Glu Phe
                245                 250                 255

His Gly Ser Gly Leu Lys His Tyr Leu Leu Thr Leu Phe Ser Val Ala
            260                 265                 270

Ala Arg Leu Tyr Lys His Pro Ser Ile Arg Asn Ser Val Ser Leu Val
        275                 280                 285

Val Val Lys Ile Leu Val Ile His Asp Glu Gln Lys Gly Pro Glu Val
290                 295                 300

Thr Ser Asn Ala Ala Leu Thr Leu Arg Asn Phe Cys Asn Trp Gln Lys
305                 310                 315                 320

Gln His Asn Pro Pro Ser Asp Arg Asp Ala Glu His Tyr Asp Thr Ala
                325                 330                 335

Ile Leu Phe Thr Arg Gln Asp Leu Cys Gly Ser Gln Thr Cys Asp Thr
            340                 345                 350

Leu Gly Met Ala Asp Val Gly Thr Val Cys Asp Pro Ser Arg Ser Cys
        355                 360                 365

Ser Val Ile Glu Asp Asp Gly Leu Gln Ala Ala Phe Thr Thr Ala His
    370                 375                 380

Gln Leu Gly His Val Phe Asn Met Pro His Asp Asp Ala Lys Gln Cys
385                 390                 395                 400

Ala Ser Leu Asn Gly Val Asn Gln Asp Ser His Met Met Ala Ser Met
                405                 410                 415

Leu Ser Asn Leu Asp His Ser Gln Pro Trp Ser Pro Cys Ser Ala Tyr
            420                 425                 430

Met Ile Thr Ser Phe Leu Asp Asn Gly His Gly Glu Cys Leu Met Asp
        435                 440                 445

Lys Pro Gln Asn Pro Ile Gln Leu Pro Gly Asp Leu Pro Gly Thr Ser
```

```
              450                 455                 460
Tyr Asp Ala Asn Arg Gln Cys Gln Phe Thr Phe Gly Glu Asp Ser Lys
465                 470                 475                 480

His Cys Pro Asp Ala Ala Ser Thr Cys Ser Thr Leu Trp Cys Thr Gly
                485                 490                 495

Thr Ser Gly Gly Val Leu Val Cys Gln Thr Lys His Phe Pro Trp Ala
            500                 505                 510

Asp Gly Thr Ser Cys Gly Glu Gly Lys Trp Cys Ile Asn Gly Lys Cys
            515                 520                 525

Val Asn Lys Thr Asp Arg Lys His Phe Asp Thr Pro Phe His Gly Ser
530                 535                 540

Trp Gly Met Trp Gly Pro Trp Gly Asp Cys Ser Arg Thr Cys Gly Gly
545                 550                 555                 560

Gly Val Gln Tyr Thr Met Arg Glu Cys Asp Asn Pro Val Pro Lys Asn
                565                 570                 575

Gly Gly Lys Tyr Cys Glu Gly Lys Arg Val Arg Tyr Arg Ser Cys Asn
            580                 585                 590

Leu Glu Asp Cys Pro Asp Asn Asn Gly Lys Thr Phe Arg Glu Glu Gln
            595                 600                 605

Cys Glu Ala His Asn Glu Phe Ser Lys Ala Ser Phe Gly Ser Gly Pro
610                 615                 620

Ala Val Glu Trp Ile Pro Lys Tyr Ala Gly Val Ser Pro Lys Asp Arg
625                 630                 635                 640

Cys Lys Leu Ile Cys Gln Ala Lys Gly Ile Gly Tyr Phe Phe Val Leu
                645                 650                 655

Gln Pro Lys Val Val Asp Gly Thr Pro Cys Ser Pro Asp Ser Thr Ser
            660                 665                 670

Val Cys Val Gln Gly Gln Cys Val Lys Ala Gly Cys Asp Arg Ile Ile
            675                 680                 685

Asp Ser Lys Lys Lys Phe Asp Lys Cys Gly Val Cys Gly Gly Asn Gly
690                 695                 700

Ser Thr Cys Lys Lys Ile Ser Gly Ser Val Thr Ser Ala Lys Pro Gly
705                 710                 715                 720

Tyr His Asp Ile Ile Thr Ile Pro Thr Gly Ala Thr Asn Ile Glu Val
                725                 730                 735

Lys Gln Arg Asn Gln Arg Gly Ser Arg Asn Asn Gly Ser Phe Leu Ala
            740                 745                 750

Ile Lys Ala Ala Asp Gly Thr Tyr Ile Leu Asn Gly Asp Tyr Thr Leu
            755                 760                 765

Ser Thr Leu Glu Gln Asp Ile Met Tyr Lys Gly Val Val Leu Arg Tyr
770                 775                 780

Ser Gly Ser Ser Ala Ala Leu Glu Arg Ile Arg Ser Phe Ser Pro Leu
785                 790                 795                 800

Lys Glu Pro Leu Thr Ile Gln Val Leu Thr Val Gly Asn Ala Leu Arg
                805                 810                 815

Pro Lys Ile Lys Tyr Thr Tyr Phe Val Lys Lys Lys Glu Ser Phe
            820                 825                 830

Asn Ala Ile Pro Thr Phe Ser Ala Trp Val Ile Glu Glu Trp Gly Glu
            835                 840                 845

Cys Ser Lys Ser Cys Glu Leu Gly Trp Gln Arg Arg Leu Val Glu Cys
            850                 855                 860

Arg Asp Ile Asn Gly Gln Pro Ala Ser Glu Cys Ala Lys Glu Val Lys
865                 870                 875                 880
```

```
Pro Ala Ser Thr Arg Pro Cys Ala Asp His Pro Cys Pro Gln Trp Gln
                885                 890                 895
Leu Gly Glu Trp Ser Ser Cys Ser Lys Thr Cys Gly Lys Gly Tyr Lys
            900                 905                 910
Lys Arg Ser Leu Lys Cys Leu Ser His Asp Gly Gly Val Leu Ser His
        915                 920                 925
Glu Ser Cys Asp Pro Leu Lys Lys Pro Lys His Phe Ile Asp Phe Cys
    930                 935                 940
Thr Met Ala Glu Cys Ser
945             950

<210> SEQ ID NO 32
<211> LENGTH: 2907
<212> TYPE: DNA
<213> ORGANISM: Homo sapiens

<400> SEQUENCE: 32
```

| | | | |
|---|---|---|---|
| gcaatgcagc gagctgtgcc cgaggggttc ggaaggcgca agctgggcag cgacatgggg | 60 |
| aacgcggagc gggctccggg gtctcggagc tttgggcccg tacccacgct gctgctgctc | 120 |
| gccgcggcgc tactggccgt gtcggacgca ctcgggcgcc cctccgagga ggacgaggag | 180 |
| ctagtggtgc cggagctgga gcgcgccccg ggacacggga ccacgcgcct ccgcctgcac | 240 |
| gcctttgacc agcagctgga tctggagctg cggcccgaca gcagtttttt ggcgcccggc | 300 |
| ttcacgctcc agaacgtggg gcgcaaatcc gggtccgaga cgccgcttcc ggaaaccgac | 360 |
| ctggcgcact gcttctactc cggcaccgtg aatggcgatc ccagctcggc tgccgccctc | 420 |
| agcctctgcg agggcgtgcg cggcgccttc tacctgctgg gggaggcgta tttcatccag | 480 |
| ccgctgcccg ccgccagcga gcgcctcgcc accgccgccc aggggagaa gccgccggca | 540 |
| ccactacagt tccacctcct gcggcggaat cggcagggcg acgtcggcgg cacgtgcggg | 600 |
| gtcgtggacg acgagccccg gccgactggg aaagcggaga ccgaagacga ggacgaaggg | 660 |
| actgagggcg aggacgaagg ggctcagtgg tcgccgcagg acccggcact gcaaggcgta | 720 |
| ggacagccca caggaactgg aagcataaga aagaagcgat ttgtgtccag tcaccgctat | 780 |
| gtggaaacca tgcttgtggc agaccagtcg atggcagaat tccacggcag tggtctaaag | 840 |
| cattaccttc tcacgttgtt ttcggtggca gccagattgt acaaacaccc cagcattcgt | 900 |
| aattcagtta gcctggtggt ggtgaagatc ttggtcatcc acgatgaaca gaagggccg | 960 |
| gaagtgacct ccaatgctgc cctcactctg cggaactttt gcaactggca gaagcagcac | 1020 |
| aacccaccca gtgaccggga tgcagagcac tatgacacag caattctttt caccagacag | 1080 |
| gacttgtgtg gtcccagac atgtgatact cttgggatgg ctgatgttgg aactgtgtgt | 1140 |
| gatccgagca gaagctgctc cgtcatagaa gatgatggtt acaagctgc cttcaccaca | 1200 |
| gcccatcaat taggccacgt gtttaacatg ccacatgatg atgcaaagca gtgtgccagc | 1260 |
| cttaatggtg tgaaccagga ttcccacatg atggcgtcaa tgctttccaa cctggaccac | 1320 |
| agccagcctt ggtctccttg cagtgcctac atgattacat catttctgga taatggtcat | 1380 |
| ggggaatgtt tgatggacaa gcctcagaat cccatacagc tcccaggcga tctccctggc | 1440 |
| acctcgtacg atgccaaccg gcagtgccag tttacatttg ggaggactc caaacactgc | 1500 |
| cccgatgcag ccagcacatg tagcaccttg tggtgtaccg gcacctctgg tggggtgctg | 1560 |
| gtgtgtcaaa ccaaacactt cccgtgggcg gatggcacca gctgtggaga agggaaatgg | 1620 |
| tgtatcaacg gcaagtgtgt gaacaaaacc gacagaaagc attttgatac gccttttcat | 1680 |

-continued

```
ggaagctggg gaatgtgggg gccttgggga gactgttcga gaacgtgcgg tggaggagtc    1740
cagtacacga tgagggaatg tgacaaccca gtcccaaaga atggagggaa gtactgtgaa    1800
ggcaaacgag tgcgctacag atcctgtaac cttgaggact gtccagacaa taatggaaaa    1860
acctttagag aggaacaatg tgaagcacac aacgagtttt caaaagcttc ctttgggagt    1920
gggcctgcgg tggaatggat tcccaagtac gctggcgtct caccaaagga caggtgcaag    1980
ctcatctgcc aagccaaagg cattggctac ttcttcgttt tgcagcccaa ggttgtagat    2040
ggtactccat gtagcccaga ttccacctct gtctgtgtgc aaggacagtg tgtaaaagct    2100
ggttgtgatc gcatcataga ctccaaaaag aagtttgata atgtggtgt ttgcggggga    2160 aatggatcta cttgtaaaaa aatatcagga tcagttacta gtgcaaaacc tggatatcat    2220
gatatcatca caattccaac tggagccacc aacatcgaag tgaaacagcg aaccagagg    2280 ggatccagga acaatggcag ctttcttgcc atcaaagctg ctgatggcac atatattctt    2340
aatggtgact acactttgtc caccttagag caagacatta tgtacaaagg tgttgtcttg    2400
aggtacagcg gctcctctgc ggcattggaa agaattcgca gctttagccc tctcaaagag    2460
cccttgacca tccaggttct tactgtgggc aatgcccttc gacctaaaat taaatacacc    2520
tacttcgtaa agaagaagaa ggaatctttc aatgctatcc ccactttttc agcatgggtc    2580
attgaagagt ggggcgaatg ttctaagtca tgtgaattgg gttggcagag aagactggta    2640
gaatgccgag acattaatgg acagcctgct tccgagtgtg caaggaagt gaagccagcc    2700 agcaccagac cttgtgcaga ccatccctgc ccccagtggc agctggggga gtggtcatca    2760
tgttctaaga cctgtgggaa gggttacaaa aaaagaagct tgaagtgtct gtcccatgat    2820
ggaggggtgt tatctcatga gagctgtgat cctttaaaga aacctaaaca tttcatagac    2880
ttttgcacaa tggcagaatg cagttaa                                        2907
```

<210> SEQ ID NO 33
<211> LENGTH: 596
<212> TYPE: PRT
<213> ORGANISM: Mus musculus

<400> SEQUENCE: 33

```
Met Gly Asp Val Gln Arg Ala Ala Arg Ser Arg Gly Ser Leu Ser Ala
1               5                   10                  15

His Met Leu Leu Leu Leu Ala Ser Ile Thr Met Leu Leu Cys Ala
            20                  25                  30

Arg Gly Ala His Gly Arg Pro Thr Glu Glu Asp Glu Glu Leu Val Leu
        35                  40                  45

Pro Ser Leu Glu Arg Ala Pro Gly His Asp Ser Thr Thr Thr Arg Leu
    50                  55                  60

Arg Leu Asp Ala Phe Gly Gln Gln Leu His Leu Lys Leu Gln Pro Asp
65                  70                  75                  80

Ser Gly Phe Leu Ala Pro Gly Phe Thr Leu Gln Thr Val Gly Arg Ser
                85                  90                  95

Pro Gly Ser Glu Ala Gln His Leu Asp Pro Thr Gly Asp Leu Ala His
            100                 105                 110

Cys Phe Tyr Ser Gly Thr Val Asn Gly Asp Pro Gly Ser Ala Ala Ala
        115                 120                 125

Leu Ser Leu Cys Glu Gly Val Arg Gly Ala Phe Tyr Leu Gln Gly Glu
    130                 135                 140

Glu Phe Phe Ile Gln Pro Ala Pro Gly Val Ala Thr Glu Arg Leu Ala
```

-continued

```
            145                 150                 155                 160
Pro Ala Val Pro Glu Glu Ser Ser Ala Arg Pro Gln Phe His Ile
                    165                 170                 175
Leu Arg Arg Arg Arg Gly Ser Gly Gly Ala Lys Cys Gly Val Met
                180                 185                 190
Asp Asp Glu Thr Leu Pro Thr Ser Asp Ser Arg Pro Glu Ser Gln Asn
            195                 200                 205
Thr Arg Asn Gln Trp Pro Val Arg Asp Pro Thr Pro Gln Asp Ala Gly
210                 215                 220
Lys Pro Ser Gly Pro Gly Ser Ile Arg Lys Lys Arg Phe Val Ser Ser
225                 230                 235                 240
Pro Arg Tyr Val Glu Thr Met Leu Val Ala Asp Gln Ser Met Ala Asp
                    245                 250                 255
Phe His Gly Ser Gly Leu Lys His Tyr Leu Leu Thr Leu Phe Ser Val
                260                 265                 270
Ala Ala Arg Phe Tyr Lys His Pro Ser Ile Arg Asn Ser Ile Ser Leu
            275                 280                 285
Val Val Val Lys Ile Leu Val Ile Tyr Glu Glu Gln Lys Gly Pro Glu
            290                 295                 300
Val Thr Ser Asn Ala Ala Leu Thr Leu Arg Asn Phe Cys Asn Trp Gln
305                 310                 315                 320
Lys Gln His Asn Ser Pro Ser Asp Arg Asp Pro Glu His Tyr Asp Thr
                    325                 330                 335
Ala Ile Leu Phe Thr Arg Gln Asp Leu Cys Gly Ser His Thr Cys Asp
                340                 345                 350
Thr Leu Gly Met Ala Asp Val Gly Thr Val Cys Asp Pro Ser Arg Ser
            355                 360                 365
Cys Ser Val Ile Glu Asp Asp Gly Leu Gln Ala Ala Phe Thr Thr Ala
            370                 375                 380
His Gln Leu Gly His Val Phe Asn Met Pro His Asp Asp Ala Lys His
385                 390                 395                 400
Cys Ala Ser Leu Asn Gly Val Thr Gly Asp Ser His Leu Met Ala Ser
                    405                 410                 415
Met Leu Ser Ser Leu Asp His Ser Gln Pro Trp Ser Pro Cys Ser Ala
                420                 425                 430
Tyr Met Val Thr Ser Phe Leu Asp Asn Gly His Gly Glu Cys Leu Met
            435                 440                 445
Asp Lys Pro Gln Asn Pro Ile Lys Leu Pro Ser Asp Leu Pro Gly Thr
450                 455                 460
Leu Tyr Asp Ala Asn Arg Gln Cys Gln Phe Thr Phe Gly Glu Glu Ser
465                 470                 475                 480
Lys His Cys Pro Asp Ala Ala Ser Thr Cys Thr Thr Leu Trp Cys Thr
                    485                 490                 495
Gly Thr Ser Gly Gly Leu Leu Val Cys Gln Thr Lys His Phe Pro Trp
                500                 505                 510
Ala Asp Gly Thr Ser Cys Gly Glu Gly Lys Trp Cys Val Ser Gly Lys
            515                 520                 525
Cys Val Asn Lys Thr Asp Met Lys His Phe Ala Thr Pro Val His Gly
            530                 535                 540
Ser Trp Gly Pro Trp Gly Pro Trp Gly Asp Cys Ser Arg Thr Cys Gly
545                 550                 555                 560
Gly Gly Val Gln Tyr Thr Met Arg Glu Cys Asp Asn Pro Val Pro Lys
                    565                 570                 575
```

Asn Gly Gly Lys Tyr Cys Glu Gly Lys Arg Val Arg Tyr Arg Ser Cys
            580                 585                 590

Asn Ile Glu Asp
        595

<210> SEQ ID NO 34
<211> LENGTH: 1794
<212> TYPE: DNA
<213> ORGANISM: Mus musculus

<400> SEQUENCE: 34

| | | | | | |
|---|---|---|---|---|---|
| gacatggggg | acgtccagcg | ggcagcgaga | tctcggggct | ctctgtccgc | acacatgctg | 60 |
| ttgctgctcc | tcgcttccat | aacaatgctg | ctatgtgcgc | ggggcgcaca | cgggcgcccc | 120 |
| acggaggaag | atgaggagct | ggtcctgccc | tcgctggagc | gcgccccggg | ccacgattcc | 180 |
| accaccacac | gccttcgtct | ggacgccttt | ggccagcagc | tacatctgaa | gttgcagccg | 240 |
| gacagcggtt | tcttggcgcc | tggcttcacc | ctgcagactg | tggggcgcag | tcccgggtcc | 300 |
| gaggcacaac | atctggaccc | caccggggac | ctggctcact | gcttctactc | tggcacggtg | 360 |
| aacggtgatc | ccggctctgc | cgcagccctc | agcctctgtg | aaggtgtgcg | tggtgccttc | 420 |
| tacctacaag | gagaggagtt | cttcattcag | ccagcgcctg | gagtggccac | cgagcgcctg | 480 |
| gcccctgccg | tgcccgagga | ggagtcatcc | gcacggccgc | agttccacat | cctgaggcga | 540 |
| aggcggcggg | gcagtggcgg | cgccaagtgc | ggcgtcatgg | acgacgagac | cctgccaacc | 600 |
| agcgactcgc | gacccgagag | ccagaacacc | cggaaccagt | ggcctgtgcg | ggaccccacg | 660 |
| cctcaggacg | cgggaaagcc | atcaggacca | ggaagcataa | ggaagaagcg | atttgtgtcc | 720 |
| agcccccgtt | atgtggaaac | catgctcgtg | gctgaccagt | ccatggccga | cttccacggc | 780 |
| agcggtctaa | agcattacct | tctaaccctg | ttctcggtgg | cagccaggtt | ttacaagcat | 840 |
| cccagcatta | ggaattcaat | tagcctggtg | gtggtgaaga | tcttggtcat | atatgaggag | 900 |
| cagaagggac | cagaagttac | ctccaatgca | gctctcaccc | ttcggaattt | ctgcaactgg | 960 |
| cagaaacaac | acaacagccc | cagtgaccgg | gatccagagc | actatgacac | tgcaattctg | 1020 |
| ttcaccagac | aggatttatg | tggctcccac | acgtgtgaca | ctctcgggat | ggcagatgtt | 1080 |
| ggaactgtat | gtgaccccag | caggagctgc | tcagtcatag | aagatgatgg | tttgcaagcc | 1140 |
| gccttcacca | cagcccacca | attgggccat | gtgtttaaca | tgccgcacga | tgatgctaag | 1200 |
| cactgtgcca | gcttgaatgg | tgtgactggc | gattctcatc | tgatggcctc | gatgctctcc | 1260 |
| agcttagacc | atagccagcc | ctggtcacct | tgcagtgcct | acatggtcac | gtccttccta | 1320 |
| gataatggac | acggggaatg | tttgatggac | aagccccaga | tccaatcaa | gctcccttct | 1380 |
| gatcttcccg | gtaccttgta | cgatgccaac | cgccagtgtc | agtttacatt | cggagaggaa | 1440 |
| tccaagcact | gccctgatgc | agccagcaca | tgtactaccc | tgtggtgcac | tgcaccctcc | 1500 |
| ggtggcttac | tggtgtgcca | aacaaaacac | ttcccttggg | cagatggcac | cagctgtgga | 1560 |
| gaagggaagt | ggtgtgtcag | tgcaagtgc | gtgaacaaga | cagacatgaa | gcattttgct | 1620 |
| actcctgttc | atggaagctg | gggaccatgg | ggaccgtggg | gagactgctc | aagaacctgt | 1680 |
| ggtggtggag | ttcaatacac | aatgagagaa | tgtgacaacc | cagtcccaaa | gaacggaggg | 1740 |
| aagtactgtg | aaggcaaacg | agtccgctac | aggtcctgta | acatcgagga | ctaa | 1794 |

<210> SEQ ID NO 35
<211> LENGTH: 595
<212> TYPE: PRT

<213> ORGANISM: Homo sapiens

<400> SEQUENCE: 35

```
Met Gly Asn Ala Glu Arg Ala Pro Gly Ser Arg Ser Phe Gly Pro Val
1               5                   10                  15

Pro Thr Leu Leu Leu Ala Ala Leu Leu Ala Val Ser Asp Ala
            20                  25                  30

Leu Gly Arg Pro Ser Glu Glu Asp Glu Glu Leu Val Val Pro Glu Leu
            35                  40                  45

Glu Arg Ala Pro Gly His Gly Thr Thr Arg Leu Arg Leu His Ala Phe
        50                  55                  60

Asp Gln Gln Leu Asp Leu Glu Leu Arg Pro Asp Ser Ser Phe Leu Ala
65                  70                  75                  80

Pro Gly Phe Thr Leu Gln Asn Val Gly Arg Lys Ser Gly Ser Glu Thr
                85                  90                  95

Pro Leu Pro Glu Thr Asp Leu Ala His Cys Phe Tyr Ser Gly Thr Val
            100                 105                 110

Asn Gly Asp Pro Ser Ser Ala Ala Leu Ser Leu Cys Glu Gly Val
        115                 120                 125

Arg Gly Ala Phe Tyr Leu Leu Gly Glu Ala Tyr Phe Ile Gln Pro Leu
130                 135                 140

Pro Ala Ala Ser Glu Arg Leu Ala Thr Ala Ala Pro Gly Glu Lys Pro
145                 150                 155                 160

Pro Ala Pro Leu Gln Phe His Leu Leu Arg Arg Asn Arg Gln Gly Asp
                165                 170                 175

Val Gly Gly Thr Cys Gly Val Val Asp Asp Glu Pro Arg Pro Thr Gly
            180                 185                 190

Lys Ala Glu Thr Glu Asp Glu Asp Glu Gly Thr Glu Gly Glu Asp Glu
        195                 200                 205

Gly Ala Gln Trp Ser Pro Gln Asp Pro Ala Leu Gln Gly Val Gly Gln
210                 215                 220

Pro Thr Gly Thr Gly Ser Ile Arg Lys Lys Arg Phe Val Ser Ser His
225                 230                 235                 240

Arg Tyr Val Glu Thr Met Leu Val Ala Asp Gln Ser Met Ala Glu Phe
                245                 250                 255

His Gly Ser Gly Leu Lys His Tyr Leu Leu Thr Leu Phe Ser Val Ala
            260                 265                 270

Ala Arg Leu Tyr Lys His Pro Ser Ile Arg Asn Ser Val Ser Leu Val
        275                 280                 285

Val Val Lys Ile Leu Val Ile His Asp Glu Gln Lys Gly Pro Glu Val
290                 295                 300

Thr Ser Asn Ala Ala Leu Thr Leu Arg Asn Phe Cys Asn Trp Gln Lys
305                 310                 315                 320

Gln His Asn Pro Pro Ser Asp Arg Asp Ala Glu His Tyr Asp Thr Ala
                325                 330                 335

Ile Leu Phe Thr Arg Gln Asp Leu Cys Gly Ser Gln Thr Cys Asp Thr
            340                 345                 350

Leu Gly Met Ala Asp Val Gly Thr Val Cys Asp Pro Ser Arg Ser Cys
        355                 360                 365

Ser Val Ile Glu Asp Asp Gly Leu Gln Ala Ala Phe Thr Thr Ala His
370                 375                 380

Gln Leu Gly His Val Phe Asn Met Pro His Asp Asp Ala Lys Gln Cys
385                 390                 395                 400
```

```
Ala Ser Leu Asn Gly Val Asn Gln Asp Ser His Met Met Ala Ser Met
                405                 410                 415
Leu Ser Asn Leu Asp His Ser Gln Pro Trp Ser Pro Cys Ser Ala Tyr
            420                 425                 430
Met Ile Thr Ser Phe Leu Asp Asn Gly His Gly Glu Cys Leu Met Asp
        435                 440                 445
Lys Pro Gln Asn Pro Ile Gln Leu Pro Gly Asp Leu Pro Gly Thr Ser
    450                 455                 460
Tyr Asp Ala Asn Arg Gln Cys Gln Phe Thr Phe Gly Glu Asp Ser Lys
465                 470                 475                 480
His Cys Pro Asp Ala Ala Ser Thr Cys Ser Thr Leu Trp Cys Thr Gly
                485                 490                 495
Thr Ser Gly Gly Val Leu Val Cys Gln Thr Lys His Phe Pro Trp Ala
            500                 505                 510
Asp Gly Thr Ser Cys Gly Glu Gly Lys Trp Cys Ile Asn Gly Lys Cys
        515                 520                 525
Val Asn Lys Thr Asp Arg Lys His Phe Asp Thr Pro Phe His Gly Ser
    530                 535                 540
Trp Gly Met Trp Gly Pro Trp Gly Asp Cys Ser Arg Thr Cys Gly Gly
545                 550                 555                 560
Gly Val Gln Tyr Thr Met Arg Glu Cys Asp Asn Pro Val Pro Lys Asn
                565                 570                 575
Gly Gly Lys Tyr Cys Glu Gly Lys Arg Val Arg Tyr Arg Ser Cys Asn
            580                 585                 590
Leu Glu Asp
    595

<210> SEQ ID NO 36
<211> LENGTH: 1842
<212> TYPE: DNA
<213> ORGANISM: Homo sapiens

<400> SEQUENCE: 36
gcaatgcagc gagctgtgcc cgaggggttc ggaaggcgca agctgggcag cgacatgggg      60
aacgcggagc gggctccggg gtctcggagc tttgggcccg tacccacgct gctgctgctc     120
gccgcggcgc tactggccgt gtcggacgca ctcgggcgcc cctccgagga ggacgaggag     180
ctagtggtgc cggagctgga gcgcgccccg ggacacggga ccacgcgcct ccgcctgcac     240
gcctttgacc agcagctgga tctggagctg cggcccgaca gcagcttttt ggcgcccggc     300
ttcacgctcc agaacgtggg gcgcaaatcc gggtccgaga cgccgcttcc ggaaaccgac     360
ctggcgcact gcttctactc cggcaccgtg aatggcgatc ccagctcggc tgccgccctc     420
agcctctgcg agggcgtgcg cggcgccttc tacctgctgg gggaggcgta tttcatccag     480
ccgctgcccg ccgccagcga gcgcctcgcc accgccgccc aggggagaa gccgccggca     540
ccactacagt tccacctcct gcggcggaat cggcagggcg acgtcggcgg cacgtgcggg     600
gtcgtggacg acgagccccg gccgactggg aaagcggaga ccgaagacga ggacgaaggg     660
actgagggcg aggacgaagg ggctcagtgg tcgccgcagg acccggcact gcaaggcgta     720
ggacagccca caggaactgg aagcataaga aagaagcgat tgtgtccag tcaccgctat     780
gtggaaacca tgcttgtggc agaccagtcg atggcagaat tccacggcag tggtctaaag     840
cattaccttc tcacgttgtt ttcggtggca gccagattgt acaaacaccc cagcattcgt     900
aattcagtta gcctggtggt ggtgaagatc ttggtcatcc acgatgaaca gaaggggccg     960
```

-continued

```
gaagtgacct ccaatgctgc cctcactctg cggaactttt gcaactggca gaagcagcac    1020
aacccaccca gtgaccggga tgcagagcac tatgacacag caattctttt caccagacag    1080
gacttgtgtg ggtcccagac atgtgatact cttgggatgg ctgatgttgg aactgtgtgt   1140
gatccgagca gaagctgctc cgtcatagaa gatgatggtt tacaagctgc cttcaccaca    1200
gcccatcaat taggccacgt gtttaacatg ccacatgatg atgcaaagca gtgtgccagc    1260
cttaatggtg tgaaccagga ttcccacatg atggcgtcaa tgctttccaa cctggaccac    1320
agccagcctt ggtctccttg cagtgcctac atgattacat catttctgga taatggtcat    1380
ggggaatgtt tgatggacaa gcctcagaat cccatacagc tcccaggcga tctccctggc    1440
acctcgtacg atgccaaccg gcagtgccag tttacatttg gggaggactc caaacactgc    1500
cccgatgcag ccagcacatg tagcaccttg tggtgtaccg gcacctctgg tggggtgctg    1560
gtgtgtcaaa ccaaacactt cccgtgggcg gatggcacca gctgtggaga agggaaatgg   1620
tgtatcaacg gcaagtgtgt gaacaaaacc gacagaaagc attttgatac gccttttcat    1680
ggaagctggg gaatgtgggg gccttgggga gactgttcga gaacgtgcgg tggaggagtc    1740
cagtacacga tgagggaatg tgacaaccca gtcccaaaga atggagggaa gtactgtgaa    1800
ggcaaacgag tgcgctacag atcctgtaac cttgaggact aa                       1842
```